(12) United States Patent
Frey et al.

(10) Patent No.: US 7,244,602 B2
(45) Date of Patent: Jul. 17, 2007

(54) POLYMERASE CHIMERAS

(75) Inventors: Bruno Frey, Penzberg (DE); Britta Villbrandt, Braunschweig (DE); Dietmar Schomburg, Erftstadt (DE); Harald Sobek, Penzberg (DE); Waltraud Ankenbauer, Penzberg (DE)

(73) Assignee: Roche Diagnostics GmbH, MAnnheim (DE)

( * ) Notice: Subject to any disclaimer, the term of this patent is extended or adjusted under 35 U.S.C. 154(b) by 385 days.

(21) Appl. No.: 10/456,129

(22) Filed: Jun. 6, 2003

(65) Prior Publication Data
US 2004/0058362 A1 Mar. 25, 2004

Related U.S. Application Data

(62) Division of application No. 09/623,326, filed as application No. PCT/EP99/01674 on Mar. 15, 1999, now Pat. No. 6,607,883.

(30) Foreign Application Priority Data
Mar. 13, 1998 (DE) ................ 198 10 879

(51) Int. Cl.
C12N 9/12 (2006.01)
C12Q 1/68 (2006.01)
(52) U.S. Cl. ................ 435/194; 435/6; 435/91.1; 435/91.2; 536/22.1; 536/23.1
(58) Field of Classification Search ........... 435/194, 435/6, 91.1, 91.2; 536/22.1, 23.1
See application file for complete search history.

(56) References Cited

U.S. PATENT DOCUMENTS 5,466,591 A 11/1995 Abramson et al.
6,077,664 A 6/2000 Slater et al.

FOREIGN PATENT DOCUMENTS

EP 0 482 714 A1 4/1992
EP 0 892 058 A2 1/1999
WO WO 97/29209 8/1997

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
Sousa et al., "Single Crystals of a Chimeric T7/T3 RNA Polymerase with T3 Promoter Specificity", Journal of Crystal Growth, 1992, 122: 366-374.
Linda J. Reha-Krantz, "Are there highly conserved DNA polymerase 3' → 5' exonuclease motifs?", Gene 112 © 1992 Elsevier Science Publishers, p. 133-137.
Uemori et al., "Organization and nucleotide sequence of the DNA polymerase gene from the archaeon Pyrococcus furiosus", Nucleic Acids Research, 1993, vol. 21, No. 2 pp. 259-265.
Korolev et al., "Crystal structure of the large fragment of Thermus aquaticus DNA polymerase I at 2.5-Å resolution: Structural basis for thermostability", Sep. 1995, Proc. Natl. Acad. Sci. USA, vol. 92, pp. 9264-9268.
Joyce et al., "Nucleotide Sequence of the *Escherichia coli* polA Gene and Primary Structure of DNA Polymerase I*", 1982 The Journal of Biological Chemistry, vol. 257, No. 4, Issue of Feb. 25, pp. 1958-1964.

* cited by examiner

*Primary Examiner*—Richard Hutson
(74) *Attorney, Agent, or Firm*—Townsend and Townsend and Crew; Charles M. Doyle; Khea C. Nersesian

(57) ABSTRACT

The invention concerns polymerase chimeras which are composed of amino acid fragments representing domains and which combine properties of naturally occurring polymerases that are advantageous with regard to a particular application. It has surprisingly turned out that the domains from the various enzymes are active in the chimeras and exhibit cooperative behavior. In addition the present invention concerns a process for the production of the chimeras according to the invention and the use of these chimeras for the synthesis of nucleic acids e.g. during a polymerase chain reaction. Moreover the present invention concerns a kit which contains the polymerase chimeras according to the invention.

4 Claims, 31 Drawing Sheets

Figure 7:
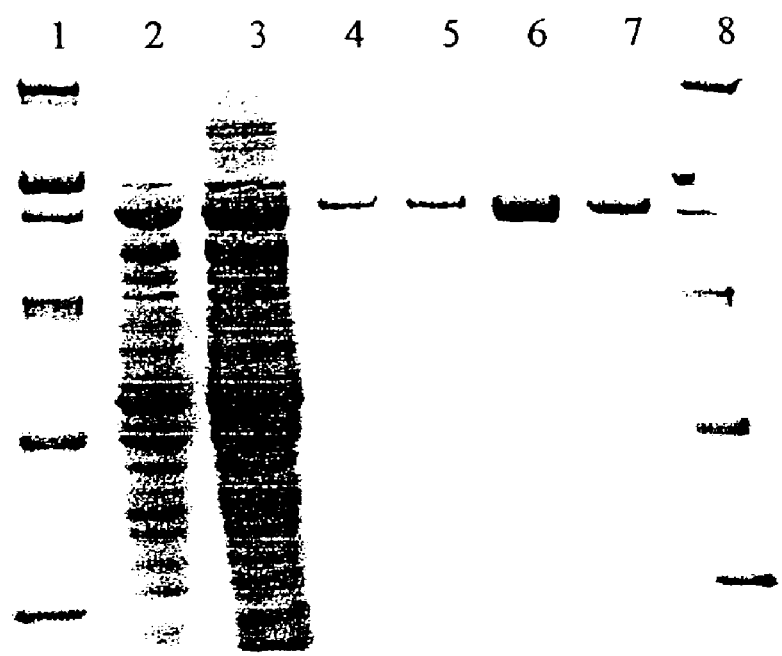

Figure 1/1
SEQ ID No.: 1

DNA sequence:
```
   1 ATGAGGGGCT CGCATCACCA TCACCATCAC GCTGCTGACG ATGACGATAA
  51 AATGAGGGGC ATGCTACCGC TATTTGAGCC CAAGGGCCGG GTCCTCCTGG
 101 TCGACGGCCA CCACCTGGCC TACCGCACCT TCCACGCCCT GAAGGGCCTC
 151 ACCACCAGCC GGGGGGAGCC GGTGCAGGCG GTCTACGGCT TCGCCAAGAG
 201 CCTCCTCAAG GCCCTCAAGG AGGACGGGGA CGCGGTGATC GTGGTCTTTG
 251 ACGCCAAGGC CCCCTCCTTC CGCCACGAGG CCTACGGGGG GTACAAGGCG
 301 GGCCGGGCCC CCACGCCGGA GGACTTTCCC CGGCAACTCG CCCTCATCAA
 351 GGAGCTGGTG GACCTCCTGG GCTGGCGCG CCTCGAGGTC CCGGGCTACG
 401 AGGCGGACGA CGTCCTGGCC AGCCTGGCCA AGAAGGCGGA AAAGGAGGGC
 451 TACGAGGTCC GCATCCTCAC CGCCGACAAA GACCTTTACC AGCTCCTTTC
 501 CGACCGCATC CACGTCCTCC ACCCCGAGGG GTACCTCATC ACCCCGGCCT
 551 GGCTTTGGGA AAAGTACGGC CTGAGGCCCG ACCAGTGGGC CGACTACCGG
 601 GCCCTGACCG GGGACGAGTC CGACAACCTT CCCGGGGTCA AGGGCATCGG
 651 GGAGAAGACG GCGAGGAAGC TTCTGGAGGA GTGGGGGAGC CTGGAAGCCC
 701 TCCTCAAGAA CCTGGACCGG CTGAAGCCCG CCATCCGGGA GAAGATCCTG
 751 GCCCACATGG ACGATCTGAA GCTCTCCTGG GACCTGGCCA AGGTGCGCAC
 801 CGACCTGCCC CTGGAGGTGG ACTTCGCCAA AAGGCGGGAG CCCGACCGGG
 851 AGAGGCTTAG GGCCTTTCTG GAGAGGCTTG AGTTTGGCAG CCTCCTCCAC
 901 GAGTTCGCC TTCTGGAAAG CCCCTATGAC AACTACGTCA CCATCCTTGA
 951 TGAAGAAACA CTGAAAGCGT GGATTGCGAA GCTGGAAAAA GCGCCGGTAT
1001 TTGCATTTGA TACCGAAACC GACAGCCTTG ATAACATCTC TGCTAACCTG
1051 GTCGGGCTTT CTTTTGCTAT CGAGCCAGGC GTAGCGGCAT ATATTCCGGT
1101 TGCTCATGAT TATCTTGATG CGCCCGATCA AATCTCTCGC GAGCGTGCAC
1151 TCGAGTTGCT AAAACCGCTG CTGGAAGATG AAAAGGCGCT GAAGGTCGGG
1201 CAAAACCTGA ATACGATCG CGGTATTCTG GCGAACTACG GCATTGAACT
1251 GCGTGGGATT GCGTTTGATA CCATGCTGGA GTCCTACATT CTCAATAGCG
1301 TTGCCGGGCG TCACGATATG GACAGCCTCG CGGAACGTTG GTTGAAGCAC
1351 AAAACCATCA CTTTTGAAGA GATTGCTGGT AAAGGCAAAA ATCAACTGAC
1401 CTTTAACCAG ATTGCCCTCG AAGAAGCCGG ACGTTACGCC GCCGAAGATG
1451 CAGATGTCAC CTTGCAGTTG CATCTGAAAA TGTGGCCGGA TCTGCAAAAA
1501 CACGAGAGGC TCCTTTGGCT TTACCGGGAG GTGGAGAGGC CCCTTTCCGC
1551 TGTCCTGGCC CACATGGAGG CCACGGGGGT GCGCCTGGAC GTGGCCTATC
1601 TCAGGGCCTT GTCCCTGGAG GTGGCCGAGG AGGTCGCCCG CCTCGAGGCC
1651 GAGGTCTTCC GCCTGGCCGG CCACCCCTTC AACCTCAACT CCCGGGACCA
1701 GCTGGAAAGG GTCCTCTTTG ACGAGCTAGG CTTCCCGCC ATCGGCAAGA
1751 CGGAGAAGAC CGGCAAGCGC TCCACCAGCG CCGCCGTCCT GGAGGCCCTC
1801 CGCGAGGCCC ACCCCATCGT GGAGAAGATC CTGCAGTACC GGGAGCTCAC
1851 CAAGCTGAAG AGCACCTACA TTGACCCCTT GCCGGACCTC ATCCACCCCA
1901 GGACGGGCCG CCTCCACACC CGCTTCAACC AGACGGCCAC GGCCACGGGC
1951 AGGCTAAGTA GCTCCGATCC CAACCTCCAG AACATCCCCG TCCGCACCCC
2001 GCTTGGGCAG AGGATCCGCC GGGCCTTCAT CGCCGAGGAG GGTGGCTAT
2051 TGGTGGCCCT GGACTATAGC CAGATAGAGC TCAGGGTGCT GGCCCACCTC
2101 TCCGGCGACG AGAACCTGAT CCGGGTCTTC CAGGAGGGGC GGGACATCCA
2151 CACGGAGACC GCCAGCTGGA TGTTCGGCGT CCCCCGGGAG GCCGTGGACC
2201 CCCTGATGCG CCGGGCGGCC AAGACCATCA ACTTCGGGGT CCTCTACGGC
2251 ATGTCGGCCC ACCGCCTCTC CCAGGAGCTA GCCATCCCTT ACGAGGAGGC
2301 CCAGGCCTTC ATTGAGCGCT ACTTTCAGAG CTTCCCCAAG GTGCGGGCCT
2351 GGATTGAGAA GACCCTGGAG GAGGGCAGGA GGCGGGGGTA CGTGGAGACC
2401 CTCTTCGGCC GCCGCCGCTA CGTGCCAGAC CTAGAGGCCC GGGTGAAGAG
2451 CGTGCGGGAG GCGGCCGAGC GCATGGCCTT CAACATGCCC GTCCAGGGCA
2501 CCGCCGCCGA CCTCATGAAG CTGGCTATGG TGAAGCTCTT CCCCAGGCTG
```

Figure 1/2
SEQ ID No.: 1

```
2551 GAGGAAATGG GGGCCAGGAT GCTCCTTCAG GTCCACGACG AGCTGGTCCT
2601 CGAGGCCCCA AAAGAGAGGG CGGAGGCCGT GGCCCGGCTG GCCAAGGAGG
2651 TCATGGAGGG GGTGTATCCC CTGGCCGTGC CCTGGAGGT GGAGGTGGGG
2701 ATAGGGGAGG ACTGGCTCTC CGCCAAGGAG TGA
```

SEQ ID No.: 7 amino acid sequence:
```
  1  MRGSHHHHHH AADDDDKMRG MLPLFEPKGR VLLVDGHHLA YRTFHALKGL
 51  TTSRGEPVQA VYGFAKSLLK ALKEDGDAVI VVFDAKAPSF RHEAYGGYKA
101  GRAPTPEDFP RQLALIKELV DLLGLARLEV PGYEADDVLA SLAKKAEKEG
151  YEVRILTADK DLYQLLSDRI HVLHPEGYLI TPAWLWEKYG LRPDQWADYR
201  ALTGDESDNL PGVKGIGEKT ARKLLEEWGS LEALLKNLDR LKPAIREKIL
251  AHMDDLKLSW DLAKVRTDLP LEVDFAKRRE PDRERLRAFL ERLEFGSLLH
301  EFGLLESPYD NYVTILDEET LKAWIAKLEK APVFAFDTET DSLDNISANL
351  VGLSFAIEPG VAAYIPVAHD YLDAPDQISR ERALELLKPL LEDEKALKVG
401  QNLKYDRGIL ANYGIELRGI AFDTMLESYI LNSVAGRHDM DSLAERWLKH
451  KTITFEEIAG KGKNQLTFNQ IALEEAGRYA AEDADVTLQL HLKMWPDLQK
501  HERLLWLYRE VERPLSAVLA HMEATGVRLD VAYLRALSLE VAEEVARLEA
551  EVFRLAGHPF NLNSRDQLER VLFDELGLPA IGKTEKTGKR STSAAVLEAL
601  REAHPIVEKI LQYRELTKLK STYIDPLPDL IHPRTGRLHT RFNQTATATG
651  RLSSSDPNLQ NIPVRTPLGQ RIRRAFIAEE GWLLVALDYS QIELRVLAHL
701  SGDENLIRVF QEGRDIHTET ASWMFGVPRE AVDPLMRRAA KTINFGVLYG
751  MSAHRLSQEL AIPYEEAQAF IERYFQSFPK VRAWIEKTLE EGRRRGYVET
801  LFGRRRYVPD LEARVKSVRE AAERMAFNMP VQGTAADLMK LAMVKLFPRL
851  EEMGARMLLQ VHDELVLEAP KERAEAVARL AKEVMEGVYP LAVPLEVEVG
901  IGEDWLSAKE
```

Figure 2/1
SEQ ID No.: 2

DNA sequence:
```
   1 ATGAGGGGCT CGCATCACCA TCACCATCAC GCTGCTGACG ATGACGATAA
  51 AATGAGGGGC ATGCTACCGC TATTTGAGCC CAAGGGCCGG GTCCTCCTGG
 101 TCGACGGCCA CCACCTGGCC TACCGCACCT TCCACGCCCT GAAGGGCCTC
 151 ACCACCAGCC GGGGGGAGCC GGTGCAGGCG GTCTACGGCT TCGCCAAGAG
 201 CCTCCTCAAG GCCCTCAAGG AGGACGGGGA CGCGGTGATC GTGGTCTTTG
 251 ACGCCAAGGC CCCCTCCTTC CGCCACGAGG CCTACGGGGG GTACAAGGCG
 301 GGCCGGGCCC CCACGCCGGA GGACTTTCCC CGGCAACTCG CCCTCATCAA
 351 GGAGCTGGTG GACCTCCTGG GGCTGGCGCG CCTCGAGGTC CCGGGCTACG
 401 AGGCGGACGA CGTCCTGGCC AGCCTGGCCA AGAAGGCGGA AAAGGAGGGC
 451 TACGAGGTCC GCATCCTCAC CGCCGACAAA GACCTTTACC AGCTCCTTTC
 501 CGACCGCATC CACGTCCTCC ACCCCGAGGG GTACCTCATC ACCCCGGCCT
 551 GGCTTTGGGA AAAGTACGGC CTGAGGCCCG ACCAGTGGGC CGACTACCGG
 601 GCCCTGACCG GGGACGAGTC CGACAACCTT CCCGGGGTCA AGGGCATCGG
 651 GGAGAAGACG GCGAGGAAGC TTCTGGAGGA GTGGGGGAGC CTGGAAGCCC
 701 TCCTCAAGAA CCTGGACCGG CTGAAGCCCG CCATCCGGGA GAAGATCCTG
 751 GCCCACATGG ACGATCTGAA GCTCTCCTGG GACCTGGCCA AGGTGCGCAC
 801 CGACCTGCCC CTGGAGGTGG ACTTCGCCAA AAGGCGGGAG CCCGACCGGG
 851 AGAGGCTTAG GGCCTTTCTG GAGAGGCTTG AGTTTGGCAG CCTCCTCCAC
 901 GAGTTCGGCC TTCTGGAAAG CCCCTATGAC AACTACGTCA CCATCCTTGA
 951 TGAAGAAACA CTGAAAGCGT GGATTGCGAA GCTGGAAAAA GCGCCGGTAT
1001 TTGCATTTGA TACCGAAACC GACAGCCTTG ATAACATCTC TGCTAACCTG
1051 GTCGGGCTTT CTTTTGCTAT CGAGCCAGGC GTAGCGGCAT ATATTCCGGT
1101 TGCTCATGAT TATCTTGATG CGCCGATCA AATCTCTCGC GAGCGTGCAC
1151 TCGAGTTGCT AAAACCGCTG CTGGAAGATG AAAAGGCGCT GAAGGTCGGG
1201 CAAAACCTGA ATACGATCG CGGTATTCTG GCGAACTACG GCATTGAACT
1251 GCGTGGGATT GCGTTGATA CCATGCTGGA GTCCTACATT CTCAATAGCG
1301 TTGCCGGGCG TCACGATATG GACAGCCTCG CGGAACGTTG GTTGAAGCAC
1351 AAAACCATCA CTTTTGAAGA GATTGCTGGT AAAGGCAAAA ATCAACTGAC
1401 CTTTAACCAG ATTGCCCTCG AAGAAGCCGG ACGTTACGCC GCCGAAGATG
1451 CAGATGTCAC CTTGCAGTTG CATCTGAAAA TGTGGCCGGA TCTGCAAAAA
1501 CACAAAGGGC CGTTGAACGT CTTCGAGAAT ATCGAAATGC CGCTGGTGCC
1551 GGTGCTTTCA CGCATTGAAC GTAACGGTGT CGCCTGGAC GTGGCCTATC
1601 TCAGGGCCTT GTCCCTGGAG GTGGCCGAGG AGATCGCCCG CCTCGAGGCC
1651 GAGGTCTTCC GCCTGGCCGG CCACCCCTTC AACCTCAACT CCCGGGACCA
1701 GCTGGAAAGG GTCCTCTTTG ACGAGCTAGG GCTTCCCGCC ATCGGCAAGA
1751 CGGAGAAGAC CGGCAAGCGC TCCACCAGCG CCGCCGTCCT GGAGGCCCTC
1801 CGCGAGGCCC ACCCCATCGT GGAGAAGATC CTGCAGTACC GGGAGCTCAC
1851 CAAGCTGAAG AGCACCTACA TTGACCCCTT GCCGGACCTC ATCCACCCCA
1901 GGACGGGCCG CCTCCACACC CGCTTCAACC AGACGGCCAC GGCCACGGGC
1951 AGGCTAAGTA GCTCCGATCC CAACCTCCAG AACATCCCCG TCCGCACCCC
2001 GCTTGGGCAG AGGATCCGCC GGGCCTTCAT CGCCGAGGAG GGGTGGCTAT
2051 TGGTGGCCCT GGACTATAGC CAGATAGAGC TCAGGGTGCT GGCCCACCTC
2101 TCCGGCGACG AGAACCTGAT CCGGGTCTTC CAGGAGGGGC GGGACATCCA
2151 CACGGAGACC GCCAGCTGGA TGTTCGGCGT CCCCCGGGAG GCCGTGGACC
2201 CCCTGATGCG CCGGCGGCC AAGACCATCA ACTTCGGGGT CCTCTACGGC
2251 ATGTCGGCCC ACCGCCTCTC CCAGGAGCTA GCCATCCCTT ACGAGGAGGC
2301 CCAGGCCTTC ATTGAGCGCT ACTTTCAGAG CTTCCCCAAG GTGCGGGCCT
2351 GGATTGAGAA GACCCTGGAG GAGGGCAGGA GGCGGGGGTA CGTGGAGACC
2401 CTCTTCGGCC GCCGCCGCTA CGTGCCAGAC CTAGAGGCCC GGGTGAAGAG
2451 CGTGCGGGAG GCGGCCGAGC GCATGGCCTT CAACATGCCC GTCCAGGGCA
2501 CCGCCGCCGA CCTCATGAAG CTGGCTATGG TGAAGCTCTT CCCCAGGCTG
```

Figure 2/2
SEQ ID No.: 2

```
2551 GAGGAAATGG GGGCCAGGAT GCTCCTTCAG GTCCACGACG AGCTGGTCCT
2601 CGAGGCCCCA AAAGAGAGGG CGGAGGCCGT GGCCCGGCTG GCCAAGGAGG
2651 TCATGGAGGG GGTGTATCCC CTGGCCGTGC CCTGGAGGT GGAGGTGGGG
2701 ATAGGGGAGG ACTGGCTCTC CGCCAAGGAG TGA
```

SEQ ID No.: 8 amino acid sequence:

```
  1  MRGSHHHHHH AADDDDKMRG MLPLFEPKGR VLLVDGHHLA YRTFHALKGL
 51  TTSRGEPVQA VYGFAKSLLK ALKEDGDAVI VVFDAKAPSF RHEAYGGYKA
101  GRAPTPEDFP RQLALIKELV DLLGLARLEV PGYEADDVLA SLAKKAEKEG
151  YEVRILTADK DLYQLLSDRI HVLHPEGYLI TPAWLWEKYG LRPDQWADYR
201  ALTGDESDNL PGVKGIGEKT ARKLLEEWGS LEALLKNLDR LKPAIREKIL
251  AHMDDLKLSW DLAKVRTDLP LEVDFAKRRE PDRERLRAFL ERLEFGSLLH
301  EFGLLESPYD NYVTILDEET LKAWIAKLEK APVFAFDTET DSLDNISANL
351  VGLSFAIEPG VAAYIPVAHD YLDAPDQISR ERALELLKPL LEDEKALKVG
401  QNLKYDRGIL ANYGIELRGI AFDTMLESYI LNSVAGRHDM DSLAERWLKH
451  KTITFEEIAG KGKNQLTFNQ IALEEAGRYA AEDADVTLQL HLKMWPDLQK
501  HKGPLNVFEN IEMPLVPVLS RIERNGVRLD VAYLRALSLE VAEEIARLEA
551  EVFRLAGHPF NLNSRDQLER VLFDELGLPA IGKTEKTGKR STSAAVLEAL
601  REAHPIVEKI LQYRELTKLK STYIDPLPDL IHPRTGRLHT RFNQTATATG
651  RLSSSDPNLQ NIPVRTPLGQ RIRRAFIAEE GWLLVALDYS QIELRVLAHL
701  SGDENLIRVF QEGRDIHTET ASWMFGVPRE AVDPLMRRAA KTINFGVLYG
751  MSAHRLSQEL AIPYEEAQAF IERYFQSFPK VRAWIEKTLE EGRRRGYVET
801  LFGRRRYVPD LEARVKSVRE AAERMAFNMP VQGTAADLMK LAMVKLFPRL
851  EEMGARMLLQ VHDELVLEAP KERAEAVARL AKEVMEGVYP LAVPLEVEVG
901  IGEDWLSAKE
```

Figure 3/1
SEQ ID No.: 3

DNA sequence:
```
   1 ATGAGGGGCT CGCATCACCA TCACCATCAC GCTGCTGACG ATGACGATAA
  51 AATGAGGGGC ATGCTACCGC TATTTGAGCC AAGGGCCGG  GTCCTCCTGG
 101 TCGACGGCCA CCACCTGGCC TACCGCACCT TCCACGCCCT GAAGGGCCTC
 151 ACCACCAGCC GGGGGGAGCC GGTGCAGGCG GTCTACGGCT TCGCCAAGAG
 201 CCTCCTCAAG GCCCTCAAGG AGGACGGGGA CGCGGTGATC GTGGTCTTTG
 251 ACGCCAAGGC CCCCTCCTTC CGCCACGAGG CCTACGGGGG GTACAAGGCG
 301 GGCCGGGCCC CCACGCCGGA GGACTTTCCC CGGCAACTCG CCCTCATCAA
 351 GGAGCTGGTG GACCTCCTGG GCTGGCGCG  CCTCGAGGTC CCGGGCTACG
 401 AGGCGGACGA CGTCCTGGCC AGCCTGGCCA AGAAGGCGGA AAAGGAGGGC
 451 TACGAGGTCC GCATCCTCAC CGCCGACAAA GACCTTTACC AGCTCCTTTC
 501 CGACCGCATC CACGTCCTCC ACCCCGAGGG GTACCTCATC ACCCCGGCCT
 551 GGCTTTGGGA AAAGTACGGC CTGAGGCCCG ACCAGTGGGC CGACTACCGG
 601 GCCCTGACCG GGGACGAGTC CGACAACCTT CCCGGGGTCA AGGGCATCGG
 651 GGAGAAGACG GCGAGGAAGC TTCTGGAGGA GTGGGGGAGC CTGGAAGCCC
 701 TCCTCAAGAA CCTGGACCGG CTGAAGCCCG CCATCCGGGA GAAGATCCTG
 751 GCCCACATGG ACGATCTGAA GCTCTCCTGG GACCTGGCCA AGGTGCGCAC
 801 CGACCTGCCC CTGGAGGTGG ACTTCGCCAA AAGGCGGGAG CCCGACCGGG
 851 AGAGGCTTAG GGCCTTTCTG GAGAGGCTTG AGTTTGGCAG CCTCCTCCAC
 901 GAGTTCGGCC TTCTGGAAAG CCCCCCCGTT GGATACAGAA TAGTGAAAGA
 951 CCTGGTGGAA TTTGAAAAAC TCATAGAGAA ACTGAGAGAA TCCCCTTCGT
1001 TCGCCATAGA TCTTGAGACG TCTTCCCTCG ATCCTTTCGA CTGCGACATT
1051 GTCGGTATCT CTGTGTCTTT CAAACCAAAG GAAGCGTACT ACATACCACT
1101 CCATCATAGA AACGCCCAGA ACCTGGATGA AAAGAAGTT  CTGAAAAAGC
1151 TAAAAGAAAT CCTGGAGGAC CCCGGAGCAA AGATCGTTGG TCAGAATTTG
1201 AAATTCGATT ACAAGGTGTT GATGGTAAAG GGTGTTGAAC CTGTCCCTCC
1251 TCACTTCGAC ACGATGATAG CGGCTTACCT TCTTGAGCCG AACGAAAAGA
1301 AGTTCAATCT GGACGATCTC GCATTGAAAT TTCTTGGATA CAAAATGACC
1351 TCTTACCAGG AACTCATGTC CTTCTCTTCT CCGCTGTTTG GTTTCAGTTT
1401 TGCCGATGTT CCTGTAGAAA AAGCAGCGAA CTATTCCTGT GAAGATGCCG
1451 ACATCACCTA CAGACTCTAC AAGATCCTGA GCTTAAAACT CCACGAGGAG
1501 AGGCTCCTTT GGCTTTACCG GGAGGTGGAG AGGCCCCTTT CCGCTGTCCT
1551 GGCCCACATG GAGGCCACGG GGGTGCGCCT GGACGTGGCC TATCTCAGGG
1601 CCTTGTCCCT GGAGGTGGCC GAGGAGATCG CCCGCCTCGA GGCCGAGGTC
1651 TTCCGCCTGG CCGGCCACCC CTTCAACCTC AACTCCCGGG ACCAGCTGGA
1701 AAGGGTCCTC TTTGACGAGC TAGGGCTTCC CGCCATCGGC AAGACGGAGA
1751 AGACCGGCAA GCGCTCCACC AGCGCCGCCG TCCTGGAGGC CCTCCGCGAG
1801 GCCCACCCCA TCGTGGAGAA GATCCTGCAG TACCGGGAGC TCACCAAGCT
1851  GAAGAGCACC TACATTGACC CCTTGCCGGA CCTCATCCAC CCCAGGACGG
1901 GCCGCCTCCA CACCCGCTTC AACCAGACGG CCACGGCCAC GGGCAGGCTA
1951 AGTAGCTCCG ATCCCAACCT CCAGAACATC CCCGTCCGCA CCCCGCTTGG
2001 GCAGAGGATC CGCCGGGCCT TCATCGCCGA GGAGGGGTGG CTATTGGTGG
2051 CCCTGGACTA TAGCCAGATA GAGCTCAGGG TGCTGGCCCA CCTCTCCGGC
2101 GACGAGAACC TGATCCGGGT CTTCCAGGAG GGGCGGGACA TCCACACGGA
2151 GACCGCCAGC TGGATGTTCG GCGTCCCCCG GGAGGCCGTG GACCCCCTGA
2201 TGCGCCGGGC GGCCAAGACC ATCAACTTCG GGGTCCTCTA CGGCATGTCG
2251 GCCCACCGCC TCTCCCAGGA GCTAGCCATC CCTTACGAGG AGGCCCAGGC
2301 CTTCATTGAG CGCTACTTTC AGAGCTTCCC CAAGGTGCGG GCCTGGATTG
2351 AGAAGACCCT GGAGGAGGGC AGGAGGCGGG GGTACGTGGA GACCCTCTTC
2401 GGCCGCCGCC GCTACGTGCC AGACCTAGAG GCCCGGGTGA AGAGCGTGCG
2451 GGAGGCGGCC GAGCGCATGG CCTTCAACAT GCCCGTCCAG GGCACCGCCG
2501 CCGACCTCAT GAAGCTGGCT ATGGTGAAGC TCTTCCCCAG GCTGGAGGAA
```

Figure 3/2
SEQ ID No.: 3

```
2551 ATGGGGGCCA GGATGCTCCT TCAGGTCCAC GACGAGCTGG TCCTCGAGGC
2601 CCCAAAAGAG AGGGCGGAGG CCGTGGCCCG GCTGGCCAAG GAGGTCATGG
2651 AGGGGGTGTA TCCCCTGGCC GTGCCCCTGG AGGTGGAGGT GGGGATAGGG
2701 GAGGACTGGC TCTCCGCCAA GGAGTGA
```

SEQ ID No.: 9 amino acid sequence:
```
  1   MRGSHHHHHH AADDDDKMRG MLPLFEPKGR VLLVDGHHLA YRTFHALKGL
 51   TTSRGEPVQA VYGFAKSLLK ALKEDGDAVI VVFDAKAPSF RHEAYGGYKA
101   GRAPTPEDFP RQLALIKELV DLLGLARLEV PGYEADDVLA SLAKKAEKEG
151   YEVRILTADK DLYQLLSDRI HVLHPEGYLI TPAWLWEKYG LRPDQWADYR
201   ALTGDESDNL PGVKGIGEKT ARKLLEEWGS LEALLKNLDR LKPAIREKIL
251   AHMDDLKLSW DLAKVRTDLP LEVDFAKRRE PDRERLRAFL ERLEFGSLLH
301   EFGLLESPPV GYRIVKDLVE FEKLIEKLRE SPSFAIDLET SSLDPFDCDI
351   VGISVSFKPK EAYYIPLHHR NAQNLDEKEV LKKLKEILED PGAKIVGQNL
401   KFDYKVLMVK GVEPVPPHFD TMIAAYLLEP NEKKFNLDDL ALKFLGYKMT
451   SYQELMSFSS PLFGFSFADV PVEKAANYSC EDADITYRLY KILSLKLHEE
501   RLLWLYREVE RPLSAVLAHM EATGVRLDVA YLRALSLEVA EEIARLEAEV
551   FRLAGHPFNL NSRDQLERVL FDELGLPAIG KTEKTGKRST SAAVLEALRE
601   AHPIVEKILQ YRELTKLKST YIDPLPDLIH PRTGRLHTRF NQTATATGRL
651   SSSDPNLQNI PVRTPLGQRI RRAFIAEEGW LLVALDYSQI ELRVLAHLSG
701   DENLIRVFQE GRDIHTETAS WMFGVPREAV DPLMRRAAKT INFGVLYGMS
751   AHRLSQELAI PYEEAQAFIE RYFQSFPKVR AWIEKTLEEG RRRGYVETLF
801   GRRRYVPDLE ARVKSVREAA ERMAFNMPVQ GTAADLMKLA MVKLFPRLEE
851   MGARMLLQVH DELVLEAPKE RAEAVARLAK EVMEGVYPLA VPLEVEVGIG
901   EDWLSAKE
```

Figure 4/1
SEQ ID No.: 4

DNA sequence:
```
   1 ATGAGGGGCT CGCATCACCA TCACCATCAC GCTGCTGACG ATGACGATAA
  51 AATGAGGGGC ATGCTACCGC TATTTGAGCC CAAGGGCCGG GTCCTCCTGG
 101 TCGACGGCCA CCACCTGGCC TACCGCACCT TCCACGCCCT GAAGGGCCTC
 151 ACCACCAGCC GGGGGGAGCC GGTGCAGGCG GTCTACGGCT TCGCCAAGAG
 201 CCTCCTCAAG GCCCTCAAGG AGGACGGGGA CGCGGTGATC GTGGTCTTTG
 251 ACGCCAAGGC CCCCTCCTTC CGCCACGAGG CCTACGGGGG GTACAAGGCG
 301 GGCCGGGCCC CCACGCCGGA GGACTTTCCC CGGCAACTCG CCCTCATCAA
 351 GGAGCTGGTG GACCTCCTGG GGCTGGCGCG CCTCGAGGTC CCGGGCTACG
 401 AGGCGGACGA CGTCCTGGCC AGCCTGGCCA AGAAGGCGGA AAAGGAGGGC
 451 TACGAGGTCC GCATCCTCAC CGCCGACAAA GACCTTTACC AGCTCCTTTC
 501 CGACCGCATC CACGTCCTCC ACCCCGAGGG GTACCTCATC ACCCCGGCCT
 551 GGCTTTGGGA AAAGTACGGC CTGAGGCCCG ACCAGTGGGC CGACTACCGG
 601 GCCCTGACCG GGGACGAGTC CGACAACCTT CCCGGGGTCA AGGGCATCGG
 651 GGAGAAGACG GCGAGGAAGC TTCTGGAGGA GTGGGGGAGC CTGGAAGCCC
 701 TCCTCAAGAA CCTGGACCGG CTGAAGCCCG CCATCCGGGA GAAGATCCTG
 751 GCCCACATGG ACGATCTGAA GCTCTCCTGG GACCTGGCCA AGGTGCGCAC
 801 CGACCTGCCC CTGGAGGTGG ACTTCGCCAA AAGGCGGGAG CCCGACCGGG
 851 AGAGGCTTAG GGCCTTTCTG GAGAGGCTTG AGTTTGGCAG CCTCCTCCAC
 901 GAGTTCGGCC TTCTGGAAAG CCCCCCCGTT GGATACAGAA TAGTGAAAGA
 951 CCTGGTGGAA TTTGAAAAAC TCATAGAGAA ACTGAGAGAA TCCCCTTCGT
1001 TCGCCATAGA TCTTGAGACG TCTTCCCTCG ATCCTTTCGA CTGCGACATT
1051 GTCGGTATCT CTGTGTCTTT CAAACCAAAG GAAGCGTACT ACATACCACT
1101 CCATCATAGA AACGCCCAGA ACCTGGATGA AAAGAAGTT CTGAAAAAGC
1151 TAAAAGAAAT CCTGGAGGAC CCCGGAGCAA AGATCGTTGG TCAGAATTTG
1201 AAATTCGATT ACAAGGTGTT GATGGTAAAG GGTGTTGAAC CTGTCCCTCC
1251 TCACTTCGAC ACGATGATAG CGGCTTACCT TCTTGAGCCG AACGAAAAGA
1301 AGTTCAATCT GGACGATCTC GCATTGAAAT TTCTTGGATA CAAAATGACC
1351 TCTTACCAGG AACTCATGTC CTTCTCTTCT CCGCTGTTTG GTTTCAGTTT
1401 TGCCGATGTT CCTGTAGAAA AAGCAGCGAA CTATTCCTGT GAAGATGCAG
1451 ACATCACCTA CAGACTCTAC AAGATCCTGA GCTTAAAACT CCACGAGGCA
1501 GATCTGGAGA ACGTGTTCTA CAAGATAGAA ATGCCTCTTG TGAGCGTGCT
1551 TGCACGGATG GAACTGAACG GTGTGCGCCT GGACGTGGCC TATCTCAGGG
1601 CCTTGTCCCT GGAGGTGGCC GAGGAGATCG CCCGCCTCGA GGCCGAGGTC
1651 TTCCGCCTGG CCGGCCACCC CTTCAACCTC AACTCCCGGG ACCAGCTGGA
1701 AAGGGTCCTC TTTGACGAGC TAGGGCTTCC CGCCATCGGC AAGACGGAGA
1751 AGACCGGCAA GCGCTCTACC AGCGCCGCCG TCCTGGAGGC CCTCCGCGAG
1801 GCCCACCCCA TCGTGGAGAA GATCCTGCAG TACCGGGAGC TCACCAAGCT
1851 GAAGAGCACC TACATTGACC CCTTGCCGGA CCTCATCCAC CCCAGGACGG
1901 GCCGCCTCCA CACCCGCTTC AACCAGACGG CCACGGCCAC GGGCAGGCTA
1951 AGTAGCTCCG ATCCCAACCT CCAGAACATC CCCGTCCGCA CCCCGCTTGG
2001 GCAGAGGATC CGCCGGGCCT TCATCGCCGA GGAGGGGTGG CTATTGGTGG
2051 CCCTGGACTA TAGCCAGATA GAGCTCAGGG TGCTGGCCCA CCTCTCCGGC
2101 GACGAGAACC TGATCCGGGT CTTCCAGGAG GGGCGGGACA TCCACACGGA
2151 GACCGCCAGC TGGATGTTCG CGTCCCCCGG GAGGCCGTG GACCCCCTGA
2201 TGCGCCGGGC GGCCAAGACC ATCAACTTCG GGGTCCTCTA CGGCATGTCG
2251 GCCCACCGCC TCTCCCAGGA GCTAGCCATC CCTTACGAGG AGGCCCAGGC
2301 CTTCATTGAG CGCTACTTTC AGAGCTTCCC CAAGGTGCGG GCCTGGATTG
2351 AGAAGACCCT GGAGGAGGGC AGGAGGCGGG GGTACGTGGA GACCCTCTTC
2401 GGCCGCCGCC GCTACGTGCC AGACCTAGAG GCCCGGGTGA AGAGCGTGCG
2451 GGAGGCGGCC GAGCGCATGG CCTTCAACAT GCCCGTCCAG GGCACCGCCG
2501 CCGACCTCAT GAAGCTGGCT ATGGTGAAGC TCTTCCCCAG GCTGGAGGAA
```

Figure 4/2
SEQ ID No.: 4

```
2551 ATGGGGGCCA GGATGCTCCT TCAGGTCCAC GACGAGCTGG TCCTCGAGGC
2601 CCCAAAAGAG AGGGCGGAGG CCGTGGCCCG GCTGGCCAAG GAGGTCATGG
2651 AGGGGGTGTA TCCCCTGGCC GTGCCCCTGG AGGTGGAGGT GGGGATAGGG
2701 GAGGACTGGC TCTCCGCCAA GGAGTGA
```

SEQ ID NO.: 10 amino acid sequence:

```
  1  MRGSHHHHHH AADDDDKMRG MLPLFEPKGR VLLVDGHHLA YRTFHALKGL
 51  TTSRGEPVQA VYGFAKSLLK ALKEDGDAVI VVFDAKAPSF RHEAYGGYKA
101  GRAPTPEDFP RQLALIKELV DLLGLARLEV PGYEADDVLA SLAKKAEKEG
151  YEVRILTADK DLYQLLSDRI HVLHPEGYLI TPAWLWEKYG LRPDQWADYR
201  ALTGDESDNL PGVKGIGEKT ARKLLEEWGS LEALLKNLDR LKPAIREKIL
251  AHMDDLKLSW DLAKVRTDLP LEVDFAKRRE PDRERLRAFL ERLEFGSLLH
301  EFGLLESPPV GYRIVKDLVE FEKLIEKLRE SPSFAIDLET SSLDPFDCDI
351  VGISVSFKPK EAYYIPLHHR NAQNLDEKEV LKKLKEILED PGAKIVGQNL
401  KFDYKVLMVK GVEPVPPHFD TMIAAYLLEP NEKKFNLDDL ALKFLGYKMT
451  SYQELMSFSS PLFGFSFADV PVEKAANYSC EDADITYRLY KILSLKLHEA
501  DLENVFYKIE MPLVSVLARM ELNGVRLDVA YLRALSLEVA EEIARLEAEV
551  FRLAGHPFNL NSRDQLERVL FDELGLPAIG KTEKTGKRST SAAVLEALRE
601  AHPIVEKILQ YRELTKLKST YIDPLPDLIH PRTGRLHTRF NQTATATGRL
651  SSSDPNLQNI PVRTPLGQRI RRAFIAEEGW LLVALDYSQI ELRVLAHLSG
701  DENLIRVFQE GRDIHTETAS WMFGVPREAV DPLMRRAAKT INFGVLYGMS
751  AHRLSQELAI PYEEAQAFIE RYFQSFPKVR AWIEKTLEEG RRRGYVETLF
801  GRRRYVPDLE ARVKSVREAA ERMAFNMPVQ GTAADLMKLA MVKLFPRLEE
851  MGARMLLQVH DELVLEAPKE RAEAVARLAK EVMEGVYPLA VPLEVEVGIG
901  EDWLSAKE
```

Figure 5/1
SEQ ID No.: 5

DNA sequence:

```
   1 ATGAGGGGCT CGCATCACCA TCACCATCAC GCTGCTGACG ATGACGATAA
  51 AATGAGGGGC ATGCTACCGC TATTTGAGCC CAAGGGCCGG GTCCTCCTGG
 101 TCGACGGCCA CCACCTGGCC TACCGCACCT TCCACGCCCT GAAGGGCCTC
 151 ACCACCAGCC GGGGGGAGCC GGTGCAGGCG GTCTACGGCT TCGCCAAGAG
 201 CCTCCTCAAG GCCCTCAAGG AGGACGGGGA CGCGGTGATC GTGGTCTTTG
 251 ACGCCAAGGC CCCCTCCTTC CGCCACGAGG CCTACGGGGG GTACAAGGCG
 301 GGCCGGGCCC CCACGCCGGA GGACTTTCCC CGGCAACTCG CCCTCATCAA
 351 GGAGCTGGTG GACCTCCTGG GGCTGGCGCG CCTCGAGGTC CCGGGCTACG
 401 AGGCGGACGA CGTCCTGGCC AGCCTGGCCA AGAAGGCGGA AAAGGAGGGC
 451 TACGAGGTCC GCATCCTCAC CGCCGACAAA GACCTTTACC AGCTCCTTTC
 501 CGACCGCATC CACGTCCTCC ACCCCGAGGG GTACCTCATC ACCCCGGCCT
 551 GGCTTTGGGA AAAGTACGGC CTGAGGCCCG ACCAGTGGGC CGACTACCGG
 601 GCCCTGACCG GGGACGAGTC CGACAACCTT CCCGGGGTCA AGGGCATCGG
 651 GGAGAAGACG GCGAGGAAGC TTCTGGAGGA GTGGGGGAGC CTGGAAGCCC
 701 TCCTCAAGAA CCTGGACCGG CTGAAGCCCG CCATCCGGGA GAAGATCCTG
 751 GCCCACATGG ACGATCTGAA GCTCTCCTGG GACCTGGCCA AGGTGCGCAC
 801 CGACCTGCCC CTGGAGGTGG ACTTCGCCAA AAGGCGGGAG CCCGACCGGG
 851 AGAGGCTTAG GGCCTTTCTG GAGAGGCTTG AGTTTGGCAG CCTCCTCCAC
 901 GAGTTCGGCC TTCTGGAAAG CCCCCATCCA GCAGTTGTGG ACATCTTCGA
 951 ATACGATATT CCATTTGCAA AGAGATACCT CATCGACAAA GGCCTAATAC
1001 CAATGGAGGG GGAAGAAGAG CTAAAGATTC TTGCCTTCGA TATAGAAACC
1051 CTCTATCACG AAGGAGAAGA GTTTGGAAAA GGCCCAATTA TAATGATTAG
1101 TTATGCAGAT GAAAATGAAG CAAAGGTGAT TACTTGGAAA AACATAGATC
1151 TTCCATACGT TGAGGTTGTA TCAAGCGAGA GAGAGATGAT AAAGAGATTT
1201 CTCAGGATTA TCAGGGAGAA GGATCCTGAC ATTATAGTTA CTTATAATGG
1251 AGACTCATTC GACTTCCCAT ATTTAGCGAA AAGGGCAGAA AAACTTGGGA
1301 TTAAATTAAC CATTGGAAGA GATGGAAGCG AGCCCAAGAT GCAGAGAATA
1351 GGCGATATGA CGGCTGTAGA AGTCAAGGGA AGAATACATT TCGACTTGTA
1401 TCATGTAATA ACAAGGACAA TAAATCTCCC AACATACACA CTAGAGGCTG
1451 TATATGAAGC AATTTTTGGA AAGCCAAAGG AGAAGGTATA CGCCGACGAG
1501 ATAGCAAAAG CCTGGGAAAG TGGAGAGAAC CTTGAGAGAG TTGCCAAATA
1551 CTCGATGGAA GATGCAAAGG CAACTTATGA ACTCGGGAAA GAATTCCTTC
1601 CAATGGAAAT TCAGCTTTCA GAGAGGCTCC TTTGGCTTTA CCGGAGGTG
1651 GAGAGGCCCC TTTCCGCTGT CCTGGCCCAC ATGGAGGCCA CGGGGGTGCG
1701 CCTGGACGTG GCCTATCTCA GGGCCTTGTC CCTGGAGGTG GCCGAGGAGA
1751 TCGCCCGCCT CGAGGCCGAG GTCTTCCGCC TGGCCGGCCA CCCCTTCAAC
1801 CTCAACTCCC GGGACCAGCT GGAAAGGGTC CTCTTTGACG AGCTAGGGCT
1851 TCCCGCCATC GGCAAGACGG AGAAGACCGG CAAGCGCTCC ACCAGCGCCG
1901 CCGTCCTGGA GGCCCTCCGC GAGGCCCACC CCATCGTGGA GAAGATCCTG
1951 CAGTACCGGG AGCTCACCAA GCTGAAGAGC ACCTACATTG ACCCCTTGCC
2001 GGACCTCATC CACCCCAGGA CGGGCCGCCT CCACACCCGC TTCAACCAGA
2051 CGGCCACGGC CACGGGCAGG CTAAGTAGCT CCGATCCCAA CCTCCAGAAC
2101 ATCCCCGTCC GCACCCCGCT GGGCAGAGG ATCCGCCGGG CCTTCATCGC
2151 CGAGGAGGGG TGGCTATTGG TGGCCCTGGA CTATAGCCAG ATAGAGCTCA
2201 GGGTGCTGGC CCACCTCTCC GGCGACGAGA ACCTGATCCG GGTCTTCCAG
2251 GAGGGCGGG ACATCCACAC GGAGACCGCC AGCTGGATGT TCGGCGTCCC
2301 CCGGGAGGCC GTGGACCCCC TGATGCGCCG GGCGGCCAAG ACCATCAACT
2351 TCGGGGTCCT CTACGGCATG TCGGCCCACC GCCTCTCCCA GGAGCTAGCC
2401 ATCCCTTACG AGGAGGCCCA GGCCTTCATT GAGCGCTACT TTCAGAGCTT
2451 CCCCAAGGTG CGGGCCTGGA TTGAGAAGAC CCTGGAGGAG GCAGGAGGC
2501 GGGGGTACGT GGAGACCCTC TTCGGCCGCC GCCGCTACGT GCCAGACCTA
```

Figure 5/2
SEQ ID No.: 5

```
2551 GAGGCCCGGG TGAAGAGCGT GCGGGAGGCG GCCGAGCGCA TGGCCTTCAA
2601 CATGCCCGTC CAGGGCACCG CCGCCGACCT CATGAAGCTG GCTATGGTGA
2651 AGCTCTTCCC CAGGCTGGAG GAAATGGGGG CCAGGATGCT CCTTCAGGTC
2701 CACGACGAGC TGGTCCTCGA GGCCCCAAAA GAGAGGGCGG AGGCCGTGGC
2751 CCGGCTGGCC AAGGAGGTCA TGGAGGGGGT GTATCCCCTG GCCGTGCCCC
2801 TGGAGGTGGA GGTGGGGATA GGGGAGGACT GGCTCTCCGC CAAGGAGTGA
```

SEQ ID No.: 11 amino acid sequence:
```
  1  MRGSHHHHHH AADDDDKMRG MLPLFEPKGR VLLVDGHHLA YRTFHALKGL
 51  TTSRGEPVQA VYGFAKSLLK ALKEDGDAVI VVFDAKAPSF RHEAYGGYKA
101  GRAPTPEDFP RQLALIKELV DLLGLARLEV PGYEADDVLA SLAKKAEKEG
151  YEVRILTADK DLYQLLSDRI HVLHPEGYLI TPAWLWEKYG LRPDQWADYR
201  ALTGDESDNL PGVKGIGEKT ARKLLEEWGS LEALLKNLDR LKPAIREKIL
251  AHMDDLKLSW DLAKVRTDLP LEVDFAKRRE PDRERLRAFL ERLEFGSLLH
301  EFGLLESPHP AVVDIFEYDI PFAKRYLIDK GLIPMEGEEE LKILAFDIET
351  LYHEGEEFGK GPIIMISYAD ENEAKVITWK NIDLPYVEVV SSEREMIKRF
401  LRIIREKDPD IIVTYNGDSF DFPYLAKRAE KLGIKLTIGR DGSEPKMQRI
451  GDMTAVEVKG RIHFDLYHVI TRTINLPTYT LEAVYEAIFG KPKEKVYADE
501  IAKAWESGEN LERVAKYSME DAKATYELGK EFLPMEIQLS ERLLWLYREV
551  ERPLSAVLAH MEATGVRLDV AYLRALSLEV AEEIARLEAE VFRLAGHPFN
601  LNSRDQLERV LFDELGLPAI GKTEKTGKRS TSAAVLEALR EAHPIVEKIL
651  QYRELTKLKS TYIDPLPDLI HPRTGRLHTR FNQTATATGR LSSSDPNLQN
701  IPVRTPLGQR IRRAFIAEEG WLLVALDYSQ IELRVLAHLS GDENLIRVFQ
751  EGRDIHTETA SWMFGVPREA VDPLMRRAAK TINFGVLYGM SAHRLSQELA
801  IPYEEAQAFI ERYFQSFPKV RAWIEKTLEE GRRRGYVETL FGRRRYVPDL
851  EARVKSVREA AERMAFNMPV QGTAADLMKL AMVKLFPRLE EMGARMLLQV
901  HDELVLEAPK ERAEAVARLA KEVMEGVYPL AVPLEVEVGI GEDWLSAKE*
```

Figure 6/1
SEQ ID No.: 6

DNA sequence:

```
   1 ATGAGGGGCT CGCATCACCA TCACCATCAC GCTGCTGACG ATGACGATAA
  51 AATGAGGGGC ATGCTACCGC TATTTGAGCC CAAGGGCCGG GTCCTCCTGG
 101 TCGACGGCCA CCACCTGGCC TACCGCACCT TCCACGCCCT GAAGGGCCTC
 151 ACCACCAGCC GGGGGGAGCC GGTGCAGGCG GTCTACGGCT TCGCCAAGAG
 201 CCTCCTCAAG GCCCTCAAGG AGGACGGGGA CGCGGTGATC GTGGTCTTTG
 251 ACGCCAAGGC CCCCTCCTTC CGCCACGAGG CCTACGGGGG GTACAAGGCG
 301 GGCCGGGCCC CCACGCCGGA GGACTTTCCC CGGCAACTCG CCCTCATCAA
 351 GGAGCTGGTG GACCTCCTGG GCTGGCGCG CCTCGAGGTC CCGGGCTACG
 401 AGGCGGACGA CGTCCTGGCC AGCCTGGCCA AGAAGGCGGA AAAGGAGGGC
 451 TACGAGGTCC GCATCCTCAC CGCCGACAAA GACCTTTACC AGCTCCTTTC
 501 CGACCGCATC CACGTCCTCC ACCCCGAGGG GTACCTCATC ACCCCGGCCT
 551 GGCTTTGGGA AAAGTACGGC CTGAGGCCCG ACCAGTGGGC CGACTACCGG
 601 GCCCTGACCG GGACGAGTC CGACAACCTT CCCGGGGTCA GGGCATCGG
 651 GGAGAAGACG GCGAGGAAGC TTCTGGAGGA GTGGGGGAGC CTGGAAGCCC
 701 TCCTCAAGAA CCTGGACCGG CTGAAGCCCG CCATCCGGGA GAAGATCCTG
 751 GCCCACATGG ACGATCTGAA GCTCTCCTGG GACCTGGCCA AGGTGCGCAC
 801 CGACCTGCCC CTGGAGGTGG ACTTCGCCAA AAGGCGGGAG CCCGACCGGG
 851 AGAGGCTTAG GGCCTTTCTG GAGAGGCTTG AGTTTGGCAG CCTCCTCCAC
 901 GAGTTCGGCC TTCTGGAAAG CCCCGTTAGA GAACATCCAG CAGTTGTGGA
 951 CATCTTCGAA TACGATATTC CATTTGCAAA GAGATACCTC ATCGACAAAG
1001 GCCTAATACC AATGGAGGGG GAAGAAGAGC TAAAGATTCT TGCCTTCGAT
1051 ATAGAAACCC TCTATCACGA AGGAGAAGAG TTTGGAAAAG GCCAATTAT
1101 AATGATTAGT TATGCAGATG AAAATGAAGC AAAGGTGATT ACTTGGAAAA
1151 ACATAGATCT TCCATACGTT GAGGTTGTAT CAAGCGAGAG AGATGATA
1201 AAGAGATTTC TCAGGATTAT CAGGGAGAAG GATCCTGACA TTATAGTTAC
1251 TTATAATGGA GACTCATTCG ACTTCCCATA TTTAGCGAAA AGGGCAGAAA
1301 AACTTGGGAT TAAATTAACC ATTGGAAGAG ATGGAAGCGA GCCCAAGATG
1351 CAGAGAATAG GCGATATGAC GGCTGTAGAA GTCAAGGGAA GAATACATTT
1401 CGACTTGTAT CATGTAATAA CAAGGACAAT AAATCTCCCA ACATACACAC
1451 TAGAGGCTGT ATATGAAGCA ATTTTTGGAA AGCCAAAGGA GAAGGTATAC
1501 GCCGACGAGA TAGCAAAAGC CTGGGAAAGT GGAGAGAACC TTGAGAGAGT
1551 TGCCAAATAC TCGATGGAAG ATGCAAAGGC AACTTATGAA CTCGGGAAAG
1601 AATTCCTTCC AATGGAAATT CAGCTTTCAA GATTAGTTGG ACAACCTTTA
1651 TGGGATGTTT CAAGGTCAAG CACAGGGAAC CTTGTAGAGT GGTTCTTACT
1701 TAGGAAAGCC TACGAAAGAA ACGAAGTAGC TCCAAACAAG CCAAGTGAAG
1751 AGGAGTATCA AAGAAGGCTC AGGGAGAGCT ACACAGGTGG ATTCGTGCGC
1801 CTGGACGTGG CCTATCTCAG GGCCTTGTCC CTGGAGGTGG CCGAGGAGAT
1851 CGCCCGCCTC GAGGCCGAGG TCTTCCGCCT GGCCGGCCAC CCCTTCAACC
1901 TCAACTCCCG GGACCAGCTG GAAAGGGTCC TCTTTGACGA GCTAGGGCTT
1951 CCCGCCATCG GCAAGACGGA GAAGACCGGC AAGCGCTCCA CCAGCGCCGC
2001 CGTCCTGGAG GCCCTCCGCG AGGCCCACCC CATCGTGGAG AAGATCCTGC
2051 AGTACCGGGA GCTCACCAAG CTGAAGAGCA CCTACATTGA CCCCTTGCCG
2101 GACCTCATCC ACCCCAGGAC GGGCCGCCTC CACACCCGCT TCAACCAGAC
2151 GGCCACGGCC ACGGGCAGGC TAAGTAGCTC CGATCCCAAC CTCCAGAACA
2201 TCCCCGTCCG CACCCCGCTT GGGCAGAGGA TCCGCCGGGC CTTCATCGCC
2251 GAGGAGGGGT GGCTATTGGT GGCCCTGGAC TATAGCCAGA TAGAGCTCAG
2301 GGTGCTGGCC CACCTCTCCG GCGACGAGAA CCTGATCCGG GTCTTCCAGG
2351 AGGGGCGGGA CATCCACACG GAGACCGCCA GCTGGATGTT CGGCGTCCCC
2401 CGGGAGGCCG TGGACCCCCT GATGCGCCGG GCGGCCAAGA CCATCAACTT
2451 CGGGGTCCTC TACGGCATGT CGGCCCACCG CCTCTCCCAG GAGCTAGCCA
2501 TCCCTTACGA GGAGGCCCAG GCCTTCATTG AGCGCTACTT TCAGAGCTTC
```

Figure 6/2
SEQ ID No.: 6

```
2551 CCCAAGGTGC GGGCCTGGAT TGAGAAGACC CTGGAGGAGG GCAGGAGGCG
2601 GGGGTACGTG GAGACCCTCT TCGGCCGCCG CCGCTACGTG CCAGACCTAG
2651 AGGCCCGGGT GAAGAGCGTG CGGGAGGCGG CCGAGCGCAT GGCCTTCAAC
2701 ATGCCCGTCC AGGGCACCGC CGCCGACCTC ATGAAGCTGG CTATGGTGAA
2751 GCTCTTCCCC AGGCTGGAGG AAATGGGGGC AGGATGCTC CTTCAGGTCC
2801 ACGACGAGCT GGTCCTCGAG GCCCCAAAAG AGAGGGCGGA GGCCGTGGCC
2851 CGGCTGGCCA AGGAGGTCAT GGAGGGGGTG TATCCCCTGG CCGTGCCCCT
2901 GGAGGTGGAG GTGGGGATAG GGGAGGACTG GCTCTCCGCC AAGGAGTGA
```

SEQ ID No.: 12 amino acid sequence:
```
  1 MRGSHHHHHH AADDDDKMRG MLPLFEPKGR VLLVDGHHLA YRTFHALKGL
 51 TTSRGEPVQA VYGFAKSLLK ALKEDGDAVI VVFDAKAPSF RHEAYGGYKA
101 GRAPTPEDFP RQLALIKELV DLLGLARLEV PGYEADDVLA SLAKKAEKEG
151 YEVRILTADK DLYQLLSDRI HVLHPEGYLI TPAWLWEKYG LRPDQWADYR
201 ALTGDESDNL PGVKGIGEKT ARKLLEEWGS LEALLKNLDR LKPAIREKIL
251 AHMDDLKLSW DLAKVRTDLP LEVDFAKRRE PDRERLRAFL ERLEFGSLLH
301 EFGLLESPVR EHPAVVDIFE YDIPFAKRYL IDKGLIPMEG EEELKILAFD
351 IETLYHEGEE FGKGPIIMIS YADENEAKVI TWKNIDLPYV EVVSSEREMI
401 KRFLRIIREK DPDIIVTYNG DSFDFPYLAK RAEKLGIKLT IGRDGSEPKM
451 QRIGDMTAVE VKGRIHFDLY HVITRTINLP TYTLEAVYEA IFGKPKEKVY
501 ADEIAKAWES GENLERVAKY SMEDAKATYE LGKEFLPMEI QLSRLVGQPL
551 WDVSRSSTGN LVEWFLLRKA YERNEVAPNK PSEEEYQRRL RESYTGGFVR
601 LDVAYLRALS LEVAEEIARL EAEVFRLAGH PFNLNSRDQL ERVLFDELGL
651 PAIGKTEKTG KRSTSAAVLE ALREAHPIVE KILQYRELTK LKSTYIDPLP
701 DLIHPRTGRL HTRFNQTATA TGRLSSSDPN LQNIPVRTPL GQRIRRAFIA
751 EEGWLLVALD YSQIELRVLA HLSGDENLIR VFQEGRDIHT ETASWMFGVP
801 REAVDPLMRR AAKTINFGVL YGMSAHRLSQ ELAIPYEEAQ AFIERYFQSF
851 PKVRAWIEKT LEEGRRRGYV ETLFGRRRYV PDLEARVKSV REAAERMAFN
901 MPVQGTAADL MKLAMVKLFP RLEEMGARML LQVHDELVLE APKERAEAVA
951 RLAKEVMEGV YPLAVPLEVE VGIGEDWLSA KE*
```

Fig. 17/1

SEQ ID No. 43
SEQ ID No. 44
SEQ ID No. 45
SEQ ID No. 46

```
chimen      -----MARLFLFDGTALAYRAYYALDRSLSTSTGIPTNATYGVARMLVRFIKDHIIVGKD
tne.rse     -----MARLFLFDGTALAYRAYYALDRSLSTSTGIPTNATYGVARMLVRFIKDHIIVGKD
ath.rse     ------MKLVIFDGNSILYRAFFALP-ELTTSNNIPTNAIYGFVNVILKYLEQ---EKPD
DPO1_ECOLI  MVQIPQNPLILVDGSSYLYRAYHAFP-PLTNSAGEPTGAMYGVLNMLRSLIMQ---YKPT
                 . **.  ***. *    *..* . **.* **   ..  .

chimera     YVAVAFDKKAATFRHKLLETYKAQRPKTPDLLIQQLPYIKKLVEALGMKVLEVEGYEADD
tne.rse     YVAVAFDKKAATFRHKLLETYKAQRPKTPDLLIQQLPYIKKLVEALGMKVLEVEGYEADD
ath.rse     YVAVAFDKRGREARKSEYEEYKANRKPMPDNLQVQIPYVREILYAFNIPIIEFEGYEADD
DPO1_ECOLI  HAAVVFDAKGKTFRDELFEHYKSHRPPMPDDLRAQIEPLHAMVKAMGLPLLAVSGVEADD
               .      *    * **. *   ** * *.   .. .. *  .. ..  * **** chimera     IIATLAVKGLPLFDEIFIVTGDKDMLQLVNEKIKVWRIVKGISD--LELYDAQKVKEKYG
chimera     IIATLAVKGLPLFDEIFIVTGDKDMLQLVNEKIKVWRIVKGISD--LELYDAQKVKEKYG
ath.rse     VIGSLVNQFKNTGLDIVIITGDRDTLQLLDKNVVVKIVSTKFDKTVEDLYTVENVKEKYG
DPO1_ECOLI  VIGTLAREAEKAGRPVLISTGDKDMAQLVTPNITLINTMTNTILG--PE----EVVNKYG
            .* .*          . * ***.*  **. . .               *    *** chimera     VEPQQIPDLLALTGDEIDNIPGVTGIGEKTAVQLLEKYKDLEDILNHVRELP-------Q
tne.rse     VEPQQIPDLLALTGDEIDNIPGVTGIGEKTAVQLLEKYKDLEDILNHVRELP-------Q
ath.rse     VWANQVPDYKALVGDQSDNIPGVKGIGEKSAQKLLEEYSSLEEIYQNLDKIK-------S
DPO1_ECOLI  VPPELIIDFLALMGDSSDNIPGVPGVGEKTAQALLQGLGGLDTLYAEPEKIAGLSFRGAK
            *    . *  ** ** ****** *.***.*   **    *..

chimera     KVRKALLRDRENAILSKKLAILETNVPIEINWEELRYQGYDREKLLPLLKELEFASIMKE
tne.rse     KVRKALLRDRENAILSKKLAILETNVPIEINWEELRYQGYDREKLLPLLKELEFASIMKE
ath.rse     SIREKLEAGKDMAFLSKRLATIVCDLPLNVKLEDLRTKEWNKERLYEILVQLEFKSIIKR
DPO1_ECOLI  TMAAKLEQNKEVAYLSYQLATIKTDVELELTCEQLEVQQPAAEELLGLFKKYEFKRWTAD
              .    * .. *   .       . .       * *   * *   ** chimera     LQLYEESEPVGYRIVK--------------------------.----DLVEFEKLIEKLRESP
tne.rse     LQLYEESEPVGYRIVK---------------------------*---DLVEFEKLIEKLRESP
ath.rse     LGLS---------------------------------------EVVQFEFVQQRTDIPD
DPO1-ECOLI  VEAGKWLQAKGAKPAAKPQETSVADEAPEVTATVISYDNYVTILDEETLKAWIAKLEKAP
                                                          .

chimera     SFAIDLETSSLDPFDCDIVGISVSFKPKEAYYIPLHHRNAQNLDEKE---VLKKLKEILE
tne.rse     SFAIDLETSSLDPFDCDIVGISVSFKPKEAYYIPLHHRNAQNLDEKE---VLKKLKEILE
ath.rse     VEQKELESISQIRSKE--IPLMFVQGEK-CFYLYDQESNTVFITSN------KLLIEEIL
DPO1_ECOLI  VFAFDTETDSLDNISANLVGLSFAIEPGVAAYIPVAHDYLDAPDQISRERALELLKPLLE
             . *. *           . .     .*.                  *    .
```

Fig. 17/2

```
chimera     DPGAKIVGQNLKFDYKVLMVKGVEPVPPHFDTMIAAYLLEPNEKKFNLDDLALKFLGYKM
tne.rse     DPGAKIVGQNLKFDYKVLMVKGVEPVPPHFDTMIAAYLLEPNEKKFNLDDLALKFLGYKM
ath.rse     KSDTVKIMYDLKNIFHQLNLEDTNNIKNCEDVMIASYVLDSTRSSYELETLFVSYLNTDI
DPO1_ECOLI  DEKALKVGQNLKYDRGILANYGIELRGIAFDTMLESYILNSVAGRHDMDSLAERWLKHKT
             .       **   *         *  *. .*.*        ..   *       * chimera     TSYQELMSFSSPLFGFSFADVPVEKAANYSCEDADITYRLYKILSLKLHEAD-LENVFYK
tne.rse     TSYQELMSFSSPLFGFSFADVPVEKAANYSCEDADITYRLYKILSLKLHEAD-LENVFYK
ath.rse     EAVKKDKKIVS--------------------VVLLKRLWDELLRLIDLNS-CQFLYEN
DPO1_ECOLI  ITFEEIAGKGKNQ--LTFNQIALEEAGRYAAEDADVTLQLHLKMWPDLQKHKGPLNVFEN
              .                             . .*    .      .         ..

chimera     IEMPLVSVLARMELNGVKVDRDALIQYTKEIENKILKLETQIYQIAGEWFNINSPKQLSY
tne.rse     IEMPLVSVLARMELNGVYVDTEFLKKLSEEYGKKLEELAEEIYRIAGEPFNINSPKQVSR
ath.rse     IERPLIPVLYEMEKTGFKVDRDALIQYTKEIENKILKLETQIYQIAGEWFNINSPKQLSY
DPO1-ECOLI  IEMPLVPVLSRIERNGVKIDPKVLHNHSEELTLRLAELEKKAHEIAGEEFNLSSTKQLQT
            ** **. **     .* .*    .*    *   .   *    ..   *   ****  **. * **.

chimera     ILFEKLKLPVIKKTKTG--YSTDAEVLEELFDKHEIVPLILDYRMYTKILTTYCQGLLQA
tne.rse     ILFEKLGIKPRGKTTKTGDYSTRIEVLEELAGEHEIIPLILEYRKIQKLKSTYIDALPKM
ath.rse     ILFEKLKLPVIKKTKTG--YSTDAEVLEELFDKHEIVPLILDYRMYTKILTTYCQGLLQA
DPO1_ECOLI  ILFEKQGIKPLKKTPGG-APSTSEEVLEELALDYPLPKVILEYRGLAKLKSTYTDKLPLM
            ***   .        **  .  ..**  *  . .**    * chimera     INPSSGRVHTTFIQTGTATGRLASSDPNLQNIPVKYDEGKLIRKVFVPEG-GHVLIDADY
tne.rse     VNPKTGRIHASFNQTGTATGRLSSSDPNLQNLPTKSEEGKEIRKAIVPQDPNWWIVSADY
ath.rse     INPSSGRVHTTFIQTGTATGRLASSDPNLQNIPVKYDEGKLIRKVFVPEG-GHVLIDADY
DPO1-ECOLI  INPKTGRVHTSYHQAVTATGRLSSTDPNLQNIPVRNEEGRRIRQAFIAPE-DYVIVSADY
            .  ..*...  *. ******.*.*******.*   .. . .    .. *** chimera     SQIELRILAHISEDERLISAFKNNVDIHSQTAAEVFGVDIADVTPEMRSQAKAVNFGIVY
tne.rse     SQIELRILAHLSGDENLLRAFEEGIDVHTLTASRIFNVKPEEVTEEMRRAGKMVNFSIIY
ath.rse     SQIELRILAHISEDERLISAFKNNVDIHSQTAAEVFGVDIADVTPEMRSQAKAVNFGIVY
DPO1_ECOLI  SQIELRIMAHLSRDKGLLTAFAEGKDIHRATAAEVFGLPLETVTSEQRRSAKAINFGLIY
            *****..*  *   **  .    .*            *  *   .** ..* chimera     GISDYGLARDIKISRKEAAEFINKYFERYPKVKEYLDNTVKFARDNGFVLTLFNRKRYIK
tne.rse     GVTPYGLSVRLGVPVKEAEKMIVNYFVLYPKVRDYIQRVVSEAKEKGYVRTLFGRKRDIP
ath.rse     GISDYGLARDIKISRKEAAEFINKYFERYPKVKEYLDNTVKFARDNGFVLTLFNRKRYIK
DPO1_ECOLI  GMSAFGLARQLNIPRKEAQKYMDLYFERYPGVLEYMERTRAQAKEQGYVETLDGRRLYLP
            *.. .**.  .   ***   . **  .  .*.    *.. *.* ** .*   .

chimera     DIKSTNRNLRGYAERIAMNSPIQGSAADIMKLAMIKVYQKLKENNLKSKIILQVHDELLI
tne.rse     QLMARDRNTQAEGERIAINTPIQGTAADIIKLAMIEIDRELKERKMRSKMIIQVHDELVF
ath.rse     DIKSTNRNLRGYAERIAMNSPIQGSAADIMKLAMIKVYQKLKENNLKSKIILQVHDELLI
DPO1_ECOLI  DIKSSNGARRAAAERAAINAPMQGTAADIIKRAMIAVDAWLQAEQPRVRMIMQVHDELVF
             .   .     ** *.*.**.**.****.* ***  .   *  .   .**.*****.
```

Fig. 17/3

```
chimera      EAPYEEKDIVKEIVKREMENAVALKVPLVVEVKEGLNWYENKI
tne.rse      EVPNEEKDALVELVKDRMTNVVKLSVPLEVDVTIGKTWS----
ath.rse      EAPYEEKDIVKEIVKREMENAVALKVPLVVEVKEGLNWYENKI
DPO1_ECOLI   EVHKDDVDAVAKQIHQLMENCTRLDVPLLVEVGSGENWDQAH-
             *   .. *  .    ..  * *    * *** *.*  * .*
```

Figure 18/1

SEQ ID No.: 19
SEQ ID No.: 20
SEQ ID No.: 21
SEQ ID NO.: 22

```
TNE UP   5'   CTG ACC ATG GCG AGA CTA TTT CTC TTT G  -3'
TNE LOW  5'   TCT GTC GAC CTT CAC ACC GTT CAG TTC CAT CC -3'
ATH UP   5' - AAG GTC GAC AGA GAT GCC CTC ATC CAA TAT ACC -3'
ATH LOW  5' - TAG CAA GCT TCT ATT TTG TCT CAT ACC AGT -3'
```
A.

crossing point 1

SEQ ID No.: 23
SEQ ID No.: 24
SEQ ID No.: 25

```
chimera_8   IEMPLVSVLARMELNGV  |  KVDRDALIQYTKEIENKILKLETQIYQIAGEWFNINSPKQLSY
tne.rse_    IEMPLVSVLARMELNGV  |  YVDTEFLKKLSEEYGKKLEELAEEIYRIAGEPFNINSPKQVSR
ath.rse_    IERPLIPVLYEMEKTGF  |  KVDRDALIQYTKEIENKILKLETQIYQIAGEWFNINSPKQLSY
```
B.

SEQ ID No.: 19
SEQ ID No.: 26
SEQ ID No.: 27

```
          5' ctg acc ATG GCG AGA CTA TTT CTC TTT G -3'
          TNEUP  |------------------------------>
                 ATG GCG AGA CTA TTT CTC TTT GAT GGA    27
                  M   A   R   L   F   L   F   D   G     9
1
.............................................................
```

SEQ ID No.: 28
SEQ ID No.: 29
SEQ ID No.: 50
SEQ ID No.: 21
SEQ ID No.: 30
SEQ ID No.: 31

```
1512  CGG ATG GAA CTG AAC GGT GTG TAC GTG GAC ACA GAG TTC CTG AAG AAA CTC   1563
 505   R   M   E   L   N   G   V   Y   V   D   T   E   F   L   K   K   L    521
     3'CC CAT CTT GAC TTG CCA CAC ctt CAg cTG TcT 5'
        <-----------------------============| TNELOW
                      "Sal I site "
                      ATHUP |===============================-------------->
                            5'  AAG Gtc Gac AGA GAT GCC CTC ATC CAA TAT ACC -3'
1387       ATG GAA AAA ACA GGA TTT AAG GTG GAT AGA GAT GCC CTC ATC CAA TAT ACC  1435
 463        M   E   K   T   G   F   K   V   D   R   D   A   L   I   Q   Y   T   479
```

.............................................................

Figure 18/2:

SEQ ID No.: 32
SEQ ID No.: 33
SEQ ID No.: 22

```
2526    GGA CTG AAC TGG TAT GAG ACA AAA TAG                      2553
 843     G   L   N   W   Y   E   T   K   *
             3´TG ACC ATA CTC TGT TTT ATC ttcgaacgat 5´
              <--------------------------------| ATHLOW
```

Figure 19:

SEQ ID No.: 34
SEQ ID No.: 35
SEQ ID No.: 36

```
                                                    crossing point 2
chimera__8      IMEPLVSVLARMELNGVYVDTEFLKKLSEEYGKKLEELAEEIYRIAGEPFNINSPKQVS|R
tne.rse___      IEMPLVSVLARMELNGVYVDTEFLKKLSEEYGKKLEELAEEIYRIAGEPFNINSPKQVS|R
ath.rse___      IERPLIPVLYEMEKTGFKVDRDALIQYTKEIENKILKLETQIYQIAGEWFNINSPKQLS|R
```
A.

TNE polymerase nucleotide sequence 1642-1689

SEQ ID No.: 37
SEQ ID No.: 38

```
              Bam HI site
              =========
1642   TCA CCG AAG CAG GTT TCA AGG ATC CTT TTT GAA AAA CTC GGC ATA AAA   1689
 548    S   P   K   Q   V   S   R   I   L   F   E   K   L   G   I   K    563
```

SEQ ID No.: 39
SEQ ID No.: 40
SEQ ID No.: 41
SEQ ID No.: 42

ATH polyerase nucleotide sequence 1513 - 1560

```
1513   TCA CCG AAA CAG CTT TCT TAC ATT TTG TTT GAA AAG CTA AAA CTT CCT   1560
 505    S   P   K   Q   L   S   Y   I   L   F   E   K   L   K   L   P    520

5´CA CCG AAA CAG CTT TCT agg atc cTG TTT GAA AAG CTA AAA CTT CCT G 3´
        |---------------m1---------------------------------+------------------>

......3´GT GGC TTT GTC GAA AGA tcc tag gAC AAA CTT TTC GAT TTT GAA GGA C 5´
        <---------------m2-------------------------------------------------|
```
B.

POLYMERASE CHIMERAS

This is a divisional application of application Ser. No. 09/623,326, filed Feb. 8, 2001now U.S. Pat. No. 6,607,883, which is the U.S. national phase of PCT/EP99/01674, filed Mar. 15, 1999, each of which is hereby incorporated by reference in its entirety.

The invention concerns polymerase chimeras which are composed of amino acid fragments representing domains and which combine properties of naturally occurring polymerases that are advantageous with regard to a particular application. It has surprisingly turned out that the domains from the various enzymes are active in the chimeras and exhibit a cooperative behavior. The present invention especially concerns those polymerase chimeras in which the domains having polymerase activity and domains having 3'-5' exonuclease activity are derived from different enzymes. Such chimeras can also have RT activity. In addition the present invention concerns a process for the production of the chimeras according to the invention and the use of these chimeras for the synthesis of nucleic acids e.g. during a polymerase chain reaction. Moreover the present invention concerns a kit which contains the polymerase chimeras according to the invention.

According to Braithwaite, D. K. and Ito, J. (1993) Nucl. Acids Res. 21, 787-802 DNA polymerases are divided according to the correspondence in their amino acid sequences into three main families with subclasses. Joyce, C. M. and Steitz, T. A. (1994) Annu. Rev. Biochem. 63, 777-822 give a summary of the motifs and conserved amino acids that were found. In prokaryotes the main distinction is made between three polymerases: polymerase I, II and III. These polymerases differ with regard to their function in the cell and with regard to their properties. DNA polymerase I is considered to be a repair enzyme and frequently has 5'-3' as well as 3'-5' exonuclease activity. Polymerase II appears to facilitate DNA synthesis which starts from a damaged template strand and thus preserves mutations. Polymerase III is the replication enzyme of the cell, it synthesizes nucleotides at a high rate (ca. 30,000 per minute) and is considered to be very processive. Polymerase III has no 5'-3' exonuclease activity. Other properties of polymerases are due to their origin such as e.g. thermostability or processivity.

Particular properties of polymerases are desirable depending on the application. For example thermostable, high-fidelity (i.e. polymerases with proof-reading activity), processive and rapidly synthesizing polymerases are preferred for PCR. Enzymes are preferred for sequencing which do not discriminate much between dideoxy and deoxy nucleotides. In contrast the proof-reading activity of polymerases, i.e. 3'-5' exonuclease activity, is not desirable for sequencing. For some applications e.g. PCR it is desirable that the polymerase has no or little 5'-3' exonuclease activity (5' nuclease activity).

Polymerases can also differ in their ability to accept RNA as a template i.e. with regard to their reverse transcriptase (RT) activity. The RT activity may be dependent on the presence of manganese or/and magnesium ions. It is often desirable that the RT activity of the polymerase is independent of manganese ions since the reading accuracy of polymerase is decreased in the presence of manganese ions. Polymerases additionally differ in their processivity which is also a desirable property for many applications.

There is therefore a need to optimize the properties of polymerases with regard to a particular application. In the past this was often achieved by introducing mutations or by deleting functions of the polymerases.

Thus for example the 5'-3' exonuclease activity was abolished by introducing mutations (Merkens, L. S. (1995) *Biochem. Biophys. Acta* 1264, 243-248) as well as by truncation (Jacobsen, H. (1974) *Eur. J. Biochem.* 45, 623-627; Barnes, W. M. (1992) *Gene* 112, 29-35). The ability of polymerases to discriminate between dideoxy and deoxy-nucleotides was reduced by introducing point mutations (Tabor S. and Richardson, C. C. (1995) *Proc. Natl. Acad. Sci.* 92, 6339-6343). Tabor and Richardson describe the construction of active site hybrids.

The object to provide polymerases with optimized properties was achieved by the present invention for the first time by producing polymerase chimeras by exchanging domains that are structurally and functionally independent of one another. Domains in the sense of the present invention are understood as regions which contain all essential centres or all functionally important amino acids such that the domains essentially retain their function. It is therefore also possible to exchange only parts i.e. functioning fragments of domains. Thus these domains can be referred to as functional amino acid fragments in the sense of the present invention. Furthermore the chimeras can be additionally modified by mutations or truncations. If it appears to be advantageous it is also possible to introduce mutations into the chimeras which further optimize their properties with regard to the respective application. Thus for example mutations can be introduced which reduce the ability of the polymerases to discriminate between dideoxy and deoxy nucleotides. Alternatively desired properties such as processivity can be strengthened or introduced by introducing mutations or by truncation. The introduction of mutations or truncations can also abolish undesired properties e.g. the 5' nuclease activity.

Thus polymerase chimeras are a subject matter of the present invention which combine advantageous properties of naturally occurring polymerases with regard to a particular application. The polymerase chimeras according to the invention are composed of functional amino acid fragments of different enzymes which preferably represent domains of different enzymes. The invention surprisingly showed that the domains from the different enzymes are active in the chimera and exhibit a cooperative behavior between the domains. The present invention also concerns general processes for the production of polymerase chimeras with optimized properties. This process according to the invention thus enables a chimera to be designed from an arbitrary combination of enzymes by exchanging domains. It is additionally preferred that the interactions at the sites of contact between the domains are further harmonized by various methods. This can for example lead to an increase in the thermostability of the chimeras. A further subject matter of the invention is a kit for the synthesis of nucleic acids which contains a chimera according to the invention.

Thermostable DNA polymerases with proof-reading function are being increasingly used in practice for PCR. The use of mixtures of Taq polymerase and thermostable proof-reading DNA polymerase (such as Pfu, Pwo, Vent polymerase) has proven to be particularly successful for the amplification of long DNA molecules. Thus a further subject matter of the present invention was to combine the high processivity and thermostability of Taq polymerase with the 3'-5' exonuclease activity of another DNA polymerase in one enzyme. Hence the present invention especially concerns thermostable polymerase chimeras which have a processivity which corresponds to at least that of Taq polymerase and have a low error rate when incorporating nucleotides into the polymer chain during amplification due to the presence of a 3'-5' exonuclease activity (proof-reading activity). The combination of these two properties enables for example a chimera to be generated which is able to make long PCR products i.e. nucleic acid fragments which are larger than 2 kb. The chimera accordinx tÜ Ühe invention is also suitable for amplifying shorter fragments.

The present invention therefore concerns in particular a polymerase chimera which is composed of functional amino acid fragments of two different polymerases wherein the first or the second polymerase has 3'-5' exonuclease activity and the polymerase chimera has 5'-3' polymerase activity as well as 3'-5' exonuclease activity. The polymerases can be naturally occurring or recombinant polymerases. The polymerase chimera according to the invention can be composed of functional amino acid fragments from two or several different polymerases. The polymerase chimera according to the invention can be composed of two or several functional amino acid fragments from the different polymerases. The amino acid sequence of the fragment can correspond to the naturally occurring sequence of the polymerase or to a sequence modified by mutations.

The amino acid fragments from which the polymerase chimera is constructed preferably each correspond to functional polymerase domains of the first or second polymerase. A functional polymerase domain in the sense of the present invention is a region which contains all amino acids that are essential for the activity and is abbreviated as domain in the following.

The present invention concerns in particular a polymerase chimera composed of functional amino acid fragments (in short domains) from at least two different polymerases wherein the domain having polymerase activity is homologous to one polymerase and the domain having 3' exonuclease activity is homologous to another polymerase. Moreover, this chimera can additionally have 5' exonuclease activity in which case the domain having 5' exonuclease activity can be homologous to the first or to the second polymerase. However, it is also possible that the 5' exonuclease domain is partially or completely deleted or has point mutations. The polymerase chimera according to the invention can additionally have reverse transcriptase (RT) activity.

It is additionally preferred that a part of the amino acid fragments of the polymerase chimeras corresponds to a part of the amino acid sequence of Taq polymerase.

The polymerase whose domain or amino acid fragment having 3'-5' exonuclease activity has been incorporated into the chimera can for example be a Pol-I type polymerase or also a Pol-II type polymerase. Representatives of the Pol-I type polymerase with 3'-5' exonuclease activity are for example *Escherichia coli* polymerase (Ec.1), *Salmonella* polymerase I, *Bacillus* polymerase I, *Thermosiphon* polymerase I and *Thermatoga neapolitana* polymerase (Tne). Representatives of the Pol-II type polymerase with 3'-5' exonuclease activity are for example *Pyrrococcus woesie* polymerase (Pwo), *Pyrococcus furiosus* polymerase (Pfu), *Thermococcus litoralis* polymerase (Tli), *Pyrodictum abyssi*.

Representatives of Pol-I type and Pol-II type polymerases which were mentioned as examples are described in more detail in the following:

The Taq DNA polymerase from *Thermus aquaticus* (Taq polymerase), *Escherichia coli* DNA polymerase I (*E. coli* polI) and *Thermotoga neapolitana* DNA polymerase (Tne polymerase) are bacterial DNA polymerases from the A family. They are DNA polymerases of the polI type since the various enzymatic activities are located in the various domains in a relatively similar manner to that found in *E. coli* polI. The *Pyrococcus woesi* DNA polymerase (Pwo polymerase) is, like *Thermococcus litorales* DNA polymerase (Vent™ polymerase) and *Pyrococcus furiosus* DNA polymerase (Pfu polymerase), an archaebacterial DNA polymerase of the B family.

Taq polymerase is described by Chien, A. et al. (1976) J. Bacteriol. 127, 1550-1557, Kaledin, A. S. et al. (1980) Biokhimiya 45, 644-651 and Lawyer, F. C. et al. (1989) J. Biol. Chem. 264, 6427-6437. It was originally isolated from the thermophilic eubacterium *Thermus aquaticus* and later cloned in *E. coli*. The enzyme has a molecular weight of 94 kDa and is active as a monomer. Taq polymerase is suitable for use in the polymerase chain reaction (PCR) since it has a high thermal stability (half life of 40 minutes at 95° C./5 minutes at 100° C.) and a highly processive 5'-3' DNA polymerase (polymerisation rate: 75 nucleotides per second). Apart from the polymerase activity, a 5' nuclease activity was detected by Longley et al. (1990) Nucl. Acids Res. 18, 7317-7322. The enzyme has no 3'-5' exonuclease activity so that errors occur during the incorporation of the four deoxyribonucleotide triphosphates to successively extend polynucleotide chains which interfere with the gene amplification (error rate: $2 \times 10^{-4}$ errors/base, Cha, R. S. and Thilly, W. G. (1993) PCR Methods Applic. 3, 18-29). The tertiary structure of Taq polymerase has been known since 1995 (Kim et al., 1995, Korolev et al., 1995).

*E. coli* polI is described in Kornberg, A. and Baker, T. A. (1992) DNA Replication, 2nd edition, Freeman, N.Y., 113-165. The enzyme has a molecular weight of 103 kDa and is active as a monomer. *E. coli* polI has 5' nuclease activity and 5'-3' DNA polymerase activity. In contrast to Taq polymerase, it additionally has a 3'-5' exonuclease activity as a proof-reading function. *E. coli* polI and its Klenow fragment (Jacobsen, H. et al. (1974) Eur. J. Biochem. 45, 623-627) were used for PCR before the introduction of Taq polymerase. However, due to their low thermal stability they are less suitable since they have to be newly added to each cycle. The tertiary structure of the Klenow fragment of *E. coli* polI has been known since 1983 (Brick, P. et al., (1983) J. Mol. Biol. 166, 453-456, Ollis, D. L. et al. (1985) Nature 313, 762766 and Beese, L. S. et al. (1993) Science 260, 352-355).

Tne polymerase was isolated from the thermophilic eubacterium *Thermotoga neapolitana* and later cloned in *E. coli*. The amino acid sequence of the Tne polymerase is similar to that of *Thermotoga maritima* DNA polymerase (UITma™ polymerase) (personal information from Dr. B. Frey). It has a high thermal stability, 5' nuclease activity, 3'-5' exonuclease activity and 5'-3' DNA polymerase activity. A disadvantage is the low polymerisation rate compared with that of Taq polymerase. The UITma™ polymerase which has a similar amino acid sequence is used for PCR if a high accuracy is required. Of the structure of Tne polymerase, only the amino acid sequence is known up to now (Boehringer Mannheim). However, the enzyme is homologous to *E. coli* polI so that, although the tertiary structure is unknown, homology modeling is possible.

Pfu polymerase was isolated from the hyper-thermophilic, marine archaebacterium *Pyrococcus furiosus*. It has a high thermal stability (95% activity after one hour at 95° C.), 3'-5' exonuclease activity and 5'-3' DNA polymerase activity (Lundberg, K. S. et al. (1991) Gene 108, 1-6). The accuracy of the DNA synthesis is ca. 10 times higher than that of Taq polymerase. It is used for PCR if a high accuracy is required. Of the structure only the amino acid sequence is known up to now.

Pwo polymerase (PCR Applications Manual (1995), Boehringer Mannheim GmbH, Biochemica, 28-32) was originally isolated from the hyperthermophilic archae-bacterium *Pyrococcus woesi* and later cloned in *E. coli*. The enzyme has a molecular weight of about 90 kDa and is active as a monomer. Pwo polymerase has a higher thermal stability than Taq polymerase (half life >2 hours at 100° C.), a highly processive 5'-3' DNA polymerase activity and a high 3'-5' exonuclease activity which increases the accuracy of the DNA synthesis. The enzyme has no 5' nuclease activity. The polymerisation rate (30 nucleotides per second) is less than that of Taq polymerase. The enzyme is used for PCR if a high accuracy is required. The accuracy of the DNA synthesis is more than 10 times higher than when using Taq polymerase.

Ath polymerase was isolated from the thermophilic archaebacterium *Anaerocellum thermophilum* and later cloned in *E. coli*. Ath polymerase has a high thermal stability and still has at least 90% of the original activity after an incubation of 30 min at 80° C. in the absence of stabilizing detergents. The polymerase also has RT activity in the presence of magnesium ions. Ath polymerase is deposited at the "Deutsche Sammlung von Mikroorganismen und Zellkulturen GmbH", Mascheroder Weg 1b, D38124 Braunschweig DSM Accession No. 8995. The Ath polymerase has 5'-3' polymerase activity, 5'-3' exonuclease activity but no 3'-5' exonuclease activity.

Histidine tags or other purification aids can be additionally incorporated into the amino acid sequence of the polymerase chimeras to improve the purification.

There are four main methods for introducing a 3'-5' exonuclease activity of a polymerase into another polymerase for example into Taq polymerase which are also a subject matter of the present invention:

1. Insertion of the 3'-5' Exonuclease Region of Another DNA Polymerase by Exchange of a Molecular Region of Taq Polymerase This approach is particularly suitable since the Taq polymerase is homologous to *E. coli* polI which is composed of domains which are functionally and structurally independent (Joyce, C. M. and Steitz, T. A. (1987) TIBS 12, 288-292) and can serve as a model for other DNA polymerases (Joyce, C. M. (1991) Curr. Opin. Struct. Biol. 1, 123-129). Suitable DNA polymerases for the exchange are those for which a 3'-5' exonuclease activity has been demonstrated, whose DNA sequence is known and the gene coding for the 3'-5' exonuclease activity is available. For a rational protein design based on model structures it is additionally advantageous that the 3'-5' exonuclease region and the polymerase region are homologous to *E. coli* polI. The 3'1-5' exonuclease region preferably fits well into the structure of *E. coli* polI and adjoins the polymerase region of Taq polymerase. Further advantages are an elucidated tertiary structure with available structural data and high thermal stability of the protein.

The following DNA polymerases are thus for example suitable:

a. *E. coli* polI

Apart from thermal stability, *E. coli* polI fulfils all the above-mentioned conditions. The tertiary structure of the Klenow fragment is available in the Brookhaven data bank and, like Taq polymerase, it belongs to the A family of DNA polymerases. The identity in the amino acid sequence is 32%. Taking the known domain structure into consideration, the largest agreements are found in the N-terminal and in the C-terminal region of the two proteins (32% identity in the 5' nuclease domain, 49% identity in the polymerase domains). The shorter Taq polymerase has several deletions in the region of the 3'-5' exonuclease domain (14% identity in the 3'-5' exonuclease domain and intermediate domain). Since *E. coli* polI is thermolabile and the interactions at the interface between the two domains in the chimeric protein are no longer optimal, it is probable that the protein chimera will also have a lower thermal stability than that of Taq polymerase. This can be redressed by subsequent modification of amino acids at the interface.

b. Thermostable DNA Polymerases

Among the thermostable DNA polymerases with 3'-5' exonuclease that are nowadays used for PCR, the Pwo polymerase, Pfu polymerase, Vent™ polymerase, Tne polymerase and UITma™ polymerase appear to be suitable for combination with the Taq DNA polymerase. The genes of the Pwo polymerase and the Tne polymerase are accessible (via the Boehringer Mannheim Company). The Pfu polymerase can be obtained from Stratagene Inc. The Tne polymerase is well suited for a rational protein design due to its homology to Taq polymerase and *E. coli* polI. When using the Pfu polymerase designs are only possible based on amino acid sequence alignments taking into consideration the known conserved amino acids and motifs that are essential for the function.

2. Modification of the Taq DNA Polymerase in the Intermediate Domain

In order to insert a 3'-5' exonuclease activity it is necessary to insert all amino acids that are essential for the activity into the structure. According to the present state of knowledge this applies in particular to the three motifs Exo I, Exo II and Exo III. The essential motifs must additionally be linked in a suitable manner in order to be placed in the spatial position necessary for catalysis.

It is also possible to modify the Taq DNA polymerase in the polymerase region. A de novo design of polymerases is also in principle conceivable.

The chimeras according to the invention can be additionally optimized by:

1. Removing the 5' nuclease domain (possible also proteolytically) or subsequently inactivating the 5' nuclease activity (described in Merkens, L. S. (1995) Biochem. Biophys. Acta 1264, 243-248)
2. Modification by point mutations or fragment exchange
3. Optimization of the structures at the interface of the chimeras
4. Optimization by random mutagenesis and/or random recombination with other polymerase genes (molecular evolution).

Examples of polymerase chimeras according to the invention are the following:

Taq DNA polymerase (M1-V307)*E. coli* DNA polymerase (D355-D501) Taq DNA polymerase (A406-E832)

Taq DNA polymerase (M1-P291)*E. coli* DNA polymerase (Y327-K511) Taq DNA polymerase (L416-E832)

Taq DNA polymerase (M1-P291)*E. coli* DNA polymerase (Y327-H519) Taq DNA polymerase (E424-E832): point mutation A643G; Ile455Val SEQ ID NO.:1

Taq DNA polymerase (M1-P291)*E. coli* DNA polymerase (Y327-V536) Taq DNA polymerase (L441-E832)

Taq DNA polymerase (M1-P291)*E. coli* DNA polymerase (Y327-G544) Taq DNA polymerase (V449-E832); SEQ ID NO.:2

Taq DNA polymerase (M1-P302)*E. coli* DNA polymerase (K348-S365) Taq DNA polymerase (A319-E347) *E. coli* DNA poly(N450-T505) Taq DNA polymerase (E410-E4832);

Taq DNA polymerase (M1-V307) Tne DNA polymerase (D323-D468) Taq DNA polymerase (A406-E832)

Taq DNA polymerase (M1-P291) Tne DNA polymerase (P295-1478) Taq DNA polymerase (L416-E832)

Taq DNA polymerase (M1-P291) Tne DNA polymerase (P295-E485) Taq DNA polymerase (E424-E832); silent mutation A1449C SEQ ID NO.:3

Taq DNA polymerase (M1-P291) Tne DNA polymerase (P295-V502) Taq DNA polymerase (L441-E832)

Taq DNA polymerase (M1-P291) Tne DNA polymerase (P295-G510) Taq DNA polymerase (V449-E832); silent mutation C1767T SEQ ID NO.:4

Taq DNA polymerase (M1-P302) Tne DNA polymerase (E316-D333) Taq DNA polymerase (A319-E347) Tne DNA polymerase (1381-M394) Taq DNA polymerase (R362-L380) Tne DNA polymerase (E415-T472) Taq DNA polymerase (E410-E832);
G308D/V310E/L352N/L356D/E401Y/R305D Taq DNA polymerase (1-291) Pfu DNA polymerase (V100-R346) Taq DNA polymerase (E424-E832)

Taq DNA polymerase (1-291) Pfu DNA polymerase (H103-S334) Taq DNA polymerase (E424-E832); SEQ ID NO.:5

Taq DNA polymerase (1-291) Pfu DNA polymerase (V100-F389) Taq DNA polymerase (E424-E832)

Taq DNA polymerase (1-291) Pfu DNA polymerase (V100-F389) Taq DNA polymerase (V449-E832); SEQ ID NO.:6

Taq DNA polymerase (1-291) Pfu DNA polymerase (M1-F389) Taq DNA polymerase (V449-E832)

Of the above-mentioned polymerase chimeras the following were examined in more detail:

Taq DNA polymerase (M1-P291)*E. coli* DNA polymerase (Y327-H519) Taq DNA polymerase (E424-E832): point mutation A643G; Ile455Val (Taq Ec1) SEQ ID NO.:1

Taq DNA polymerase (M1-P291)*E. coli* DNA polymerase (Y327-G544) Taq DNA polymerase (V449-E832), (Taq Ec2) SEQ ID NO.:2

Taq DNA polymerase (M1-P291) Tne DNA polymerase (P295-E485) Taq DNA polymerase (E424-E832); silent mutation A1449C (Taq Tne1) SEQ ID NO.:3

Taq DNA polymerase (M1-P291) Tne DNA polymerase (P295-G510) Taq DNA polymerase (V449-E832); silent mutation C1767T (Taq Tne2) SEQ ID NO.:4

Taq DNA polymerase (1-291) Pfu DNA polymerase (V100-R346) Taq DNA polymerase (E424-E832), (Taq Pfu1) SEQ ID NO.:5

Taq DNA polymerase (1-2,91) Pfu DNA polymerase (V100-F389) Taq DNA polymerase (V449-E832), (Taq Pfu2) SEQ ID NO.:6

In order to select suitable DNA polymerases, multiple amino acid sequence alignments of available sequences of DNA polymerases and DNA binding proteins are established for example with the program GCG (Devereux et al., 1984, Nucl. Acids Res. 12, 387-395). In order to find a good alignment it is necessary to take into consideration the secondary structure predictions, known structure-based sequence alignments, known motifs and functionally essential amino acids as well as phylogenetic aspects. If the proteins are composed of functionally and structurally independent domains it is appropriate to firstly establish the amino acid sequence alignments with respect to the individual domains and only afterwards to combine them into a complete sequence alignment.

If homologous sequences are found whose tertiary structure is known, then it is possible to derive a 3D model structure from the homologous protein. The program BRAGI (Reichelt and Schomburg, 1988, J. Mol. Graph. 6, 161-165) can be used to make the model. The program AMBER (Weiner et al., 1984, J. Am. Chem. Soc. 106, 765-784) can be used for energy minimization of the structures of individual molecule regions and whole molecules and the program Procheck can be used to check the quality of the model. If only the Cα coordinates of the structure of the initial protein are available, the structure can for example be reconstructed using the program O (Jones et al., 1991, Acta Cryst. A47, 110-119). It is also possible to obtain Cα coordinates that are not available in the protein data bank but have been already published as a stereo picture by scanning the stereo picture and picking out the coordinates (for example using the program Magick) and calculating the z-coordinates (for example using the program stereo). Variants can be designed based on amino acid sequence alignments, based on 3D models or based on experimentally determined 3D structures.

In addition chimera variants were produced in which the domain with polymerase activity has reverse transcriptase activity. Examples of suitable polymerases are e.g. the polymerase from *Anaerocellum thermophilum* Ath or *Thermus thermophilum* Tth. The 3'-5' exonuclease activity is inserted by a domain which is derived from another polymerase e.g. the Tne polymerase or the Pfu or Pwo polymerase. This chimera can additionally have 5'-3' exonuclease activity in which case the domain with 5' exonuclease activity can be derived from the first as well as from the second polymerase.

Figure 21:
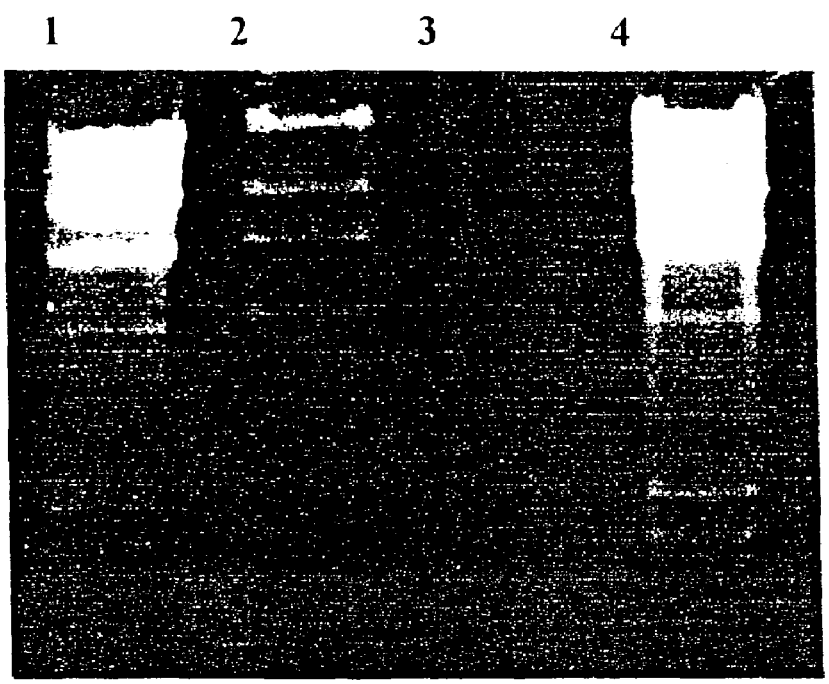
Figure 22:
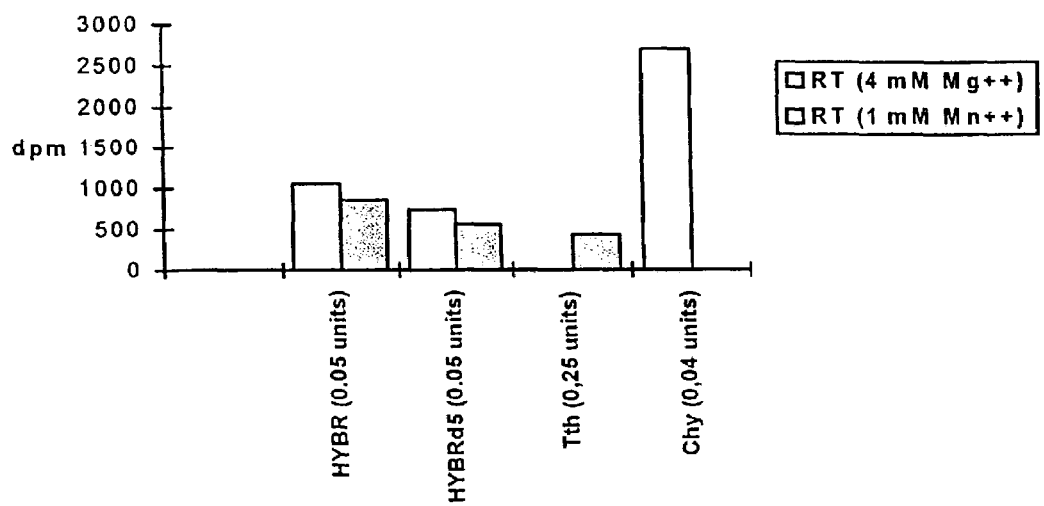

The recombinant hybrid polymerases HYB and HYBd5, like the DNA polymerase from *Anaerocellum thermophilum*, have a relatively strong reverse transcriptase activity in the presence of magnesium ions as well as in the presence of manganese ions. As shown in FIG. 22 the ratio of polymerase activity to reverse transcriptase activity is more favourable than with the Tth polymerase which is the most common and well-known enzyme of this type. This finding applies to the magnesium-dependent as well as to the manganese-dependent reverse transcriptase activity. It can be concluded from this that the polymerase domain which is derived from the Anaerocellum polymerase also exhibits full activity in the hybrid enzyme. The variant HYBd5 additionally has 3'-5' exonuclease activity as shown in FIG. 21. This is inhibited by the presence of deoxynucleoside triphosphates as expected for the typical "proof-reading activity". The exonuclease domain which is derived from the DNA polymerase from *Thermotoge neapolitana* is thus also active in the hybrid molecule. The ability to inhibit the exonuclease activity also demonstrates that both domains of the hybrid polymerase molecule interact and thus the hybrid polymerase is functionally very similar to the natural enzyme.

The production of domain exchange variants by genetic engineering can be achieved by PCR mutagenesis according to the SOE method (Horton et al. (1989) Gene 77, 61-68) or by the modified method (cf. scheme in the examples) with the aid of chemically synthesized oligodeoxynucleotides. The respective DNA fragments are separated on an agarose gel, isolated and ligated into the starting vector. pUC derivatives with suitable promoters such as pTE, pTaq, pPL, Bluescript can be used as starting vectors for *E. coli*. The plasmid DNA is transformed into an *E. coli* strain, for example XL1-blue, some clones are picked out and their plasmid DNA is isolated. It is also possible to use other strains such as Nova Blue, BL21 (DE), MC1000 etc. Of course it is also possible to clone into other organisms such as into yeast, plant and mammalian cells. A preselection of clones whose plasmid DNA is sequenced in the modified region is made by restriction analysis.

The gene expression in the target proteins can be induced by IPTG in many plasmids such as Pbtaq. When producing many different variants it is appropriate to establish a universal purification procedure. Affinity chromatography on Ni-NTA (nickel-nitrilotriacetic acid) agarose is well suited for this which can be used after attaching a His tag to the protein, for example by PCR. The protein concentrations can be determined with the protein assay ESL (Boehringer Mannheim) and contaminating side activities of the preparations can be determined as described for the commercially available Taq polymerase (Boehringer Mannheim). Polymerase, exonuclease activity and thermostability tests are carried out to further characterize the variants and the respective temperature optimum is determined. The polymerase activities of the chimeras can be determined in non-radioactive test systems for example by determining the incorporation rate of Dig-dUTP into DNase activated calf thymus DNA, or in radioactive test systems by for example determining the incorporation rate of α-[$^{32}$P]dCTP into M13 mp9 ssDNA. In order to determine the temperature optima of the polymerase activity of the chimeras, the polymerase reaction is carried out at different temperatures and the specific activities are calculated. The residual activities (i.e. the percentage of the initial activity without heat treatment) after heat treatment are measured in order to determine the thermal stabilities. The 3'-5' exonuclease activity can be demonstrated by incorporation of a 5'-Dig-labelled primer which anneals to a DNA template strand starting at its 3' end. The correction of 3' mismatched primers and their extension (proof reading) can be shown by the extension of mismatched 5'-Dig-labelled primers which anneal to a template strand in the recognition sequence of a restriction enzyme (e.g. EcoRI). A cleavage with the restriction enzyme is only possible when the mismatch is corrected by the enzyme. The processivity can be examined by using variants in the PCR. If the enzyme is not sufficiently thermostable for use in PCR, a PCR can be carried out at the temperature optimum as the extension temperature with successive addition of enzyme. The exonuclease activity of the chimeras can be determined in a radioactive test system. For this a certain amount of the chimeric polymerases (usually 2.5 U) is incubated for 4 hours at various temperatures with labelled DNA (5 μg [$^3$H] DNA in the respective test buffers). dNTPs were optionally added at various concentrations (0-0.2 mM). After terminating the reaction the release of radioactively labelled nucleotides is determined.

A further subject matter of the present invention is the DNA sequence of the polymerase chimeras described above. In particular the DNA sequences SEQ ID NO.: 1-6 are a subject matter of the present invention. The present invention additionally concerns the amino acid sequences of the polymerase chimera described above. In particular the amino acid sequences SEQ ID NO.: 7-12 are a subject matter of the present invention. Moreover the amino acid sequence SEQ ID NO.:43 is a subject matter of the invention.

Vectors which contain the above-mentioned DNA sequences are a further subject matter of the present invention. pBTaq (plasmid Pbtaq4_oligo 67 (Villbrandt (1995), dissertation, TU Braunschweig)) is a preferred vector.

The *E. coli* strains, in particular the strain *Escherichia coli* XL1-blue which contain the vector which carries the polymerase chimera gene are a further subject matter of the invention. The following strains were deposited at the DSM, "Deutsche Sammlung von Mikroorganismen und Zellkulturen GmbH", Mascheroder Weg 1b, D-38124 Braunschweig:

*E. coli* XL1 Blue x pBTaqEc1: TaqEc1(SEQ ID NO:1) DSM No. 12053

*E. coli* XL1 Blue x pBTaqTne1:TaqTne1(SEQ ID NO: 3) DSM No. 12050

*E. coli* XL1 Blue x pBTaqTne2:TaqTne2 (SEQ ID NO: 4) DSM No. 12051

*E. coli* XL1 Blue x pBTaqPfu1:TaqPfu1(SEQ ID NO: 5) DSM No. 12052

The polymerase chimeras according to the invention are particularly suitable for amplifying DNA fragments e.g. for the polymerase chain reaction. A further application is for example to sequence DNA fragments.

A preferred vector for the Ath-Tne chimera is the following:

*E. coli* BL 21 (DE3) plysSxPETHYBR: HYBR

*E. coli* BL 21 (DE3) plyssxpETHYBR d5: HYBR d5

The *E. coli* strains which contain the vector which carries the polymerase chimera gene are a further subject matter of the invention. The following strains were deposited at the DSM, "Deutsche Sammlung von Mikroorganismen und Zellkulturen GmbH", Mascheroder Weg 1b, D-38129 Braunschweig: HYBR (DSM No. 12720); HYBR d5 (DSM No. 12719).

The production of the above-mentioned Ath-Tne chimeras is described for example in examples 8-11. The chimeras according to the invention which have RT activity are particularly suitable for the reverse transcription of RNA.

A further subject matter of the present invention is a kit for amplifying DNA fragments which contains at least one of the polymerase chimeras according to the invention.

SHORT DESCRIPTION OF THE FIGURES

FIG. 1:
DNA sequence of the Taq DNA polymerase (M1-P291) *E. coli* DNA polymerase (Y327-H519) Taq DNA polymerase (E424-E832): point mutation A643G; Ile455Val SEQ ID NO.:1; and the corresponding amino acid sequence SEQ ID NO.:7.

FIG. 2:
DNA sequence of the Taq DNA polymerase (M1-P291) *E. coli* DNA polymerase (Y327-G544) Taq DNA polymerase (V449-E832); SEQ ID NO.:2; and the corresponding amino acid sequence SEQ ID NO.:8.

FIG. 3:
DNA sequence of the Taq DNA polymerase (M1-P291) Tne DNA polymerase (P295-E485) Taq DNA polymerase (E424-E832); silent mutation A1449C SEQ ID NO.:3; and the corresponding amino acid sequence SEQ ID NO.: 9.

FIG. 4:
DNA sequence of the Taq DNA polymerase (M1-P291) Tne DNA polymerase (P295-G510) Taq DNA polymerase (V449-E832); silent mutation C1767T SEQ ID NO.:4; and the corresponding amino acid sequence SEQ ID NO.:10.

FIG. 5:
DNA sequence of the Taq DNA polymerase (1-291) Pfu DNA polymerase (H103-S334) Taq DNA polymerase (E424-E832); SEQ ID NO.:5; and the corresponding amino acid sequence SEQ ID NO.:11.

FIG. 6:

DNA sequence of the Taq DNA polymerase (1-291) Pfu DNA polymerase (V100-F389) Taq DNA polymerase (–V449-E832); SEQ ID NO.:6; and the corresponding amino acid sequence SEQ ID NO.:12.

FIG. 7:

Purification of the domain exchange variant TaqEc1 on Ni-NTA agarose. Analysis on an 8% polyacrylamide gel stained with Coomassie blue.

Lanes: 1,8 protein molecular weight marker Broad Range (200 kDa, 116.25 kDa, 97.4 kDa, 66.2 kDa, 45 kDa, 31 kDa)
lane 2 soluble proteins
lane 3 column flow-through
lane 4 wash fraction buffer B
lane 5 wash fraction buffer A
lanes 6,7 eluate fraction buffer C
protein yield ($OD_{280}$) about 7 mg

FIG. 8:

Determination of protein purity: SDS-PAGE, Phast system (10-15%): silver staining MW: protein molecular weight markers; NHis-TaqPol: Taq DNA polymerase with N-terminal His tag; TaqEc1, TaqTne1, TaqTne2: domain exchange variants.

FIG. 9:

Specific activities of the domain exchange variants at various temperatures.

FIG. 10:

Testing the domain exchange variants in the PCR with successive addition of enzyme, extension at 72° C.
lambda DNA (left): size of the target sequence=500 bp
plasmid pa (right): size of the target sequence=250 bp
lane 1: Taq DNA polymerase (BM Co.), 100 ng, 5 units
lane 2: domain exchange variant TaqEc1, 500 ng, 1.25 units/cycle
lane 3: domain exchange variant TaqTne1, 50 ng, 3.6 units/cycle
lane 4: domain exchange variant TaqTne2, 50 ng, 3.5 units/cycle
III: DNA length standard III (BM Co.)
VI: DNA length standard VI (BM Co.).

Result: When the domain exchange variant TaqTne2 was used, PCR products of the correct size were formed.

FIG. 11:

Testing the domain exchange variants in the PCR with successive addition of enzyme, extension at 55° C.
lambda DNA (left): size of the target sequence=500 bp
plasmid pa (right): size of the target sequence=250 bp
lane 1: domain exchange variant TaqEc1, 500 ng, 6 units/cycle
lane 2: domain exchange variant TaqTne1, 50 ng, 7.5 units/cycle
III: DNA length standard III (BM Co.)
VI: DNA length standard VI (BM Co.).

Result: When the domain exchange variant TaqEc1 was used, PCR products of the correct size were formed.

FIG. 12:

3'-5' exonuclease test-variant TaqEc1, incubation at 72° C., primer P1.

FIG. 13:

3'-5' exonuclease test-variant TaqEc1, incubation at 50° C., primer P1 (left), primer P2 (right).

FIG. 14:

Correction of 3' mismatched primers and their extension—variant TaqEc1 (3' mismatch primer correction assay) (−): without restriction enzyme digestion (+): restriction enzyme digestion with EcoRI.

FIG. 15:

Schematic Representation

Degradation of primers at the 3' end (3'-5' exonuclease assay) and correction of 3' mismatched primers and their extension (3' mismatch primer correction assay) (SEQ ID NOS:47 and 48).

FIG. 16:

Schematic representation: simplified flow chart, degradation of primers at the 3' end and correction of 3' mismatched primers and extension.

FIG. 17:

CLUSTAL W (1.5) multiple sequence alignment of the Ath (SEQ ID NO:45), Tne (SEQ ID NO:44), PolI polymerase (DPO1 ECOLI; SEQ ID NO:46) genes as well as of the predicted gene of the polymerase chimera (SEQ ID NO:43).

FIG. 18:

A. Structure of the primers (SEQ ID NOS:19-22) which were used for the PCR amplification of the Tne-Exo and the Ath polymerase domains.

B. Part of the amino acid sequence alignment of two polymerases which exhibited the selected crossing point (SEQ ID NOS:23-25).

C. Nucleotide sequences and position of the primers which were designed for the construction of the hybrid polymerase genes (SEQ ID NOS: 19, 26-29, 50, 21, 30-33 and 22, respectively). The sequences of the primers which are not complementary to the target sequence are shown in small letters. Complementary "overlapping" sequences in the TNELOW and ATHUP primers are double underlined.

FIG. 19:

A. Part of the alignment of the Ath and Tne amino acid sequences which show the homologous region that was used to splice together the domains of the two polymerases (SEQ ID NOS:34-36).

B. Nucleotide and amino acid sequences of the two polymerases in the splicing region (SEQ ID NOS:37-42). The figure shows the single BamHI cleavage site in the Tne DNA sequence and the sequence of the two oligos that were constructed in order to introduce the BamHI cleavage site into the Ath polymerase.

FIG. 20:

Construction of the gene of the polymerase chimera (cf. also example 8).

FIG. 21:

3'-5' exonuclease activity of the recombinant DNA polymerase.
1-DNA of the lambda phage hydrolyzed by HindIII
2-DNA of the lambda phage hydrolyzed by HindIII, and DNTP, and recombinant DNA polymerase
3-DNA of the lambda phage hydrolyzed by HindIII, without DNTP, with recombinant DNA polymerase
4-DNA of the lambda phage hydrolyzed by HindIII.

FIG. 22:

Reverse transcriptase activity of the recombinant polymerases HYB and HYBd5. The DNA polymerase activity of a 2 µl extract from *E. coli* BL21 (DE3) plyssxpETHYBr and *E. coli* BL21 (DE3) plyssxpETHYBRd5 was determined with a precision of 0.05 units. These amounts were used to determine the reverse transcriptase activity of the hybrid polymerases and the effect of 1 mM manganese or 4 mM magnesium ions. The controls were Tth (0.25 units) as a manganese-dependent reverse transcriptase and *C. therm.* polymerase (Roche Molecular Biochemicals) as a magnesium-dependent reverse transcriptase.

EXAMPLE 1

Construction and Cloning

Establishing a Universal Purification Procedure

Affinity chromatography on Ni-NTA (nickel-nitrilotriacetic acid) agarose was used to standardize the purification protocol for the domain exchange variants. Before producing the protein variants it was necessary to attach or insert a His tag to or into the Taq DNA polymerase. Two different His tag variants in the plasmid Pbtaq4_oligo67 (Boehringer Mannheim) were des5igned and produced. The variant NHis-TaqPol contains an N-terminal His tag, an enterokinase cleavage site to optionally cleave the His tag and an epitope for the detection of His tag proteins with antibodies (Quiagen). It was produced by PCR from the EcoRI site up to the PstI site. In the N-terminal protein sequencing the twenty N-terminal amino acids of the variant NHis-TaqPol were confirmed as correct.

Sequence: NHis-TaqPol

```
EcoRI codon from TagPol
5'GAATTC ATGAGGGGC TCG CAT CAC CAT CAC CAT CAC GCT GCT GAC GAT GAC GAT
AAA ATG AGG GGC 3'

MetArgGlySerHisHisHisHisHisHis Ala Ala AspAspAspAspLysMet
Arg Gly

MRGS'Hisepitope[Met-Arg-Gly-Ser-(His)₆] enterokinase[(Asp)₄-Lys-X]
  (SEQ ID NO:17) (SEQ ID NO:18)

SEQ ID No.:13: 5' GAATTCATGAGGGGC TCG CAT CAC CAT
CAC CAT CAC GCT GCT GAC GAT GAC GAT AAA ATG AGG GGC 3'

SEQ ID No.:14: Met Arg Gly Ser His His His His His His
Ala Ala Asp Asp Asp Asp Lys Met Arg Gly
```

The variant 5DHis-TaqPol contains a His tag in a flexible loop of the 5' nuclease domain between glycine 79 and glycine 80 of the Taq DNA polymerase and was produced by PCR mutagenesis from the EcoRI site up to the PstI site.

Sequence: 5DHis-TaqPol

```
5' GAG GCC TAC GGG CAT CAC CAT CAC CAT CAC GGG TAC AAG GCG    SEQ ID No.: 15
3'

GluAlaTyrGlyHisHisHisHisHisHisGlyTyrLysAla                 SEQ ID No.: 16
```

The correctness of the plasmid DNA in each modified region of the two new genes was confirmed by DNA sequencing. Both modified genes were expressed under the same conditions and at the same rate as the initial protein without a His tag, they could be readily purified by Ni-NTA agarose and behaved like Taq polymerase without a His tag in the standard PCR. The N-terminal His tag was used to purify the domain exchange variants.

Amino Acid Sequence Alignments

The following amino acid sequence alignments were set up in order to design the domain exchange variants:

1. Tne, *E. coli* I and Taq DNA polymerase
2. Pfu, *E. coli* I and Taq DNA polymerase
3. Multiple amino acid sequence alignments of DNA polymerases The alignments were established with the program GCG with reference to individual molecule regions (domains) and assembled to form the complete sequence alignment taking into consideration the known secondary structures, motifs and essential amino acids and using the structure-based sequence alignment of the sequences of the 3'-5' exonuclease domain of the Klenow fragment with the corresponding domain of Taq DNA polymerase (FIG. 2d in Kim et al. (1995) Nature 376, 612-616).

In order to select the initial structure of the Klenow fragment for the homology modelling, the structures of *E. coli* DNA polymerase I that were available at that time were compared using the program Bragi and an RMS fit:

Klenow fragment-dCMP complex (PDB code: 1 dpi), 2.8 Å (1987), Klenow fragment-dCTP complex (PBD-code: 1 kfd) 3.9 Å (1993) and Klenow fragment, D355 A—DNA complex (PBD-code: 1 kln) 3.2 Å (1994).

The structure Klenow fragment (PDB-code: 1 kln) was selected. Two loops were incorporated into the two regions in which there were no coordinates (Bragi program) and energy-minimized (Amber program). The quality of the protein structure was checked (Procheck program).

Construction of 3D Models

A 3D model of the molecular region of the Taq DNA polymerase which comprises amino acids 292-832 was constructed using the Bragi program in homology to the structure of the Klenow fragment (PDB-code: 1 kln). The modelling comprised amino acid substitutions, introduction of insertions and deletions, energy-minimization of the new loop regions and energy-minimization of the entire molecule (Amber program).

The structure of Taq DNA polymerase was already published at the time of the modelling work but was not available in the protein data bank. In order to set up a model of the intermediate domain of the Taq DNA polymerase which corresponds to the 3'-5' exonuclease domain of the Klenow fragment (amino acids 292-423), a stereo picture (FIG. 2c in Kim et al. (1995) Nature 376, 612-616) was scanned, the Cα coordinates were picked out on the screen (x and y coordinates for the left and right picture) (Magick program, (John Cristy, E.I. du Pont De Nemours and Company Incorporated)), the z coordinates were calculated (Stereo program, (Collaborative Computational Project, Number 4 (1994) Acta Cryst. D50, 760-763)), the protein main chain was reconstructed with generation of a poly-alanine (program O), amino acid substitutions were carried out (Bragi program) and an energy-minimization of the entire molecule was carried out (Amber program). The model of the amino acid residues 292-423 (see above) was added to the model of the polymerase domain (amino acids 424-832) (see above) while allowing for the structural alignments of the Taq DNA polymerase with the Klenow fragment (FIGS. 2b and 2c in Kim et al. (1995) Nature 376, 612-616). The entire model structure was energy-minimized (Amber program) and the quality of the model structure was checked (Procheck program, (Laskowski, R., A., et al. (1993) J. Appl. Cryst. 26, 283-291)).

A 3D model of the Tne DNA polymerase (residues 297-893) was set up in homology to the structure of the Klenow fragment (PDB-code: 1 kln). The modelling included amino acid substitutions, introduction of insertions and deletions (Bragi program), energy-minimization of the new loop regions, energy-minimization of the entire molecule (Amber program) and checking the quality of the model structure (Procheck program).

20 Protein variants were designed.

They were based on the 3D structure models when using *E. coli* polI and Tne polymerase, and based on the amino acid alignments when using the Pfu polymerase.

Production of the Domain Exchange Variants by Genetic Engineering

The N-terminal His tag was inserted by PCR and the domain exchange variants were produced by a modified SOE method (Horton et al. (1989) Gene 77, 61-68), shown in the scheme with the aid of chemically synthesized oligodeoxynucleotides. The respective DNA fragments were separated on an agarose g□l, isolated using the QIAquick gel extraction kit (Qiagen company) according to the protocol supplied and used in PCR reactions I to IV in the subsequent PCR reaction or in the case of the PCR reaction V they were recleaved with the two restriction enzymes whose recognition sequence was located in the flanking primers (EcoRI and Pst I). The ligation of DNA fragments and the production and transformation of competent XLI Blue *E. coli* cells by electroporation was carried out as described by Villbrandt (1995, Dissertation, TU Braunschweig). Several clones were picked out and their plasmid DNA was isolated according to the protocol supplied using the QIAprep Spin Plasmid Kit (Qiagen company). Microbiological working techniques and the formulations for preparing liquid or plate media as well as the establishment of glycerin cultures was carried out as described in the handbook by Sambrook et al. (1989, Molecular cloning—a laboratory manual, Cold Spring Harbor Laboratory, Cold Spring Harbor, N.Y.). The domain exchange variants were expressed at the same rate as the initial protein.

EXAMPLE 2

Purification (for One Chimera)

Purification of the Domain Exchange Variants

All domain exchange variants were isolated by the same protocol from *Escherichia coli* XLI-Blue. The fermentation was carried out for 16 hours at 37° C. on a one litre scale in LB medium/100 mg/ml ampicillin/12.5 mg/ml tetraycycline/1 mM IPTG. The cells were centrifuged, taken up in 20 ml lysis buffer (50 mM Tris-HCl, pH 8.5, 10 mM 2-mercaptoethanol, 1 mM PMSF), frozen at −70° C. for at least 16 hours and treated for 10 minutes with ultrasound. The cell debris was centrifuged and the sterile-filtered supernatant was applied to an Ni-NTA (nickel-nitriloacetic acid) agarose column (Qiagen) with a column volume of 3.5 ml (r=0.65 cm, h=2.7 cm). It was washed with 40 ml buffer A (20 mM Tris-HCl, pH 8.5, 100 mM KCl, 20 mM imidazole, 10 mM 2-mercaptoethanol, 10% (v/v) glycerol), subsequently with 10 ml buffer B (20 mM Tris-HCl, pH 8.5, 1 M KCl, 20 mM imidazole, 10 mM 2-mercaptoethanol, 10% (v/v) glycerol) and again with 10 ml buffer A. It was eluted with 15 ml buffer C (20 mM Tris-HCl, pH 8.5, 100 mM KCl, 100 mM imidazole, 10 mM 2-mercaptoethanol, 10% (v/v) glycerol). The flow rate was 0.5 ml/minute and the fraction size was 10 ml with the wash fractions and 1 ml for the elution fractions. The combined fractions were dialysed against storage buffer (20 mM Tris-HCl pH 8.0, 100 mM KCl, 0.1 mM EDTA, 1 mM DTT, 0.5% Tween 20, 50% glycerol) and 200 µg/ml gelatin and Nonidet P40 at a final concentration of 0.5% were added. The protein solutions were stored at −20° C.

The analysis of the purification of the domain exchange variant TaqEc1 on Ni-NTA agarose is shown in FIG. 7.

Determination of the Protein Concentration

Figure 8:
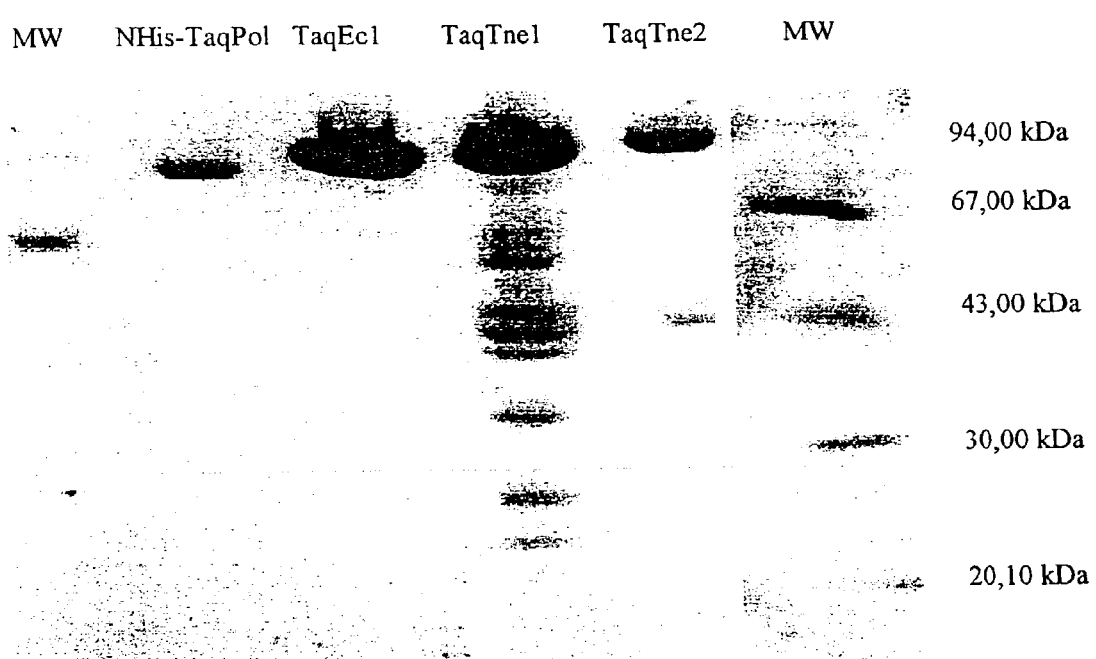

The protein concentrations were determined by measuring the $OD_{280}$ and with the protein assay ESL (Boehringer Mannheim). FIG. 8 shows the determination of the protein purity: SDS-PAGE, Phast system (10-15%): silver staining.

EXAMPLE 3

Temperature Optimum of the Polymerase Activity of the Chimeras

The polymerase activities of the chimeras were determined in a non-radioactive test system. A radioactive test system was used to adjust the values. The incorporation rate of Dig-dUTP into DN'ase-activated calf thymus DNA was determined in the non-radioactive test system. A 50 µl test mix contained 5 µl buffer mix (500 mM Tris-HCl, 150 mM $(NH_4)_2SO_4$, 100 mM KCl, 70 mM $MgCl_2$, 100 mM 2-mercaptoethanol, pH 8.5), 100 µM each of dATP, dCTP, dGTP, dTTP, 36 nM Dig-dUTP (Boehringer Mannheim), 12 µg calf thymus DNA (DN'ase-activated), 10 µg bovine serum albumin and 2 µl chimeric enzyme or 0.02 units Taq polymerase (Boehringer Mannheim) as a reference in dilution buffer (20 mM Tris-HCl, pH 8.0, 100 mM KCl, 0.1 mM EDTA, 1 mM DTT, 200 µg/ml gelatin, 0.5% Tween 20, 0.5% Nonidet P40, 50% glycerol). The reaction mixtures were incubated for 30 minutes at various temperatures. The reactions were stopped on ice. 5 µl of each reaction mixture was pipetted into white membrane-coated microtitre plates (Pall BioSupport, SM045BWP) and baked for 10 minutes at 70° C. The membrane of the microtitre plate was treated as follows using the accompanying suction trough (Pall Bio Support): apply 100 µl buffer 1 (1% blocking reagent (Boehringer Mannheim) in 0.1 M maleic acid, 0.15 M NaCl, pH 7.5), incubate for 2 minutes, suck through, repeat once; apply 100 µl buffer 2 (1:10000 diluted anti-Dig-AP-Fab fragment antibodies (Boehringer Mannheim) in buffer 1), incubate for 2 minutes, suck through, repeat once; apply 200 µl buffer 3 (buffer 1 containing 0.3% Tween 20) under vacuum, repeat once; apply 200 µl buffer 4 (0.1 M Tris-HCl, 0.1 M NaCl, 50 mM $MgCl_2$, pH 9.5) under vacuum; apply 50 µl buffer 5 (1:100 diluted CSPD (Boehringer Mannheim) in buffer 4), incubate for 5 minutes, suck through. The samples were measured in a luminometer (Microluminar LB 96P, Berthold or Wallac Micro Beta Trilux).

In the radioactive test system the incorporation rate of α-[$^{32}$P]dCTP into 1 µgM13 mp9 ss-DNA was determined. A 50 µl test mix contained 5 µl buffer mix (670 mM Tris-HCl, 50 mM MgCl$_2$, 100 mM 2-mercaptoethanol, 2% Tesit, 2 mg/ml gelatin, pH 8.8), 10 µM each of DATP, dGTP, dTTP, 5 µM CTP, 0.1 µCi [α-$^{32}$P]dCTP, 1 µg M13 mp9ss DNA annealed with 0.3 µg M13 primer and 1 µl chimeric enzyme or 0.01 units Taq polymerase (Boehringer Mannheim) as a reference in dilution buffer (20 mM Tris-HCl, pH 8.0, 100 mM KCl, 0.1 mM EDTA, 1 mM DTT, 200 µg/ml gelatin, 0.5% Tween 20, 0.5% Nonidet P40, 50% glycerol). In order to prepare the DNA primer mixture, 277.2 µg M13 mp9ssDNA (Boehringer Mannheim) and 156 µgM13 sequencing primer (17 mer) were heated for 30 minutes to 55° C. and cooled for 30 minutes to room temperature. The reaction mixtures were incubated for 30 minutes at 65° C. The reactions were stopped on ice. 25 µl of each of the reaction solutions was removed and pipetted into 250 µl 10% trichloroacetic acid (TCA)/0.01 M sodium pyrophosphate (PPi), mixed and incubated for 30 minutes on ice. The samples were aspirated over pre-soaked GFC filters (Whatman), the reaction vessels were washed out with 5% TCA/PPi and the filters were washed at least three times with the same solution. After drying, the filters were measured in a β-counter in 5 ml scintillation liquid. The enzyme samples were diluted in enzyme dilution buffer. 1 µl aliquots of the dilutions were used. Duplicate or triplicate determinations were carried out. The Taq DNA polymerase from the Boehringer Mannheim Company was used as a reference.

One unit is defined as the amount of enzyme that is necessary to incorporate 10 nM deoxyribonucleotide triphosphate into acid-precipitatable DNA at 65° C. in 30 minutes. In order to determine the standard values, 2 µl aliquots of the total mixture were pipetted onto a dry filter and dried. The blank value was determined by also incubating samples without enzyme and washing them identically.

The temperature optima were determined using the non-radioactive DNA polymerase test at various temperatures.

Specific activities at various temperatures

| Enzyme | Temperature [° C.] | | | | | |
|---|---|---|---|---|---|---|
| | 25 | 37 | 50 | 60 | 72 | 80 |
| TaqPol (BM) | 0.0 | 0.0 | 5764.4 | 8489.1 | 50000.0 | 57986.1 |
| NHis-TaqPol | 0.0 | 0.0 | 5616.1 | 12165.2 | 60843.7 | 74784.4 |
| TaqEc1 (SEQ ID NO:7) | 704.9 | 10353.4 | 50066.5 | 41034.4 | 2677.5 | 1016.0 |
| TaqTne1 (SEQ ID NO:9) | 0.0 | 2559.4 | 15967.0 | 18900.4 | 1100.0 | 0.0 |
| TaqTne2 | 747.2 | 5180.2 | 23549.6 | 30627.3 | 64139.1 | 28727.4 |

(SEQ ID NO:10)

EXAMPLE 4

Temperature Stability of the Polymerase Activity of the Chimeras

Figure 9:
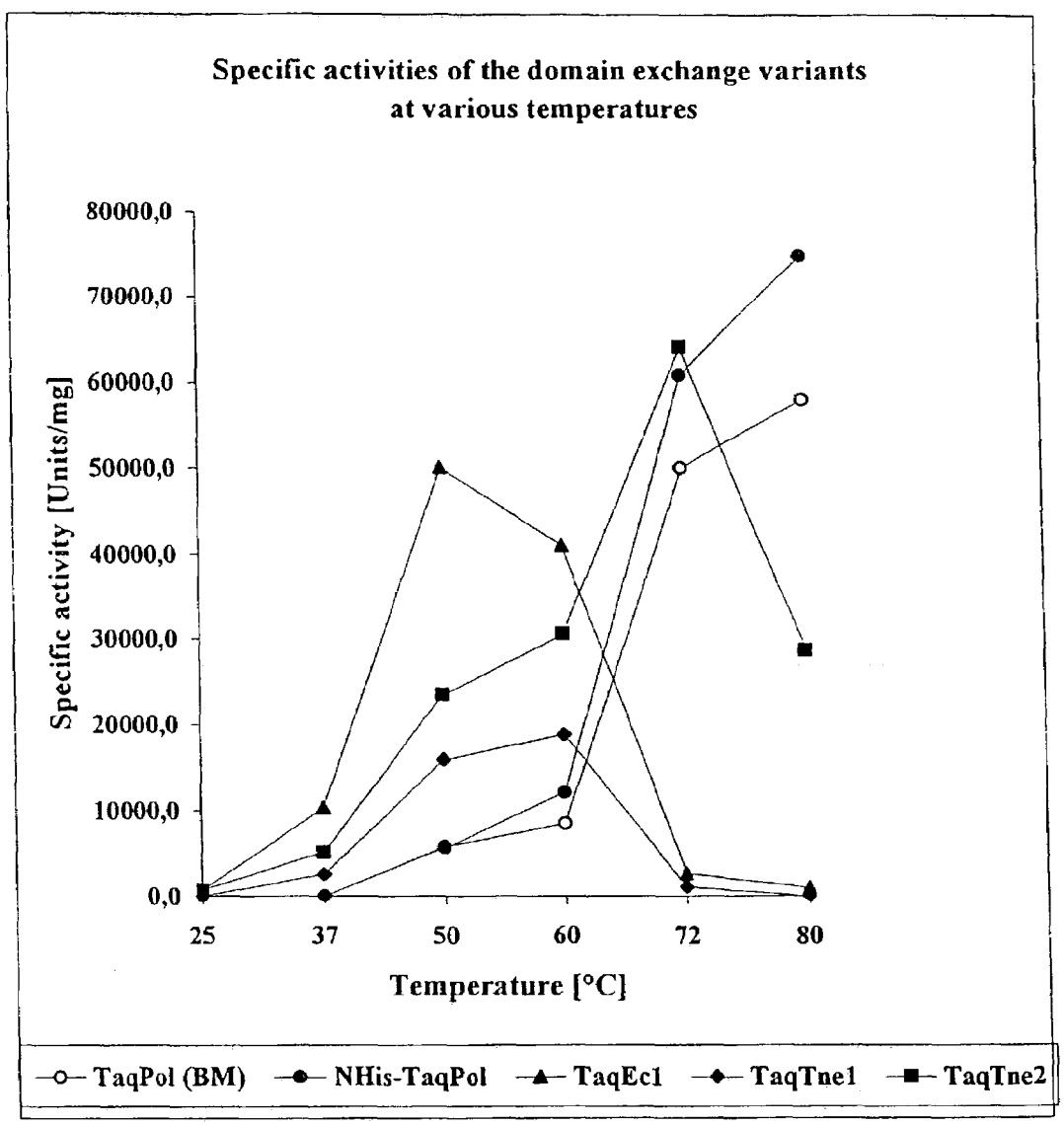

The thermal stability was determined by heating the reaction mixtures to 80° C. and 95° C. for one, three or six minutes and subsequently determining the residual activities using the non-radioactive DNA polymerase test (see FIG. 9).

Table: residual activities (percent of the initial activities without heat treatment (at 72° of the Taq DNA polymerase (TaqPol), the Taq DNA polymerase with a his tag (NHis-TaqPol) and the three domain exchange variants (TaqEc1, TaqTne1, TaqTne2) after heat treatment (incorporation of Dig-dUTP into DN'ase-activated calf thymus DNA).

TABLE residual activities (percent of the initial activity without heat treatment) at 72° C. of the Taq DNA polymerase (TaqPol), the Taq DNA polymerase with a His tag (NHis-TaqPol) and the three domain exchange variants (TaqEc1, TaqTne1, TaqTne2) after heat treatment (incorporation of Dig-dUTP into DN'ase-activated calf thymus DNA).

| Enzyme | 1 min 80° C. | 3 min 80° C. | 6 min 80° C. | 1 min 95° C. | 3 min 95° C. | 6 min 95° C. |
|---|---|---|---|---|---|---|
| TaqPol | 100 | 100 | 100 | 100 | 100 | 100 |
| NHis-TaqPol | 100 | 100 | 100 | 100 | 100 | 100 |
| TaqEc1 (SEQ ID NO:7) | 0 | 0 | 0 | 0 | 0 | 0 |
| TaqTne1 (SEQ ID NO:9) | 16 | 0 | 0 | 0 | 0 | 0 |
| TaqTne2 | 100 | 100 | 100 | 92 | 0 | 0 |

(SEQ ID NO:10)

EXAMPLE 5

PCR with Successive Addition of Enzyme

Figure 10:
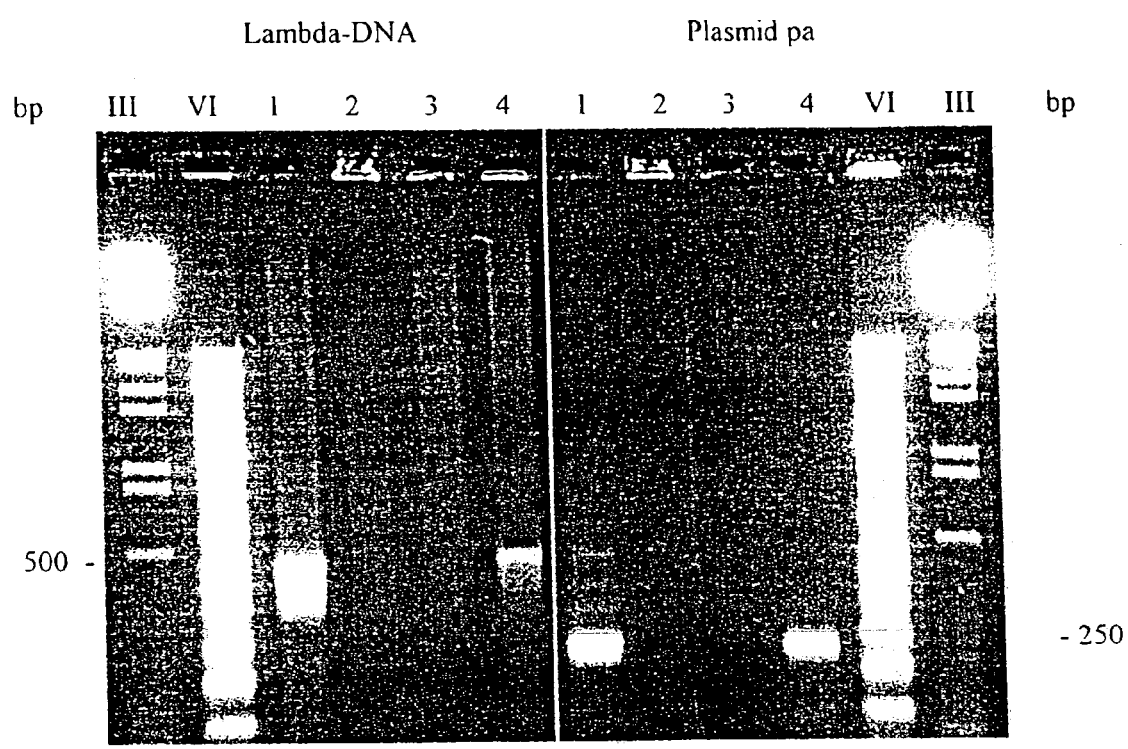
Figure 11:
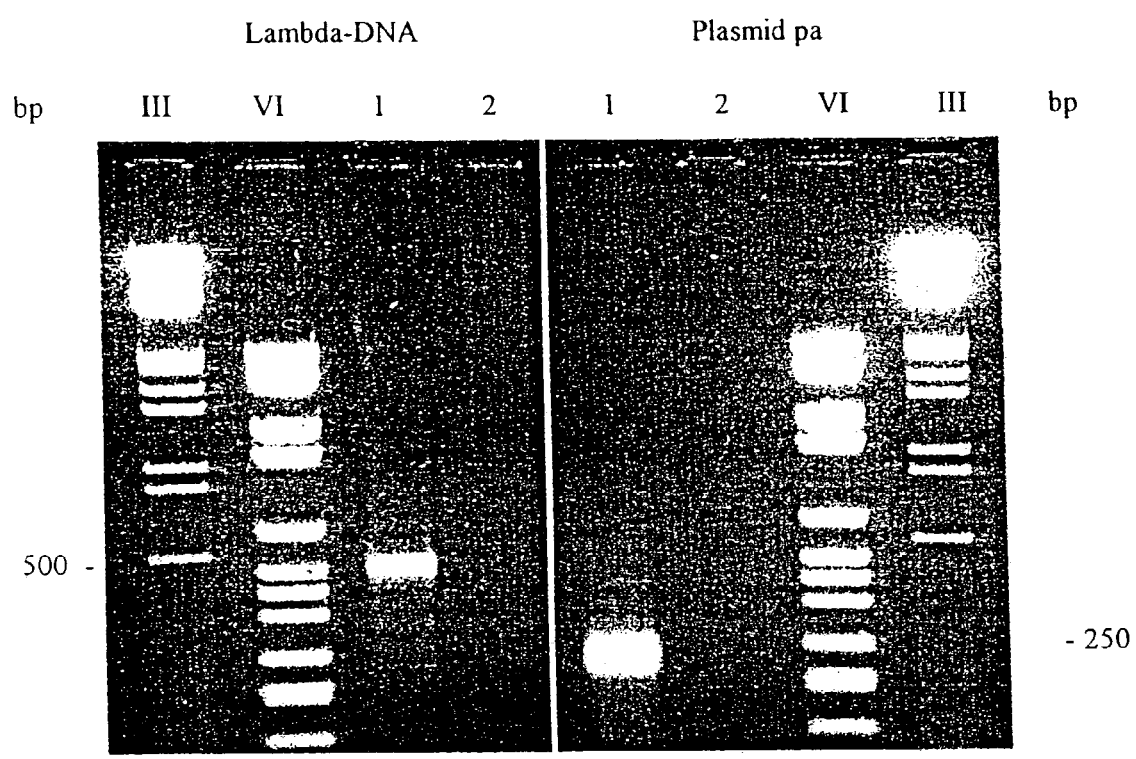

The polymerase chimeras were tested in a PCR with successive addition of enzyme. The extension was carried out at 72° C. (FIG. 10) and at 55° C. (FIG. 11). Each of the reactions mixtures with a reaction volume of 100 µl contained 1 ng lambda DNA or pa-plasmid DNA (BM Co.), 1 µM of each primer (25-mer), 200 µM of each of the dNTPs and standard PCR buffer containing MgCl$_2$ (Boehringer Mannheim). The reaction conditions were:

For extension at 72° C.: 1 minute 94° C./30 seconds 50° C./1 minute 72° C.//25 cycles, 2 minutes at 94° C. before and 7 minutes at 72° C. after the PCR reaction. 0.5 µl of the domain exchange variants was added per cycle at 50° C.

For extension at 55° C.: 1 minute 95° C./30 seconds 50° C./1 minute 55° C.//25 cycles, 2 minutes at 95° C. before and 7 minutes at 55° C. after the PCR reaction. 0.5 µl of the domain exchange variants was added per cycle at 50° C.

EXAMPLE 6

3'-5'exonuclease test-TaqEc1(SEQ ID NO: 1) variant

Figure 12:
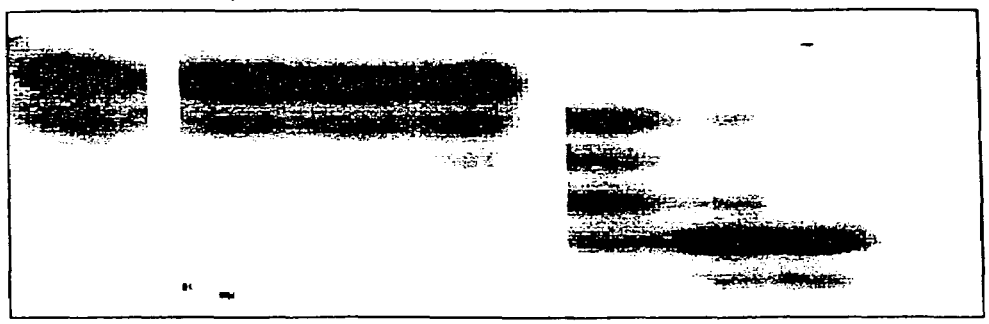
Figure 13:
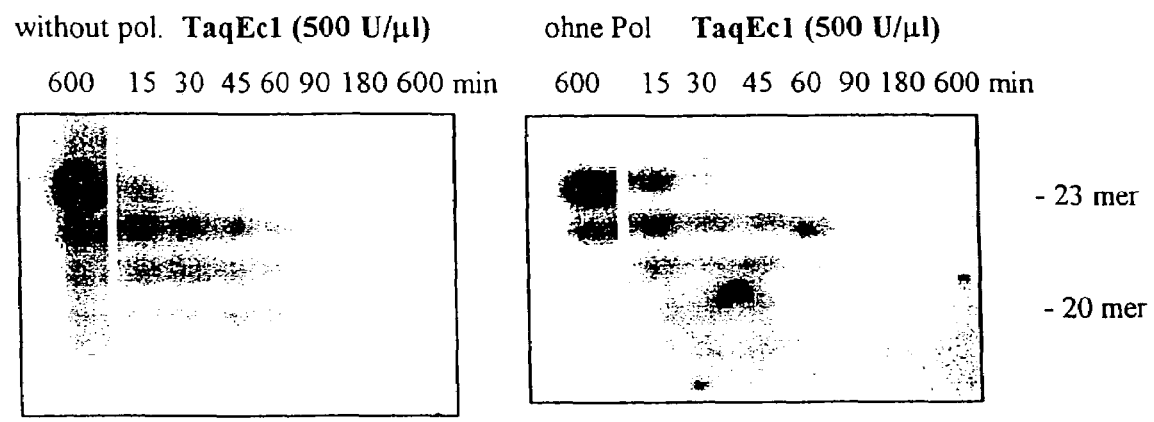

The samples were incubated in the absence of nucleotides with a 5'-Dig-labelled primer which anneals to a DNA template strand. 10 µl test mix contained 1 µl buffer (100 mM Tris-HCl, 15 mM MgCl$_2$, 500 mM KCl, 0.1 mg/ml gelatin, pH 8.3), 1 µl enzyme TaqEc1 (500 units/µl), 1 pmol template strand (50-mer, see scheme) and 500 fmol 5'-Dig-labelled primer P1 (matched, 23 mer, see scheme) or P2 (mismatched, 23 mer, see scheme). The reaction mixtures were incubated at 50° C. for various incubation periods. The DNA fragments were separated on a 12.5% acrylamide gel (SequaGel Kit, Medco Company) and transferred onto a nylon membrane (Boehringer Mannheim) by contact blotting. The nylon membrane was treated as follows: 100 ml buffer 1 (1% blocking reagent (Boehringer Mannheim) in 0.1 M maleic acid, 0.15 M NaCl, pH 7.5), incubate for 30 minutes; 100 ml buffer 2 (1:10000 diluted anti-Dig-AP Fab fragment antibody (Boehringer Mannheim) in buffer 1), incubate for 30 minutes; 135 ml buffer 3 each time (buffer 1 containing 0.3% Tween 20), wash three times for 30 minutes; 50 ml buffer 4 (0.1 M Tris-HCl, 0.1 M NaCl, 50 mM $MgCl_2$, pH 9.5), incubate for 5 minutes; 50 ml buffer 5 (1:1000 diluted CPD star (Boehringer Mannheim) in buffer 4), incubate for 5 minutes. The nylon membrane was dried on Watman paper and exposed for 30 to 60 minutes on a chemiluminescence film (Boehringer Mannheim) for the chemiluminescence detection. If a 3'-5' exonuclease is present, the degradation of the primer at the 3' end is visible (see figures). The Taq polymerase with a His tag (NHis-TaqPol) was used as a negative control and the UITma DNA polymerase was used as a positive control. For both control enzymes the reactions mixtures were incubated at 72° C. The reaction buffer of the manufacturer was used for the UITma DNA polymerase. FIGS. 12 and 13 show the 3'-5' exonuclease test variant TaqEcl.

EXAMPLE 7

Correction of 3'-Mismatched Primers and Their Extension—TaqEc1(SEQ ID NO: 1) Variant (3'-Mismatch Primer Correction Assay)

Figure 14:
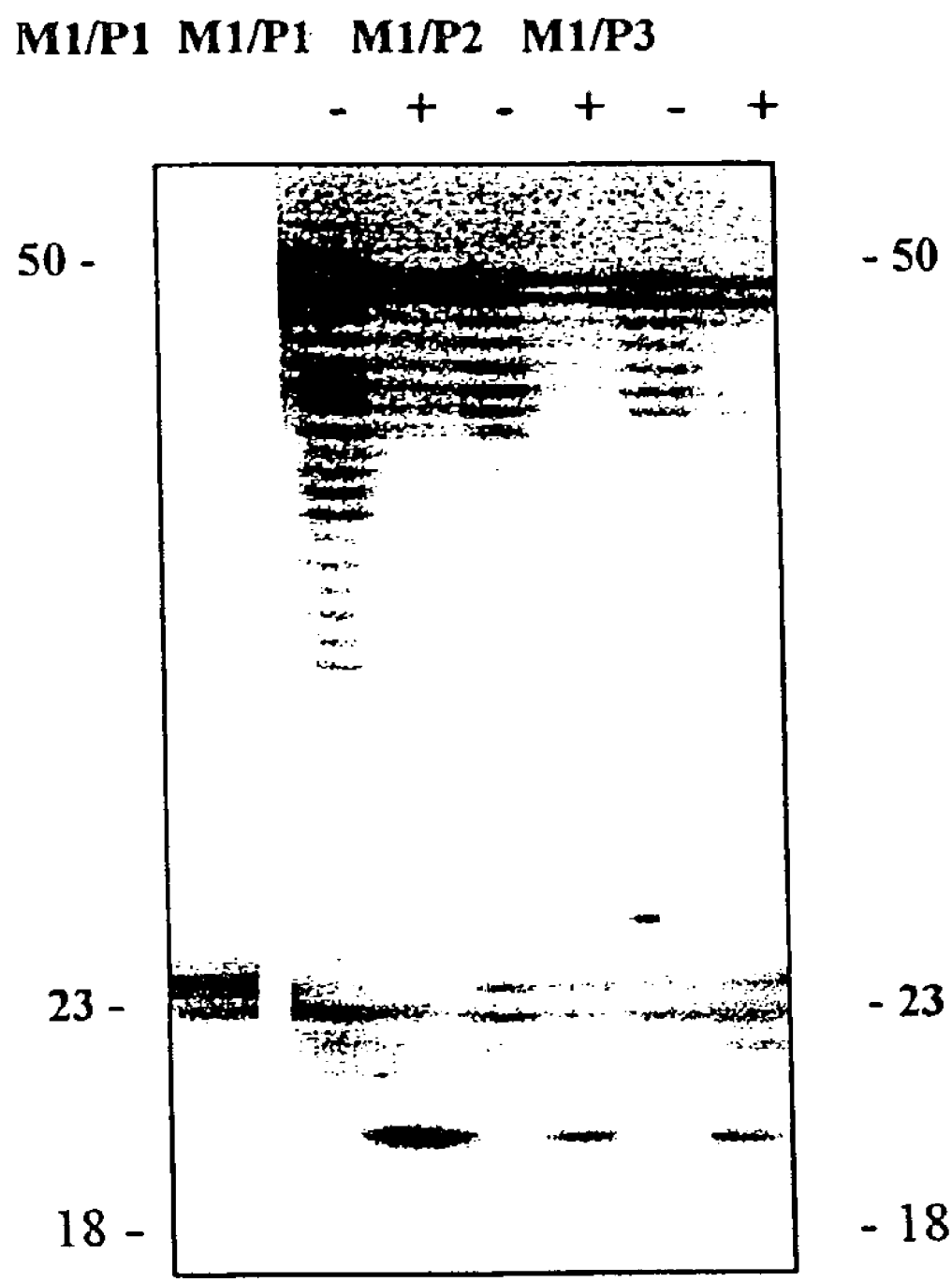
Figure 15:
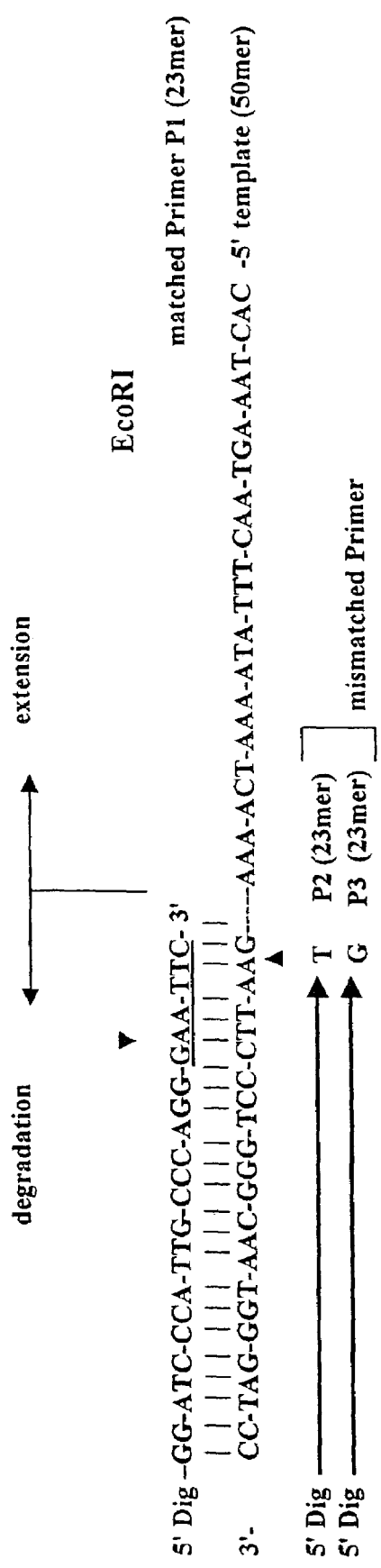
Figure 16:
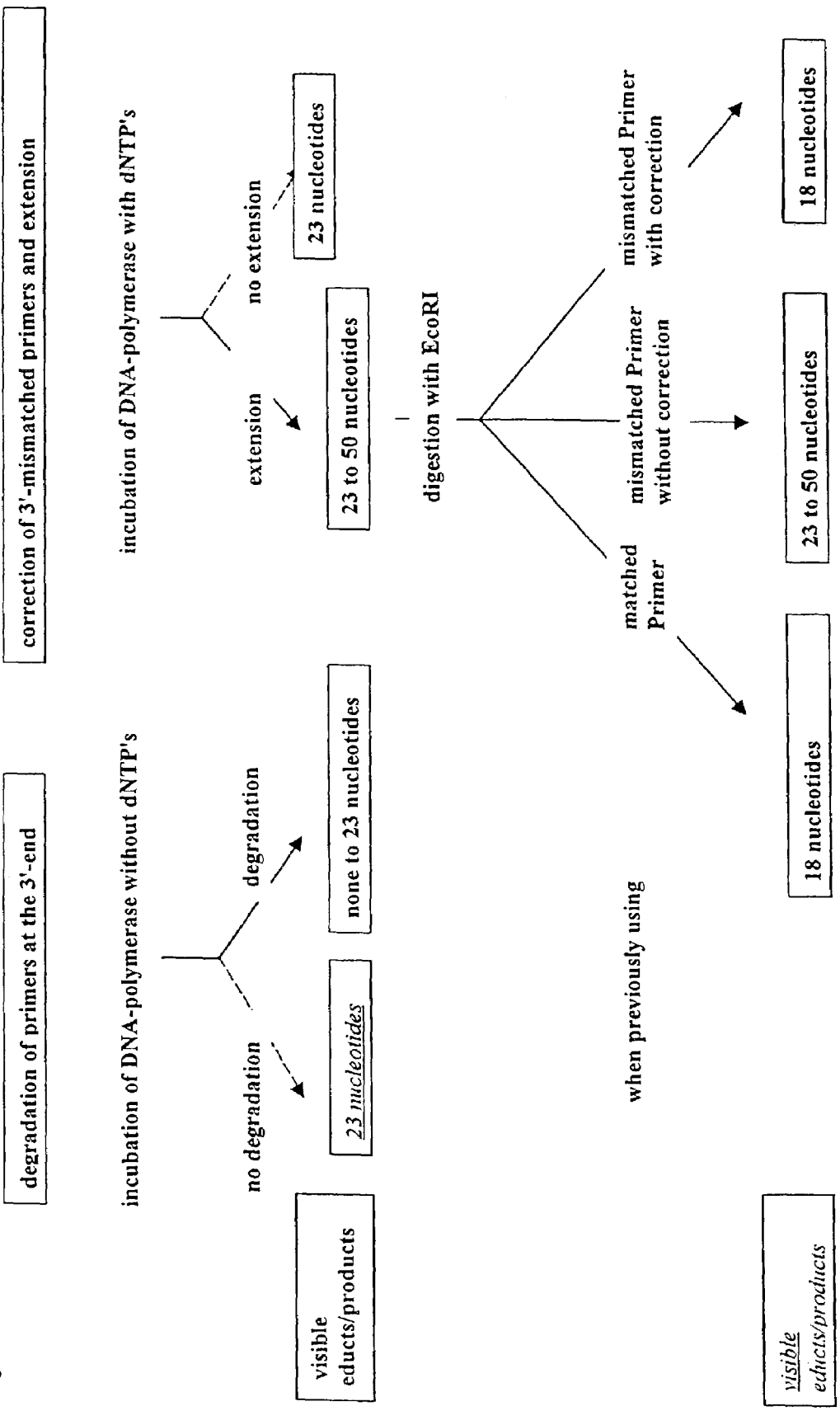

Dig-labelled primers which anneal to a template strand (50 mer, see scheme) were extended in four different experiments. The primers were a matched primer (P1, 23mer, see scheme) and two different mismatched primers (P2, P3, 23mers, see scheme) which anneal in the recognition sequence of the restriction enzyme EcoRI. A 20 µl test mix contained 1 µl buffer (100 mM Tris-HCl, 15 mM $MgCl_2$, 500 mM KCl, 0.1 mg/ml gelatin, pH 8.3), 1 µl enzyme TaqEc1 (500 units/µl), 10 µM each of DATP, dCTP, dGTP, dTTP, 1 pmol template strand and 500 fmol of each 5'-Dig-labelled primer P1 (matched) or P2 (mismatched) or P3 (mismatched). The reaction mixtures were incubated for 60 minutes at 50° C. and afterwards heated for 5 minutes to 95° C. 10 µl aliquots were removed and cleaved for 30 minutes at 37° C. with 10 units EcoRI. The DNA fragments were separated on a 12.5% acrylamide gel (SequaGel Kit, Medco Company) and transferred by contact blot onto a nylon membrane (Boehringer Mannheim). The nylon membrane was treated as described above and exposed for 30 to 60 minutes on a chemiluminescence film (Boehringer Mannheim). When the matched primer was used, the digestion with EcoRI resulted in a 28 bp and a 18 bp fragment. The mismatched primers yield this result only when mismatched nucleotides are replaced by matched nucleotides (see FIG. 14).

EXAMPLE 8

Modification of a Recombinant DNA Polymerase Design of the Hybrid Polymerase Gene Ath Pol and Tne Pol Computer Prediction The structure of the chimeric polymerase gene was derived from the sequence alignment (Thompson, J. D. Higgins, D. G. and Gibson, T. J. Nucleic Acids Research, 1994, 22: 4673-4680) between the polymerases and the E. coli POLI gene—the sequence with the highest correspondence with the resolved 3D structure in the data bank of Brookhaven (for the Klenow fragment). The pair alignments showed a correspondence of ca. 40% and hence the 1KLN structure can presumably be regarded as the best possible prototype. In order to ensure a smooth transition from one structure to the other, the crossing point should be located in an area which has a high similarity with all three proteins from the point of view of multiple alignments. The crossing point should therefore be between the polymerase and 3'-5' exonuclease domain (FIGS. 17, 18).

Construction of a Hybrid Polymerase Gene and Expression Vectors.

Computer predictions and simulations serve as a basis for the construction of a hybrid gene. PCR amplification and subcloning were used as methods to obtain the ATH POL and TNE EXO domains in which two primer pairs having the structure shown in FIG. 18 were used. The primers have sequences which are specific for the N- and C-ends of the respective genes and for the connecting sequence in the middle of the gene as shown in FIGS. 2B, C. The overlap of 12 bases in the ATHUP and TNELOW primers was designed for the subsequent reconstruction of the hybrid gene and, furthermore, inserted in an unequivocal SalI restriction site which can be used for further modifications with polymerase domains. The overhangs of the 5' sequence of the TNEUP and ATHLOW primers code for the restriction sites NcoI and HindIII for the later subcloning of the required fragments in the expression vector.

However, applying this strategy requires extensive sequencing of the subcloned regions. For this reason an additional construct was built and the splice connection between the genes was moved to another position i.e. 42 amino acids further below the original connecting position to a region between the polymerases which has a higher similarity. An advantage of the new design is the unequivocal BamHI sequence within the TNE polymerase sequence containing the proposed splice connection. In order to construct the hybrid gene, a BamHI sequence was incorporated into the ATH polymerase sequence which is subsequently used to assemble parts of the gene by a directed mutagenesis. The amino acids and nucleotide sequence of the new compound is shown in FIG. 19.

Figure 20:
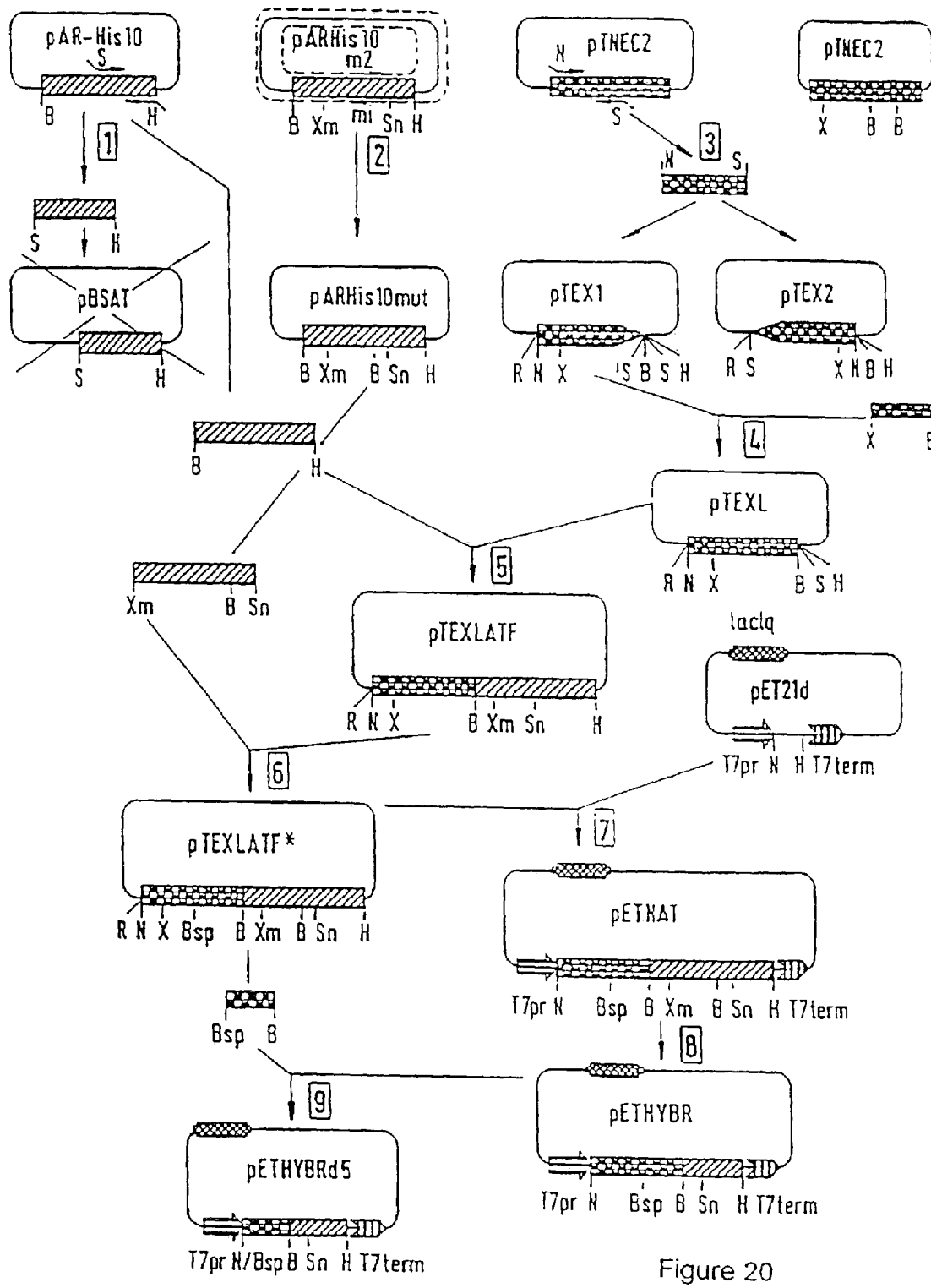

The hybrid polymerase gene was constructed as described in FIG. 20 by multiple subcloning, directed mutagenesis and sequencing steps.

All fragments obtained by the PCR amplification were sequenced starting at the ends up to the unequivocal restriction sites used in the subsequent subcloning steps. In order to ensure the accuracy of the amplification the PCR reactions were carried out with Vent polymerase (New England Biolabs). The directed mutagenesis was carried out using the "Quick Change" method (Stratagene).

EXAMPLE 9

Expression of a Hybrid Polymerase Gene in *E. coli*

The plasmids PETHYBR and pETHYBRd5 were transformed in the *E. coli* strain BL21 (DE3) plySS from Novagene and led to the expression of T7 polymerase.

The expression of the hybrid POL gene was monitored in the extracts of recombinant strains by measuring the DNA polymerase activity using the activated DNA assay. The following conditions were used.

1) The recombinant *E. coli* strains were cultured in LB medium containing 100 mcg/ml ampicillin+30 mcg/ml chloroamphenicol (for pETHYBR and pETHYBRd5 in BL21 (DE3) plyss) or in 20 ml LB medium containing 100 mcg/ml ampicillin+30 mcg/ml kanamycin (pAR-HYBd5 in JM109/pSB1611).
2) The cultures were shaken at 37° C. to an optical density of OD 550~0.6-0.7; then the cultures were cooled to 25°-28° C., IPTG was added to a final concentration of 1 mM. The incubation was then continued at 25-30° C.: For two pET vectors the density of non-induced cultures after 4 hours incubation was OD 550~2.2 and for induced cultures ~1.5.

3) Protein extracts of BL21 (DE3) plyss strains were produced by pelleting 5 ml aliquots of the cultures; the cell pellets were then resuspended in 100 µl termination buffer containing 40 mM Tris-HCl, pH 8.0, 0.1 mM EDTA, 7 mM 2-mercaptoethanol, 0.2 mM PMSF, 0.1% Triton X-100. The cell extracts were prepared by freezing and thawing the cell suspension in two cycles in liquid nitrogen/warm water bath; then a KCl solution was added to a final concentration of 0.75 M and the extracts of the induced and non-induced cultures were heated for 15 min at 72° C., pelleted and used to measure the polymerase activity; this was carried out in an activated DNA assay (100 mcg/ml activated DNA, 3 mM $MgSO_4$, 50 mM Tris-HCl, pH 8.9, 0.1% Triton X-100, 70 µM dA-P33, 5-10 µCi/ml) in a volume of 20 µl using 2 µl heated cell extracts.

The results are shown in the following table:

Relative DNA polymerase activity in extracts of recombinant strains (% incorporation of labels, mean of 3 independent measurements)

| Strain plasmid | BL21 (DE3) plyS pETHYBR | | pETHYBRd5 | |
|---|---|---|---|---|
| IPTG | − | + | − | + |
| TCA insoluble r/a | 5 | 40 | 2 | 85 |

These data show that both versions of the hybrid polymerase gene could be expressed with the pET vector system.

Characterization of the recombinant hybrid polymerase.

Thermal Stability

The thermal stability of recombinant polymerases was determined by heating the extract of the *E. coli* strain for various periods (10, 30, 60, 120 minutes) at 95° C. It turned out that the completely formed as well as the shortened hybrid polymerase were not sufficiently stable (100% inactive after a 10 minute incubation at 95° C.). The degree of expression of the recombinant polymerases was evaluated by analysing the heated cell extracts in 10% SDS PAAG; since no visible difference was found between the induced and non-induced cultures, it may be concluded that the production of hybrid polymerases does not exceed 1% of the total soluble protein.

Proof-reading Activity

The proof-reading activity of the recombinant DNA polymerase derived from pETHYBRd5, e.g. Klenow fragment was tested according to the same protocol which was also used for the archaeal DNA. It turned out that the recombinant enzyme has proof reading activity.

Reverse Transcriptase Activity

The following reaction mixture was used to determine the reverse transcriptase activity: 1 µg polydA-(dT)$_{15}$ (SEQ ID NO:49), 330 µM TTP, 0.36 µM digoxigenin-dUTP, 200 µg/ml BSA, 10 mM Tris HCl, pH 8.5, 20 mM KCl. The concentration of $MgCl_2$ in the reaction mixture varied between 0.5 and 10 mM. DTE was added at a concentration of 10 mM.

2 µl recombinant DNA polymerase (derived from pETHYBRd5, e.g. Klenow fragment) was added to the reaction mixture and incubated for 15 min at 50° C. Tth DNA polymerase containing $Mn^{2+}$ was added as a positive control. After stopping the reaction, the mixture was applied to a positively charged nylon membrane (BM). The incorporated digoxigenin was detected by means of the BM protocol, 1995.

It turned out that the recombinant enzymes (Klenow fragment) have reverse transcriptase activity (FIG. 22). The activity is dependent on the presence of $Mn^{2+}$ (optimal concentration 1 mM). The presence of $Mg^{2+}$ had moreover an additional stimulating effect (optimal $Mg^{2+}$ concentration 4 mM).

EXAMPLE 11

Construction of the Chimeric Polymerase Gene (see FIG. 20)

Abbreviations for the restriction sequences—B-BamHI, Bsp-BspHI, H-HindIII, N-NcoI, R-EcoRI, S-SalI, Sn-SnaI, X-XhoI, Xm-XmaI 1. PCR amplification of the ATH POL domain using the primers ATH UP and ATHLOW and the pARHis10 plasmid containing the complete polymerase gene in the vector pTrcHISB and subcloning in the pSK+Bluescript plasmid→pBSAT. The insertion was sequenced from the flanking primers and it turned out that due to an error during the primer synthesis, a single base in the ATHUP primer sequence had been deleted.

2. Directed mutagenesis of the plasmid pARHis10 with primers m1 and m2 using the "Quick change" procedure (Stratagene) to incorporate the BamHI sequence at position 1535→pARHis10mut.

3. PCR amplification of the TNE EXO domain using the primers TNEUP and TNELOW on the template of the pTNEC2 plasmid and subcloning in the SmaI cut puC19 plasmid→pTEX1 and pTEX2 with different orientations of the incorporation.

3. Subcloning the 1444 bp XhoI-BamHI fragment from the pTNEC2 plasmid containing the "LONG" EXO domain in the XhoI-BamHI cut plasmid pTEX1→pTEXL.

5. Incorporation of the complete ATH polymerase gene as a 2553 bp BamHI-HindII fragment in BamHI-HindIII cut pTEXL→pTEXLATF.

6. Substitution of the XmaI-SnaI fragment of the pTEX-LATF plasmid by the 1094 bp XmaI-SnaI fragment from the pARHis10mut plasmid containing the incorporated BamHI sequence→pTEXLATF*.

7. Incorporation of the 4214 bp NcoIHindII fragment from PTEXLATF* into the NcoI-HindII cut pET21d vector→pETNAT.

8. Deletion of the 1535 bp BamHI fragment coding for the N-terminal domain of the ATH polymerase from the PETNAT plasmid; this leads to an in-frame joining of the TNE EXOL and ATH POL sequences→PETHYBR.

9. Substitution of the 1661 bp NcoI-BamHI fragment of pETHYBR by the 829 bp BspHI-BamHI fragment from PETNAT; this leads to the use of Met284 of the TNE polymerase as the starting codon and to deletion of the N-terminal domain with the assumed 5'-3' exonuclease activity→pETHYBRd5.

What is claimed is:

1. A polymerase chimera comprising the amino acid sequence of SEQ ID NO: 12.

2. The polymerase chimera as claimed in claim 1, wherein the chimera additionally has reverse transcriptase activity.

3. The polymerase of claim 2, wherein histidine tags have been incorporated in the amino acid sequence of the chimera.

4. A kit comprising the polymerase chimera of claim 1.

* * * * *

SEQUENCE LISTING

<160> NUMBER OF SEQ ID NOS: 44

<210> SEQ ID NO 1
<211> LENGTH: 2733
<212> TYPE: DNA
<213> ORGANISM: Artificial Sequence
<220> FEATURE:
<223> OTHER INFORMATION: Description of Artificial Sequence: polynucleotide

<400> SEQUENCE: 1

| | | | | | |
|---|---|---|---|---|---|
| atgaggggct | cgcatcacca | tcaccatcac | gctgctgacg | atgacgataa | aatgaggggc | 60 |
| atgctaccgc | tatttgagcc | caagggccgg | gtcctcctgg | tcgacggcca | ccacctggcc | 120 |
| taccgcacct | tccacgccct | gaagggcctc | accaccagcc | gggggagcc | ggtgcaggcg | 180 |
| gtctacggct | tcgccaagag | cctcctcaag | gccctcaagg | aggacgggga | cgcggtgatc | 240 |
| gtggtctttg | acgccaaggc | cccctccttc | cgccacgagg | cctacggggg | gtacaaggcg | 300 |
| ggccgggccc | ccacgccgga | ggactttccc | cggcaactcg | ccctcatcaa | ggagctggtg | 360 |
| gacctcctgg | ggctggcgcg | cctcgaggtc | ccgggctacg | aggcggacga | cgtcctggcc | 420 |
| agcctggcca | agaaggcgga | aaaggagggc | tacgaggtcc | gcatcctcac | cgccgacaaa | 480 |
| gacctttacc | agctcctttc | cgaccgcatc | cacgtcctcc | accccgaggg | gtacctcatc | 540 |
| accccggcct | ggctttggga | aaagtacggc | ctgaggcccg | accagtgggc | cgactaccgg | 600 |
| gccctgaccg | gggacgagtc | cgacaacctt | cccggggtca | agggcatcgg | ggagaagacg | 660 |
| gcgaggaagc | ttctgaggag | gtggggagc | ctggaagccc | tcctcaagaa | cctggaccgg | 720 |
| ctgaagcccg | ccatccggga | agatcctg | cccacatgg | acgatctgaa | gctctcctgg | 780 |
| gacctggcca | aggtgcgcac | cgacctgccc | ctggaggtgg | acttcgccaa | aaggcgggag | 840 |
| cccgaccggg | agaggcttag | ggccttctg | gagaggcttg | agtttggcag | cctcctccac | 900 |
| gagttcggcc | ttctggaaag | ccctatgac | aactacgtca | ccatccttga | tgaagaaaca | 960 |
| ctgaaagcgt | ggattgcgaa | gctggaaaaa | gcgccggtat | ttgcatttga | taccgaaacc | 1020 |
| gacagccttg | ataacatctc | tgctaacctg | gtcgggcttt | cttttgctat | cgagccaggc | 1080 |
| gtagcggcat | atattccggt | tgctcatgat | tatcttgatg | cgcccgatca | aatctctcgc | 1140 |
| gagcgtgcac | tcgagttgct | aaaaccgctg | ctggaagatg | aaaaggcgct | gaaggtcggg | 1200 |
| caaaacctga | aatacgatcg | cggtattctg | gcgaactacg | gcattgaact | gcgtgggatt | 1260 |
| gcgtttgata | ccatgctgga | gtcctacatt | ctcaatagcg | ttgccgggcg | tcacgatatg | 1320 |
| gacagcctcg | cggaacgttg | gttgaagcac | aaaaccatca | cttttgaaga | gattgctggt | 1380 |
| aaaggcaaaa | atcaactgac | ctttaaccag | attgccctcg | aagaagccgg | acgttacgcc | 1440 |
| gccgaagatg | cagatgtcac | cttgcagttg | catctgaaaa | tgtggccgga | tctgcaaaaa | 1500 |
| cacgagaggc | tcctttggct | ttaccgggag | gtggagaggc | ccctttccgc | tgtcctggcc | 1560 |
| cacatggagg | ccacgggggt | gcgcctggac | gtggcctatc | tcagggcctt | gtccctggag | 1620 |
| gtggccgagg | aggtcgcccg | cctcgaggcc | gaggtcttcc | gcctggccgg | ccaccccttc | 1680 |
| aacctcaact | cccgggacca | gctggaaagg | gtcctctttg | acgagctagg | gcttccgcc | 1740 |
| atcggcaaga | cggagaagac | cggcaagcgc | tccaccagcg | ccgccgtcct | ggaggccctc | 1800 |
| cgcgaggccc | accccatcgt | ggagaagatc | ctgcagtacc | gggagctcac | caagctgaag | 1860 |
| agcacctaca | ttgaccccct | tccggacctc | atccaccccc | ggacgggccg | cctccacacc | 1920 |

-continued

| | |
|---|---|
| cgcttcaacc agacggccac ggccacgggc aggctaagta gctccgatcc caacctccag | 1980 |
| aacatcccg tccgcacccc gcttgggcag aggatccgcc gggccttcat cgccgaggag | 2040 |
| gggtggctat tggtggccct ggactatagc cagatagagc tcaggtgct ggcccacctc | 2100 |
| tccggcgacg agaacctgat ccgggtcttc caggaggggc gggacatcca cacggagacc | 2160 |
| gccagctgga tgttcggcgt ccccggag gccgtggacc ccctgatgcg ccgggcggcc | 2220 |
| aagaccatca acttcgggt cctctacggc atgtcggccc accgcctctc ccaggagcta | 2280 |
| gccatccctt acgaggaggc ccaggccttc attgagcgct actttcagag cttccccaag | 2340 |
| gtgcgggcct ggattgagaa gaccctggag gagggcagga ggcgggggta cgtggagacc | 2400 |
| ctcttcggcc ccgccgcta cgtgccagac ctagaggccc gggtgaagag cgtgcgggag | 2460 |
| gcggccgagc gcatggcctt caacatgccc gtccagggca ccgccgccga cctcatgaag | 2520 |
| ctggctatgg tgaagctctt ccccaggctg gaggaaatgg gggccaggat gctccttcag | 2580 |
| gtccacgacg agctggtcct cgaggcccca aaagagaggg cggaggccgt ggcccggctg | 2640 |
| gccaaggagg tcatggaggg ggtgtatccc ctggccgtgc ccctggaggt ggaggtgggg | 2700 |
| ataggggagg actggctctc cgccaaggag tga | 2733 |

<210> SEQ ID NO 2
<211> LENGTH: 2733
<212> TYPE: DNA
<213> ORGANISM: Artificial Sequence
<220> FEATURE:
<223> OTHER INFORMATION: Description of Artificial Sequence:
      polynucleotide

<400> SEQUENCE: 2

| | |
|---|---|
| atgaggggct cgcatcacca tcaccatcac gctgctgacg atgacgataa aatgaggggc | 60 |
| atgctaccgc tatttgagcc caagggccgg gtcctcctgg tcgacggcca ccacctggcc | 120 |
| taccgcacct tccacgccct gaaggggcctc accaccagcc gggggagcc ggtgcaggcg | 180 |
| gtctacggct cgccaagag cctcctcaag gccctcaagg aggacgggga cgcggtgatc | 240 |
| gtggtctttg acgccaaggc ccctccttc gccacgagg cctacggggg gtacaaggcg | 300 |
| ggccgggccc ccacgccgga ggactttccc cggcaactcg ccctcatcaa ggagctggtg | 360 |
| gacctcctgg ggctggcgcg cctcgaggtc cgggctacg aggcggacga cgtcctggcc | 420 |
| agcctggcca agaaggcgga aaaggagggc tacgaggtcc gcatcctcac cgccgacaaa | 480 |
| gacctttacc agctcctttc cgaccgcatc cacgtcctcc accccgaggg gtacctcatc | 540 |
| accccggcct ggcttgggga aaagtacggc ctgaggcccg accagtgggc cgactaccgg | 600 |
| gccctgaccg gggacgagtc cgacaacctt cccggggtca agggcatcgg ggagaagacg | 660 |
| gcgaggaagc ttctggagga gtgggggagc ctggaagccc tcctcaagaa cctggaccgg | 720 |
| ctgaagcccg ccatccggga gaagatcctg gcccacatgg acgatctgaa gctctcctgg | 780 |
| gacctggcca aggtgcgcac cgacctgccc ctggaggtgg acttcgccaa aaggcgggag | 840 |
| cccgaccggg agaggcttag ggcctttctg gagaggcttg agtttggcag cctcctccac | 900 |
| gagttcggcc ttctggaaag cccctatgac aactacgtca ccatccttga tgaagaaaca | 960 |
| ctgaaagcgt ggattgcgaa gctggaaaaa gcgccggtat ttgcatttga taccgaaacc | 1020 |
| gacagccttg ataacatctc tgctaacctg gtcgggcttt cttttgctat cgagccaggc | 1080 |
| gtagcggcat atattccggt tgctcatgat tatcttgatg cgcccgatca aatctctcgc | 1140 |
| gagcgtgcac tcgagttgct aaaaccgctg ctggaagatg aaaaggcgct gaaggtcggg | 1200 |

-continued

```
caaaacctga aatacgatcg cggtattctg gcgaactacg gcattgaact gcgtgggatt      1260
gcgtttgata ccatgctgga gtcctacatt ctcaatagcg ttgccgggcg tcacgatatg      1320
gacagcctcg cggaacgttg gttgaagcac aaaaccatca cttttgaaga gattgctggt      1380
aaaggcaaaa atcaactgac ctttaaccag attgccctcg aagaagccgg acgttacgcc      1440
gccgaagatg cagatgtcac cttgcagttg catctgaaaa tgtggccgga tctgcaaaaa      1500
cacaaagggc cgttgaacgt cttcgagaat atcgaaatgc cgctggtgcc ggtgctttca      1560
cgcattgaac gtaacggtgt gcgcctggac gtggcctatc tcagggcctt gtccctggag      1620
gtggccgagg agatcgcccg cctcgaggcc gaggtcttcc gcctggccgg ccacccgttc      1680
aacctcaact cccgggacca gctggaaagg gtcctctttg acgagctagg gcttcccgcc      1740
atcggcaaga cggagaagac cggcaagcgc tccaccagcg ccgccgtcct ggaggccctc      1800
cgcgaggccc accccatcgt ggagaagatc ctgcagtacc gggagctcac caagctgaag      1860
agcacctaca ttgacccctt gccggacctc atccaccccca ggacgggccg cctccacacc      1920
cgcttcaacc agacggccac ggccacgggc aggctaagta gctccgatcc caacctccag      1980
aacatccccg tccgcacccc gcttgggcag aggatccgcc gggccttcat cgccgaggag      2040
gggtggctat tggtggccct ggactatagc cagatagagc tcagggtgct ggcccacctc      2100
tccggcgacg agaacctgat ccgggtcttc caggaggggc gggacatcca cacgagacc      2160 gccagctgga tgttcggcgt cccccgggag gccgtggacc ccctgatgcg ccgggcggcc      2220
aagaccatca acttcgggt cctctacggc atgtcggcc accgcctctc ccaggagcta      2280
gccatccctt acgaggaggc ccaggccttc attgagcgct actttcagag cttccccaag      2340
gtgcgggcct ggattgagaa gaccctggag gagggcagga ggcgggggta cgtggagacc      2400
ctcttcggcc gccgccgcta cgtgccagac ctagaggccc gggtgaagag cgtgcgggag      2460
gcggccgagc gcatggcctt caacatgccc gtccagggca ccgccgccga cctcatgaag      2520
ctggctatgg tgaagctctt ccccaggctg gaggaaatgg gggccaggat gctccttcag      2580
gtccacgacg agctggtcct cgaggcccca aaagagaggg cggaggccgt ggcccggctg      2640
gccaaggagg tcatggaggg ggtgtatccc ctggccgtgc ccctggaggt ggaggtgggg      2700
ataggggagg actggctctc cgccaaggag tga                                  2733
```

<210> SEQ ID NO 3
<211> LENGTH: 2727
<212> TYPE: DNA
<213> ORGANISM: Artificial Sequence
<220> FEATURE:
<223> OTHER INFORMATION: Description of Artificial Sequence:
      polynucleotide

<400> SEQUENCE: 3

```
atgaggggct cgcatcacca tcaccatcac gctgctgacg atgacgataa aatgaggggc        60
atgctaccgc tatttgagcc caagggccgg gtcctcctgg tcgacggcca ccacctggcc       120
taccgcacct tccacgccct gaagggcctc accaccagcc ggggggagcc ggtgcaggcg       180
gtctacggct cgccaagag cctcctcaag gccctcaagg aggacgggga gcggtgatc         240 gtggtctttg acgccaaggc cccctccttc cgccacgagg cctacggggg gtacaaggcg       300
ggccgggccc ccacgccgga ggactttccc cggcaactcg ccctcatcaa ggagctggtg       360
gacctcctgg ggctggcgcg cctcgaggtc ccggggctacg aggcggacga cgtcctggcc     420
agcctggcca agaaggcgga aaaggagggc tacgaggtcc gcatcctcac cgccgacaaa       480
```

-continued

```
gacctttacc agctcctttc cgaccgcatc cacgtcctcc accccgaggg gtacctcatc        540
accccggcct ggctttggga aaagtacggc ctgaggcccg accagtgggc cgactaccgg        600
gccctgaccg gggacgagtc cgacaacctt cccggggtca agggcatcgg ggagaagacg        660
gcgaggaagc ttctggagga gtgggggagc ctggaagccc tcctcaagaa cctggaccgg        720
ctgaagcccg ccatccggga gaagatcctg gcccacatgg acgatctgaa gctctcctgg        780
gacctggcca aggtgcgcac cgacctgccc ctggaggtga cttcgccaa aaggcgggag         840 cccgaccggg agaggcttag ggcctttctg gagaggcttg agtttggcag cctcctccac        900
gagttcggcc ttctggaaag ccccccgtt ggatacagaa tagtgaaaga cctggtggaa         960
tttgaaaaac tcatagagaa actgagagaa tcccttcgt tcgccataga tcttgagacg         1020
tcttccctcg atcctttcga ctgcgacatt gtcggtatct ctgtgtcttt caaaccaaag        1080
gaagcgtact acataccact ccatcataga aacgcccaga acctggatga aaaagaagtt        1140
ctgaaaaagc taaagaaat cctggaggac cccggagcaa agatcgttgg tcagaatttg         1200
aaattcgatt acaaggtgtt gatggtaaag ggtgttgaac ctgtccctcc tcacttcgac        1260
acgatgatag cggcttacct tcttgagccg aacgaaaaga agttcaatct ggacgatctc        1320
gcattgaaat tcttggata caaaatgacc tcttaccagg aactcatgtc cttctcttct         1380
ccgctgtttg gtttcagttt tgccgatgtt cctgtagaaa aagcagcgaa ctattcctgt        1440
gaagatgccg acatcaccta cagactctac aagatcctga gcttaaaact ccacgaggag        1500
aggctccttt ggctttaccg ggaggtggag aggcccctt ccgctgtcct ggcccacatg         1560
gaggccacgg gggtgcgcct ggacgtggcc tatctcaggg ccttgtccct ggaggtggcc        1620
gaggagatcg cccgcctcga ggccgaggtc ttccgcctgg ccggccaccc cttcaacctc        1680
aactcccggg accagctgga aagggtcctc tttgacgagc tagggcttcc cgccatcggc        1740
aagacggaga agaccggcaa gcgctccacc agcgccgccg tcctggaggc cctccgcgag        1800
gcccacccca tcgtggagaa gatcctgcag taccgggagc tcaccaagct gaagagcacc        1860
tacattgacc ccttgccgga cctcatccac cccaggacgg gccgcctcca cacccgcttc        1920
aaccagacgg ccacggccac gggcaggcta agtagctccg atcccaacct ccagaacatc        1980
cccgtccgca ccccgcttgg gcagaggatc cgccgggcct tcatcgccga ggaggggtgg        2040
ctattggtgg ccctggacta tagccagata gagctcaggg tgctggccca cctctccggc        2100
gacgagaacc tgatccgggt cttccaggag gggcgggaca tccacacgga gaccgccagc        2160
tggatgttcg gcgtcccccg ggaggccgtg gaccccctga tgcgccgggc ggccaagacc        2220
atcaacttcg gggtcctcta cggcatgtcg gccaccgcc tcccaggga gctagccatc         2280 ccttacgagg aggcccaggc cttcattgag cgctactttc agagcttccc caaggtgcgg        2340
gcctggattg agaagaccct ggaggagggc aggaggcggg ggtacgtgga gaccctcttc        2400
ggccgccgcc gctacgtgcc agacctagag gcccgggtga gagcgtgcg ggaggcggcc         2460 gagcgcatgg ccttcaacat gcccgtccag ggcaccgccg ccgacctcat gaagctggct        2520
atggtgaagc tcttccccag gctggaggaa atggggccca ggatgctcct tcaggtccac        2580
gacgagctgg tcctcgaggc cccaaaagag agggcggagg ccgtggcccg gctggccaag        2640
gaggtcatga gggggtgta tccctggcc gtgcccctgg aggtggaggt ggggataggg          2700
gaggactggc tctccgccaa ggagtga                                            2727
```

<210> SEQ ID NO 4
<211> LENGTH: 2727

<212> TYPE: DNA
<213> ORGANISM: Artificial Sequence
<220> FEATURE:
<223> OTHER INFORMATION: Description of Artificial Sequence: polynucleotide

<400> SEQUENCE: 4

| | | | | | |
|---|---|---|---|---|---|
| atgaggggct | cgcatcacca | tcaccatcac | gctgctgacg | atgacgataa | aatgaggggc | 60 |
| atgctaccgc | tatttgagcc | caagggccgg | gtcctcctgg | tcgacggcca | ccacctggcc | 120 |
| taccgcacct | tccacgccct | gaagggcctc | accaccagcc | gggggagcc | ggtgcaggcg | 180 |
| gtctacggct | tcgccaagag | cctcctcaag | gccctcaagg | aggacgggga | cgcggtgatc | 240 |
| gtggtctttg | acgccaaggc | ccctccttc | cgccacgagg | cctacggggg | gtacaaggcg | 300 |
| ggccgggccc | ccacgccgga | ggactttccc | cggcaactcg | ccctcatcaa | ggagctggtg | 360 |
| gacctcctgg | ggctggcgcg | cctcgaggtc | ccgggctacg | aggcggacga | cgtcctggcc | 420 |
| agcctggcca | agaaggcgga | aaaggagggc | tacgaggtcc | gcatcctcac | cgccgacaaa | 480 |
| gacctttacc | agctccttc | cgaccgcatc | cacgtcctcc | accccgaggg | gtacctcatc | 540 |
| accccggcct | ggctttggga | aaagtacggc | ctgaggcccg | accagtgggc | cgactaccgg | 600 |
| gccctgaccg | gggacgagtc | cgacaacctt | cccggggtca | agggcatcgg | ggagaagacg | 660 |
| gcgaggaagc | ttctggagga | gtgggggagc | ctggaagccc | tcctcaagaa | cctgaccgg | 720 |
| ctgaagcccg | ccatccggga | aagatcctg | gcccacatgg | acgatctgaa | gctctcctgg | 780 |
| gacctggcca | aggtgcgcac | cgacctgccc | ctggaggtgg | acttcgccaa | aaggcgggag | 840 |
| cccgaccggg | agaggcttag | ggcctttctg | gagaggcttg | agtttggcag | cctcctccac | 900 |
| gagttcggcc | ttctggaaag | cccccccgtt | ggatacagaa | tagtgaaaga | cctggtggaa | 960 |
| tttgaaaaac | tcatagagaa | actgagagaa | tcccttcgt | tcgccataga | tcttgagacg | 1020 |
| tcttccctcg | atccttcga | ctgcgacatt | gtcggtatct | ctgtgtcttt | caaaccaaag | 1080 |
| gaagcgtact | acataccact | ccatcataga | aacgcccaga | acctggatga | aaagaagtt | 1140 |
| ctgaaaaagc | taaagaaat | cctggaggac | cccggagcaa | agatcgttgg | tcagaatttg | 1200 |
| aaattcgatt | acaaggtgtt | gatggtaaag | ggtgttgaac | ctgtccctcc | tcacttcgac | 1260 |
| acgatgatag | cggcttacct | tcttgagccg | aacgaaaaga | agttcaatct | ggacgatctc | 1320 |
| gcattgaaat | ttcttggata | caaaatgacc | tcttaccagg | aactcatgtc | cttctcttct | 1380 |
| ccgctgtttg | gtttcagttt | tgccgatgtt | cctgtagaaa | aagcagcgaa | ctattcctgt | 1440 |
| gaagatgcag | acatcaccta | cagactctac | aagatcctga | gcttaaaact | ccacgaggca | 1500 |
| gatctggaga | acgtgttcta | caagatagaa | atgcctcttg | tgagcgtgct | tgcacggatg | 1560 |
| gaactgaacg | gtgtgcgcct | ggacgtggcc | tatctcaggg | ccttgtccct | ggaggtggcc | 1620 |
| gaggagatcg | cccgcctcga | ggccgaggtc | ttccgcctgg | ccggccaccc | cttcaacctc | 1680 |
| aactcccggg | accagctgga | aagggtcctc | tttgacgagc | tagggcttcc | cgccatcggc | 1740 |
| aagacggaga | agaccggcaa | gcgctctacc | agcgccgccg | tcctggaggc | cctccgcgag | 1800 |
| gcccacccca | tcgtggagaa | gatcctgcag | taccggggagc | tcaccaagct | gaagagcacc | 1860 |
| tacattgacc | ccttgccgga | cctcatccac | cccaggacgg | gccgcctcca | cacccgcttc | 1920 |
| aaccagacgg | ccacgccac | gggcaggcta | agtagctccg | atcccaacct | ccagaacatc | 1980 |
| cccgtccgca | cccgcttgg | gcagaggatc | cgccgggcct | tcatcgccga | ggagggtgg | 2040 |
| ctattggtgg | ccctggacta | tagccagata | gagctcaggg | tgctggccca | cctctccggc | 2100 |
| gacgagaacc | tgatccgggt | cttccaggag | gggcgggaca | tccacacgga | gaccgccagc | 2160 |

-continued

```
tggatgttcg cgtcccccg ggaggccgtg gaccccctga tgcgccgggc ggccaagacc      2220
atcaacttcg gggtcctcta cggcatgtcg gcccaccgcc tctcccagga gctagccatc      2280
ccttacgagg aggcccaggc cttcattgag cgctactttc agagcttccc caaggtgcgg      2340
gcctggattg agaagaccct ggaggagggc aggaggcggg ggtacgtgga gaccctcttc      2400
ggccgccgcc gctacgtgcc agacctagag gcccgggtga gagcgtgcg ggaggcggcc       2460 gagcgcatgg ccttcaacat gcccgtccag ggcaccgccg ccgacctcat gaagctggct      2520
atggtgaagc tcttccccag gctggaggaa atggggggcca ggatgctcct tcaggtccac     2580
gacgagctgg tcctcgaggc cccaaaagag agggcggagg ccgtggcccg gctggccaag      2640
gaggtcatgg aggggtgta tccctggcc gtgcccctgg aggtggaggt ggggataggg        2700
gaggactggc tctccgccaa ggagtga                                          2727
```

<210> SEQ ID NO 5
<211> LENGTH: 2850
<212> TYPE: DNA
<213> ORGANISM: Artificial Sequence
<220> FEATURE:
<223> OTHER INFORMATION: Description of Artificial Sequence:
      polynucleotide

<400> SEQUENCE: 5

```
atgaggggct cgcatcacca tcaccatcac gctgctgacg atgacgataa aatgaggggc       60
atgctaccgc tatttgagcc caagggccgg gtcctcctgg tcgacggcca ccacctggcc      120
taccgcacct tccacgccct gaagggcctc accaccagcc gggggagcc ggtgcaggcg       180 gtctacggct cgccaagag cctcctcaag gccctcaagg aggacgggga cgcggtgatc       240
gtggtctttg acgccaaggc ccctccttc cgccacgagg cctacgggg gtacaaggcg        300 ggccgggccc ccacgccgga ggactttccc cggcaactcg ccctcatcaa ggagctggtg      360
gacctcctgg ggctggcgcg cctcgaggtc ccgggctacg aggcggacga cgtcctggcc      420
agcctggcca gaaggcgga aaaggagggc tacgaggtcc gcatcctcac cgccgacaaa      480
gacctttacc agctcctttc cgaccgcatc cacgtcctcc accccgaggg gtacctcatc      540
accccggcct ggctttggga aaagtacggc ctgaggcccg accagtgggc cgactaccgg      600
gccctgaccg gggacgagtc cgacaacctt ccgggggtca agggcatcgg ggagaagacg      660
gcgaggaagc ttctggagga gtgggggagc ctggaagccc tcctcaagaa cctggaccgg      720
ctgaagcccg ccatccggga agatctcctg gcccacatgg acgatctgaa gctctcctgg      780
gacctggcca aggtgcgcac cgacctgccc ctggaggtgg acttcgccaa aaggcgggag      840
cccgaccggg agaggcttag ggcctttctg gagaggcttg agtttggcag cctcctccac      900
gagttcggcc ttctggaaag cccccatcca gcagttgtgg acatcttcga atacgatatt      960
ccatttgcaa agagatacct catcgacaaa ggcctaatac aatggaggg ggaagaagag      1020 ctaaagattc ttgccttcga tatagaaacc ctctatcacg aaggagaaga gtttggaaaa     1080
ggcccaatta taatgattag ttatgcagat gaaaatgaag caaggtgat tacttggaaa      1140 aacatagatc ttccatacgt tgaggttgta tcaagcgaga gagagatgat aaagagattt     1200
ctcaggatta tcaggagaa ggatcctgac attatagtta cttataatgg agactcattc      1260
gacttcccat atttagcgaa aagggcagaa aaacttggga ttaaattaac cattggaaga     1320
gatggaagcg agcccaagat gcagagaata ggcgatatga cggctgtaga agtcaaggga     1380
agaatacatt tcgacttgta tcatgtaata acaaggacaa taaatctccc aacatacaca     1440
```

```
ctagaggctg tatatgaagc aattttttgga aagccaaagg agaaggtata cgccgacgag      1500
atagcaaaag cctgggaaag tggagagaac cttgagagag ttgccaaata ctcgatggaa      1560
gatgcaaagg caacttatga actcgggaaa gaattccttc caatggaaat tcagctttca      1620
gagaggctcc tttggcttta ccgggaggtg gagaggcccc tttccgctgt cctggcccac      1680
atggaggcca cggggtgcg cctggacgtg gcctatctca gggccttgtc cctggaggtg      1740
gccgaggaga tcgcccgcct cgaggccgag gtcttccgcc tggccggcca ccccttcaac      1800
ctcaactccc gggaccagct ggaaagggtc ctctttgacg agctagggct ccccgccatc      1860
ggcaagacgg agaagaccgg caagcgctcc accagcgccg ccgtcctgga ggccctccgc      1920
gaggcccacc ccatcgtgga gaagatcctg cagtaccggg agctcaccaa gctgaagagc      1980
acctacattg acccccttgcc ggacctcatc caccccagga cgggccgcct ccacacccgc      2040
ttcaaccaga cggccacggc cacgggcagg ctaagtagct ccgatcccaa cctccagaac      2100
atccccgtcc gcaccccgct tgggcagagg atccgccggg ccttcatcgc cgaggagggg      2160
tggctattgg tggccctgga ctatagccag atagagctca gggtgctggc ccacctctcc      2220
ggcgacgaga acctgatccg ggtcttccag gaggggcggg acatccacac ggagaccgcc      2280
agctggatgt tcggcgtccc ccgggaggcc gtggaccccc tgatgcgccg ggcggccaag      2340
accatcaact tcggggtcct ctacggcatg tcggcccacc gcctctccca ggagctagcc      2400
atcccttacg aggaggccca ggccttcatt gagcgctact ttcagagctt ccccaaggtg      2460
cgggcctgga ttgagaagac cctggaggag ggcaggaggc gggggtacgt ggagaccctc      2520
ttcggccgcc gccgctacgt gccagaccta gaggcccggg tgaagagcgt gcgggaggcg      2580
gccgagcgca tggccttcaa catgcccgtc cagggcaccg ccgccgacct catgaagctg      2640
gctatggtga agctcttccc caggctggag gaaatggggg ccaggatgct ccttcaggtc      2700
cacgacgagc tggtcctcga ggccccaaaa gagagggcgg aggccgtggc ccggctggcc      2760
aaggaggtca tggaggggt gtatcccctg gccgtgcccc tggaggtgga ggtggggata      2820
ggggaggact ggctctccgc caaggagtga                                        2850
```

<210> SEQ ID NO 6
<211> LENGTH: 2949
<212> TYPE: DNA
<213> ORGANISM: Artificial Sequence
<220> FEATURE:
<223> OTHER INFORMATION: Description of Artificial Sequence:
      polynucleotide

<400> SEQUENCE: 6

```
atgagggct cgcatcacca tcaccatcac gctgctgacg atgacgataa aatgagggc        60 atgctaccgc tatttgagcc caagggccgg gtcctcctgg tcgacggcca ccacctggcc      120
taccgcacct tccacgccct gaagggcctc accaccagcc gggggagcc ggtgcaggcg       180 gtctacggct cgccaagag cctcctcaag gccctcaagg aggacgggga cgcggtgatc      240
gtggtctttg acgccaaggc cccctccttc cgccacgagg cctacggggg gtacaaggcg      300
ggccgggccc ccacgccgga ggactttccc cggcaactcg ccctcatcaa ggagctggtg      360
gacctcctgg ggctggcgcg cctcgaggtc ccgggctacg aggcggacga cgtcctggcc      420
agcctggcca agaaggcgga aaaggaggc tacgaggtcc gcatcctcac cgccgacaaa      480
gacctttacc agctcctttc cgaccgcatc acgtcctcc accccgaggg gtacctcatc      540
accccggcct ggctttggga aaagtacggc ctgaggcccg accagtgggc cgactaccgg      600
```

```
gccctgaccg gggacgagtc cgacaacctt cccggggtca agggcatcgg ggagaagacg      660
gcgaggaagc ttctggagga gtgggggagc ctggaagccc tcctcaagaa cctggaccgg      720
ctgaagcccg ccatccggga gaagatcctg gcccacatgg acgatctgaa gctctcctgg      780
gacctggcca aggtgcgcac cgacctgccc ctggaggtgg acttcgccaa aaggcgggag      840
cccgaccggg agaggcttag ggcctttctg gagaggcttg agtttggcag cctcctccac      900
gagttcggcc ttctggaaag ccccgttaga gaacatccag cagttgtgga catcttcgaa      960
tacgatattc catttgcaaa gagataccte atcgacaaag gcctaatacc aatggagggg     1020
gaagaagagc taaagattct tgccttcgat atagaaaccc tctatcacga aggagaagag     1080
tttgaaaaag gcccaattat aatgattagt tatgcagatg aaaatgaagc aaaggtgatt     1140
acttggaaaa acatagatct tccatacgtt gaggttgtat caagcgagag agagatgata     1200
aagagatttc tcaggattat cagggagaag gatcctgaca ttatagttac ttataatgga     1260
gactcattcg acttcccata tttagcgaaa agggcagaaa aacttgggat taaattaacc     1320
attggaagag atggaagcga gcccaagatg cagagaatag gcgatatgac ggctgtagaa     1380
gtcaagggaa gaatacattt cgacttgtat catgtaataa caaggacaat aaatctccca     1440
acatacacac tagaggctgt atatgaagca ttttttggaa agccaaagga gaaggtatac     1500
gccgacgaga tagcaaaagc ctgggaaagt ggagagaacc ttgagagagt tgccaaatac     1560
tcgatggaag atgcaaaggc aacttatgaa ctcgggaaag aattccttcc aatggaaatt     1620
cagcttccaa gattagttgg acaaccttta tgggatgttt caaggtcaag cacagggaac     1680
cttgtagagt ggttcttact taggaaagcc tacgaaagaa acgaagtagc tccaaacaag     1740
ccaagtgaag aggagtatca agaaggctc agggagagct acacaggtgg attcgtgcgc     1800
ctggacgtgg cctatctcag ggccttgtcc ctggaggtgg ccgaggagat cgcccgcctc     1860
gaggccgagg tcttccgcct ggccggccac cccttcaacc tcaactcccg ggaccagctg     1920
gaaagggtcc tctttgacga gctagggctt cccgccatcg gcaagacgga aagaccggc      1980 aagcgctcca ccagcgccgc cgtcctggag ggcctccgcg aggcccaccc catcgtggag     2040
aagatcctgc agtaccggga gctcaccaag ctgaagagca cctacattga cccccttgccg     2100 gacctcatcc accccaggac gggccgcctc acacccgct tcaaccagac ggccacggcc      2160
acgggcaggc taagtagctc cgatcccaac ctccagaaca tccccgtccg caccccgctt     2220
gggcagagga tccgccgggc cttcatcgcc gaggaggggt ggctattggt ggccctggac     2280
tatagccaga tagagctcag ggtgctggcc cacctctccg gcgacgagaa cctgatccgg     2340
gtcttccagg aggggcggga catccacacg gagaccgcca gctggatgtt cggcgtcccc     2400
cgggaggccg tggacccccg tgatgcgccgg gcggccaaga ccatcaactt cggggtcctc     2460
tacggcatgt cggcccaccg cctctcccag gagctagcca tcccttacga ggaggcccag     2520
gccttcattg agcgctactt tcagagcttc cccaaggtgc gggcctggat tgagaagacc     2580
ctggaggagg caggaggcg ggggtacgtg gagaccctct tcggccgccg ccgctacgtg     2640
ccagacctag aggcccgggt gaagagcgtg cgggaggcgg ccgagcgcat ggccttcaac     2700
atgcccgtcc agggcaccgc cgccgacctc atgaagctgg ctatggtgaa gctcttcccc     2760
aggctggagg aaatgggggc caggatgctc cttcaggtcc acgacgagct ggtcctcgag     2820
gccccaaaag agagggcgga ggccgtggcc cggctggcca aggaggtcat ggagggggtg     2880
tatcccctgg ccgtgcccct ggaggtggag gtggggatag gggaggactg gctctccgcc     2940
```

```
                                                          -continued
aaggagtga                                                                    2949

<210> SEQ ID NO 7
<211> LENGTH: 910
<212> TYPE: PRT
<213> ORGANISM: Artificial Sequence
<220> FEATURE:
<223> OTHER INFORMATION: Description of Artificial Sequence: poly amino
      acids

<400> SEQUENCE: 7

Met Arg Gly Ser His His His His His His Ala Ala Asp Asp Asp
  1               5                  10                  15

Lys Met Arg Gly Met Leu Pro Leu Phe Glu Pro Lys Gly Arg Val Leu
             20                  25                  30

Leu Val Asp Gly His His Leu Ala Tyr Arg Thr Phe His Ala Leu Lys
         35                  40                  45

Gly Leu Thr Thr Ser Arg Gly Glu Pro Val Gln Ala Val Tyr Gly Phe
     50                  55                  60

Ala Lys Ser Leu Leu Lys Ala Leu Lys Glu Asp Gly Asp Ala Val Ile
 65                  70                  75                  80

Val Val Phe Asp Ala Lys Ala Pro Ser Phe Arg His Glu Ala Tyr Gly
                 85                  90                  95

Gly Tyr Lys Ala Gly Arg Ala Pro Thr Pro Glu Asp Phe Pro Arg Gln
            100                 105                 110

Leu Ala Leu Ile Lys Glu Leu Val Asp Leu Leu Gly Leu Ala Arg Leu
        115                 120                 125

Glu Val Pro Gly Tyr Glu Ala Asp Asp Val Leu Ala Ser Leu Ala Lys
    130                 135                 140

Lys Ala Glu Lys Glu Gly Tyr Glu Val Arg Ile Leu Thr Ala Asp Lys
145                 150                 155                 160

Asp Leu Tyr Gln Leu Leu Ser Asp Arg Ile His Val Leu His Pro Glu
                165                 170                 175

Gly Tyr Leu Ile Thr Pro Ala Trp Leu Trp Glu Lys Tyr Gly Leu Arg
            180                 185                 190

Pro Asp Gln Trp Ala Asp Tyr Arg Ala Leu Thr Gly Asp Glu Ser Asp
        195                 200                 205

Asn Leu Pro Gly Val Lys Gly Ile Gly Glu Lys Thr Ala Arg Lys Leu
    210                 215                 220

Leu Glu Glu Trp Gly Ser Leu Glu Ala Leu Leu Lys Asn Leu Asp Arg
225                 230                 235                 240

Leu Lys Pro Ala Ile Arg Glu Lys Ile Leu Ala His Met Asp Asp Leu
                245                 250                 255

Lys Leu Ser Trp Asp Leu Ala Lys Val Arg Thr Asp Leu Pro Leu Glu
            260                 265                 270

Val Asp Phe Ala Lys Arg Arg Glu Pro Asp Arg Glu Arg Leu Arg Ala
        275                 280                 285

Phe Leu Glu Arg Leu Glu Phe Gly Ser Leu Leu His Glu Phe Gly Leu
    290                 295                 300

Leu Glu Ser Pro Tyr Asp Asn Tyr Val Thr Ile Leu Asp Glu Glu Thr
305                 310                 315                 320

Leu Lys Ala Trp Ile Ala Lys Leu Glu Lys Ala Pro Val Phe Ala Phe
                325                 330                 335

Asp Thr Glu Thr Asp Ser Leu Asp Asn Ile Ser Ala Asn Leu Val Gly
            340                 345                 350
```

```
Leu Ser Phe Ala Ile Glu Pro Gly Val Ala Tyr Ile Pro Val Ala
        355                 360                 365

His Asp Tyr Leu Asp Ala Pro Asp Gln Ile Ser Arg Glu Arg Ala Leu
        370                 375                 380

Glu Leu Leu Lys Pro Leu Leu Glu Asp Glu Lys Ala Leu Lys Val Gly
385                 390                 395                 400

Gln Asn Leu Lys Tyr Asp Arg Gly Ile Leu Ala Asn Tyr Gly Ile Glu
                405                 410                 415

Leu Arg Gly Ile Ala Phe Asp Thr Met Leu Glu Ser Tyr Ile Leu Asn
                420                 425                 430

Ser Val Ala Gly Arg His Asp Met Asp Ser Leu Ala Glu Arg Trp Leu
        435                 440                 445

Lys His Lys Thr Ile Thr Phe Glu Glu Ile Ala Gly Lys Gly Lys Asn
        450                 455                 460

Gln Leu Thr Phe Asn Gln Ile Ala Leu Glu Glu Ala Gly Arg Tyr Ala
465                 470                 475                 480

Ala Glu Asp Ala Asp Val Thr Leu Gln Leu His Leu Lys Met Trp Pro
                485                 490                 495

Asp Leu Gln Lys His Glu Arg Leu Leu Trp Leu Tyr Arg Glu Val Glu
                500                 505                 510

Arg Pro Leu Ser Ala Val Leu Ala His Met Glu Ala Thr Gly Val Arg
        515                 520                 525

Leu Asp Val Ala Tyr Leu Arg Ala Leu Ser Leu Glu Val Ala Glu Glu
        530                 535                 540

Val Ala Arg Leu Glu Ala Glu Val Phe Arg Leu Ala Gly His Pro Phe
545                 550                 555                 560

Asn Leu Asn Ser Arg Asp Gln Leu Glu Arg Val Leu Phe Asp Glu Leu
                565                 570                 575

Gly Leu Pro Ala Ile Gly Lys Thr Glu Lys Thr Gly Lys Arg Ser Thr
                580                 585                 590

Ser Ala Ala Val Leu Glu Ala Leu Arg Glu Ala His Pro Ile Val Glu
        595                 600                 605

Lys Ile Leu Gln Tyr Arg Glu Leu Thr Lys Leu Lys Ser Thr Tyr Ile
        610                 615                 620

Asp Pro Leu Pro Asp Leu Ile His Pro Arg Thr Gly Arg Leu His Thr
625                 630                 635                 640

Arg Phe Asn Gln Thr Ala Thr Ala Thr Gly Arg Leu Ser Ser Ser Asp
                645                 650                 655

Pro Asn Leu Gln Asn Ile Pro Val Arg Thr Pro Leu Gly Gln Arg Ile
                660                 665                 670

Arg Arg Ala Phe Ile Ala Glu Glu Gly Trp Leu Leu Val Ala Leu Asp
        675                 680                 685

Tyr Ser Gln Ile Glu Leu Arg Val Leu Ala His Leu Ser Gly Asp Glu
        690                 695                 700

Asn Leu Ile Arg Val Phe Gln Glu Gly Arg Asp Ile His Thr Glu Thr
705                 710                 715                 720

Ala Ser Trp Met Phe Gly Val Pro Arg Glu Ala Val Asp Pro Leu Met
                725                 730                 735

Arg Arg Ala Ala Lys Thr Ile Asn Phe Gly Val Leu Tyr Gly Met Ser
                740                 745                 750

Ala His Arg Leu Ser Gln Glu Leu Ala Ile Pro Tyr Glu Glu Ala Gln
        755                 760                 765

Ala Phe Ile Glu Arg Tyr Phe Gln Ser Phe Pro Lys Val Arg Ala Trp
```

```
        770                 775                 780
Ile Glu Lys Thr Leu Glu Gly Arg Arg Gly Tyr Val Glu Thr
785                 790                 795                 800

Leu Phe Gly Arg Arg Arg Tyr Val Pro Asp Leu Glu Ala Arg Val Lys
                805                 810                 815

Ser Val Arg Glu Ala Ala Glu Arg Met Ala Phe Asn Met Pro Val Gln
                820                 825                 830

Gly Thr Ala Ala Asp Leu Met Lys Leu Ala Met Val Lys Leu Phe Pro
                835                 840                 845

Arg Leu Glu Glu Met Gly Ala Arg Met Leu Leu Gln Val His Asp Glu
850                 855                 860

Leu Val Leu Glu Ala Pro Lys Glu Arg Ala Glu Ala Val Ala Arg Leu
865                 870                 875                 880

Ala Lys Glu Val Met Glu Gly Val Tyr Pro Leu Ala Val Pro Leu Glu
                885                 890                 895

Val Glu Val Gly Ile Gly Glu Asp Trp Leu Ser Ala Lys Glu
                900                 905                 910

<210> SEQ ID NO 8
<211> LENGTH: 910
<212> TYPE: PRT
<213> ORGANISM: Artificial Sequence
<220> FEATURE:
<223> OTHER INFORMATION: Description of Artificial Sequence: poly amino
      acids

<400> SEQUENCE: 8

Met Arg Gly Ser His His His His His His Ala Ala Asp Asp Asp
1               5                   10                  15

Lys Met Arg Gly Met Leu Pro Leu Phe Glu Pro Lys Gly Arg Val Leu
                20                  25                  30

Leu Val Asp Gly His His Leu Ala Tyr Arg Thr Phe His Ala Leu Lys
            35                  40                  45

Gly Leu Thr Thr Ser Arg Gly Glu Pro Val Gln Ala Val Tyr Gly Phe
        50                  55                  60

Ala Lys Ser Leu Leu Lys Ala Leu Lys Glu Asp Gly Asp Ala Val Ile
65                  70                  75                  80

Val Val Phe Asp Ala Lys Ala Pro Ser Phe Arg His Glu Ala Tyr Gly
                85                  90                  95

Gly Tyr Lys Ala Gly Arg Ala Pro Thr Pro Glu Asp Phe Pro Arg Gln
                100                 105                 110

Leu Ala Leu Ile Lys Glu Leu Val Asp Leu Leu Gly Leu Ala Arg Leu
            115                 120                 125

Glu Val Pro Gly Tyr Glu Ala Asp Asp Val Leu Ala Ser Leu Ala Lys
        130                 135                 140

Lys Ala Glu Lys Glu Gly Tyr Glu Val Arg Ile Leu Thr Ala Asp Lys
145                 150                 155                 160

Asp Leu Tyr Gln Leu Leu Ser Asp Arg Ile His Val Leu His Pro Glu
                165                 170                 175

Gly Tyr Leu Ile Thr Pro Ala Trp Leu Trp Glu Lys Tyr Gly Leu Arg
                180                 185                 190

Pro Asp Gln Trp Ala Asp Tyr Arg Ala Leu Thr Gly Asp Glu Ser Asp
            195                 200                 205

Asn Leu Pro Gly Val Lys Gly Ile Gly Glu Lys Thr Ala Arg Lys Leu
        210                 215                 220
```

```
Leu Glu Glu Trp Gly Ser Leu Glu Ala Leu Leu Lys Asn Leu Asp Arg
225                 230                 235                 240

Leu Lys Pro Ala Ile Arg Glu Lys Ile Leu Ala His Met Asp Asp Leu
            245                 250                 255

Lys Leu Ser Trp Asp Leu Ala Lys Val Arg Thr Asp Leu Pro Leu Glu
                260                 265                 270

Val Asp Phe Ala Lys Arg Arg Glu Pro Asp Arg Glu Arg Leu Arg Ala
            275                 280                 285

Phe Leu Glu Arg Leu Glu Phe Gly Ser Leu Leu His Glu Phe Gly Leu
            290                 295                 300

Leu Glu Ser Pro Tyr Asp Asn Tyr Val Thr Ile Leu Asp Glu Glu Thr
305                 310                 315                 320

Leu Lys Ala Trp Ile Ala Lys Leu Glu Lys Ala Pro Val Phe Ala Phe
                325                 330                 335

Asp Thr Glu Thr Asp Ser Leu Asp Asn Ile Ser Ala Asn Leu Val Gly
            340                 345                 350

Leu Ser Phe Ala Ile Glu Pro Gly Val Ala Ala Tyr Ile Pro Val Ala
            355                 360                 365

His Asp Tyr Leu Asp Ala Pro Asp Gln Ile Ser Arg Glu Arg Ala Leu
            370                 375                 380

Glu Leu Leu Lys Pro Leu Leu Glu Asp Glu Lys Ala Leu Lys Val Gly
385                 390                 395                 400

Gln Asn Leu Lys Tyr Asp Arg Gly Ile Leu Ala Asn Tyr Gly Ile Glu
            405                 410                 415

Leu Arg Gly Ile Ala Phe Asp Thr Met Leu Glu Ser Tyr Ile Leu Asn
                420                 425                 430

Ser Val Ala Gly Arg His Asp Met Asp Ser Leu Ala Glu Arg Trp Leu
            435                 440                 445

Lys His Lys Thr Ile Thr Phe Glu Glu Ile Ala Gly Lys Gly Lys Asn
450                 455                 460

Gln Leu Thr Phe Asn Gln Ile Ala Leu Glu Glu Ala Gly Arg Tyr Ala
465                 470                 475                 480

Ala Glu Asp Ala Asp Val Thr Leu Gln Leu His Leu Lys Met Trp Pro
                485                 490                 495

Asp Leu Gln Lys His Lys Gly Pro Leu Asn Val Phe Glu Asn Ile Glu
            500                 505                 510

Met Pro Leu Val Pro Val Leu Ser Arg Ile Glu Arg Asn Gly Val Arg
            515                 520                 525

Leu Asp Val Ala Tyr Leu Arg Ala Leu Ser Leu Glu Val Ala Glu Glu
530                 535                 540

Ile Ala Arg Leu Glu Ala Glu Val Phe Arg Leu Ala Gly His Pro Phe
545                 550                 555                 560

Asn Leu Asn Ser Arg Asp Gln Leu Glu Arg Val Leu Phe Asp Glu Leu
            565                 570                 575

Gly Leu Pro Ala Ile Gly Lys Thr Glu Lys Thr Gly Lys Arg Ser Thr
            580                 585                 590

Ser Ala Ala Val Leu Glu Ala Leu Arg Glu Ala His Pro Ile Val Glu
            595                 600                 605

Lys Ile Leu Gln Tyr Arg Glu Leu Thr Lys Leu Lys Ser Thr Tyr Ile
610                 615                 620

Asp Pro Leu Pro Asp Leu Ile His Pro Arg Thr Gly Arg Leu His Thr
625                 630                 635                 640

Arg Phe Asn Gln Thr Ala Thr Ala Thr Gly Arg Leu Ser Ser Ser Asp
```

-continued

```
                    645                 650                 655
Pro Asn Leu Gln Asn Ile Pro Val Arg Thr Pro Leu Gly Gln Arg Ile
                660                 665                 670

Arg Arg Ala Phe Ile Ala Glu Glu Gly Trp Leu Leu Val Ala Leu Asp
            675                 680                 685

Tyr Ser Gln Ile Glu Leu Arg Val Leu Ala His Leu Ser Gly Asp Glu
        690                 695                 700

Asn Leu Ile Arg Val Phe Gln Glu Gly Arg Asp Ile His Thr Glu Thr
705                 710                 715                 720

Ala Ser Trp Met Phe Gly Val Pro Arg Glu Ala Val Asp Pro Leu Met
                725                 730                 735

Arg Arg Ala Ala Lys Thr Ile Asn Phe Gly Val Leu Tyr Gly Met Ser
            740                 745                 750

Ala His Arg Leu Ser Gln Glu Leu Ala Ile Pro Tyr Glu Glu Ala Gln
        755                 760                 765

Ala Phe Ile Glu Arg Tyr Phe Gln Ser Phe Pro Lys Val Arg Ala Trp
    770                 775                 780

Ile Glu Lys Thr Leu Glu Glu Gly Arg Arg Gly Tyr Val Glu Thr
785                 790                 795                 800

Leu Phe Gly Arg Arg Tyr Val Pro Asp Leu Glu Ala Arg Val Lys
                805                 810                 815

Ser Val Arg Glu Ala Ala Glu Arg Met Ala Phe Asn Met Pro Val Gln
            820                 825                 830

Gly Thr Ala Ala Asp Leu Met Lys Leu Ala Met Val Lys Leu Phe Pro
        835                 840                 845

Arg Leu Glu Glu Met Gly Ala Arg Met Leu Leu Gln Val His Asp Glu
    850                 855                 860

Leu Val Leu Glu Ala Pro Lys Glu Arg Ala Glu Ala Val Ala Arg Leu
865                 870                 875                 880

Ala Lys Glu Val Met Glu Gly Val Tyr Pro Leu Ala Val Pro Leu Glu
                885                 890                 895

Val Glu Val Gly Ile Gly Glu Asp Trp Leu Ser Ala Lys Glu
            900                 905                 910

<210> SEQ ID NO 9
<211> LENGTH: 908
<212> TYPE: PRT
<213> ORGANISM: Artificial Sequence
<220> FEATURE:
<223> OTHER INFORMATION: Description of Artificial Sequence: poly amino
      acids

<400> SEQUENCE: 9

Met Arg Gly Ser His His His His His His Ala Ala Asp Asp Asp
  1               5                   10                  15

Lys Met Arg Gly Met Leu Pro Leu Phe Glu Pro Lys Gly Arg Val Leu
                20                  25                  30

Leu Val Asp Gly His His Leu Ala Tyr Arg Thr Phe His Ala Leu Lys
            35                  40                  45

Gly Leu Thr Thr Ser Arg Gly Glu Pro Val Gln Ala Val Tyr Gly Phe
        50                  55                  60

Ala Lys Ser Leu Leu Lys Ala Leu Lys Glu Asp Gly Asp Ala Val Ile
65                  70                  75                  80

Val Val Phe Asp Ala Lys Ala Pro Ser Phe Arg His Glu Ala Tyr Gly
                85                  90                  95
```

```
Gly Tyr Lys Ala Gly Arg Ala Pro Thr Pro Glu Asp Phe Pro Arg Gln
            100                 105                 110

Leu Ala Leu Ile Lys Glu Leu Val Asp Leu Leu Gly Leu Ala Arg Leu
        115                 120                 125

Glu Val Pro Gly Tyr Glu Ala Asp Val Leu Ala Ser Leu Ala Lys
    130                 135                 140

Lys Ala Glu Lys Glu Gly Tyr Glu Val Arg Ile Leu Thr Ala Asp Lys
145                 150                 155                 160

Asp Leu Tyr Gln Leu Leu Ser Asp Arg Ile His Val Leu His Pro Glu
                165                 170                 175

Gly Tyr Leu Ile Thr Pro Ala Trp Leu Trp Glu Lys Tyr Gly Leu Arg
            180                 185                 190

Pro Asp Gln Trp Ala Asp Tyr Arg Ala Leu Thr Gly Asp Glu Ser Asp
        195                 200                 205

Asn Leu Pro Gly Val Lys Gly Ile Gly Glu Lys Thr Ala Arg Lys Leu
    210                 215                 220

Leu Glu Glu Trp Gly Ser Leu Glu Ala Leu Leu Lys Asn Leu Asp Arg
225                 230                 235                 240

Leu Lys Pro Ala Ile Arg Glu Lys Ile Leu Ala His Met Asp Asp Leu
                245                 250                 255

Lys Leu Ser Trp Asp Leu Ala Lys Val Arg Thr Asp Leu Pro Leu Glu
            260                 265                 270

Val Asp Phe Ala Lys Arg Arg Glu Pro Asp Arg Glu Arg Leu Arg Ala
        275                 280                 285

Phe Leu Glu Arg Leu Glu Phe Gly Ser Leu Leu His Glu Phe Gly Leu
    290                 295                 300

Leu Glu Ser Pro Pro Val Gly Tyr Arg Ile Val Lys Asp Leu Val Glu
305                 310                 315                 320

Phe Glu Lys Leu Ile Glu Lys Leu Arg Glu Ser Pro Ser Phe Ala Ile
                325                 330                 335

Asp Leu Glu Thr Ser Ser Leu Asp Pro Phe Asp Cys Asp Ile Val Gly
            340                 345                 350

Ile Ser Val Ser Phe Lys Pro Lys Glu Ala Tyr Tyr Ile Pro Leu His
        355                 360                 365

His Arg Asn Ala Gln Asn Leu Asp Glu Lys Glu Val Leu Lys Lys Leu
    370                 375                 380

Lys Glu Ile Leu Glu Asp Pro Gly Ala Lys Ile Val Gly Gln Asn Leu
385                 390                 395                 400

Lys Phe Asp Tyr Lys Val Leu Met Val Lys Gly Val Glu Pro Val Pro
                405                 410                 415

Pro His Phe Asp Thr Met Ile Ala Ala Tyr Leu Leu Glu Pro Asn Glu
            420                 425                 430

Lys Lys Phe Asn Leu Asp Asp Leu Ala Leu Lys Phe Leu Gly Tyr Lys
        435                 440                 445

Met Thr Ser Tyr Gln Glu Leu Met Ser Phe Ser Pro Leu Phe Gly
    450                 455                 460

Phe Ser Phe Ala Asp Val Pro Val Glu Lys Ala Ala Asn Tyr Ser Cys
465                 470                 475                 480

Glu Asp Ala Asp Ile Thr Tyr Arg Leu Tyr Lys Ile Leu Ser Leu Lys
                485                 490                 495

Leu His Glu Glu Arg Leu Leu Trp Leu Tyr Arg Glu Val Glu Arg Pro
            500                 505                 510

Leu Ser Ala Val Leu Ala His Met Glu Ala Thr Gly Val Arg Leu Asp
```

-continued

```
            515                 520                 525
Val Ala Tyr Leu Arg Ala Leu Ser Leu Glu Val Ala Glu Ile Ala
    530                 535                 540

Arg Leu Glu Ala Glu Val Phe Arg Leu Ala Gly His Pro Phe Asn Leu
545                 550                 555                 560

Asn Ser Arg Asp Gln Leu Glu Arg Val Leu Phe Asp Glu Leu Gly Leu
                565                 570                 575

Pro Ala Ile Gly Lys Thr Glu Lys Thr Gly Lys Arg Ser Thr Ser Ala
            580                 585                 590

Ala Val Leu Glu Ala Leu Arg Glu Ala His Pro Ile Val Glu Lys Ile
            595                 600                 605

Leu Gln Tyr Arg Glu Leu Thr Lys Leu Lys Ser Thr Tyr Ile Asp Pro
            610                 615                 620

Leu Pro Asp Leu Ile His Pro Arg Thr Gly Arg Leu His Thr Arg Phe
625                 630                 635                 640

Asn Gln Thr Ala Thr Ala Thr Gly Arg Leu Ser Ser Ser Asp Pro Asn
                645                 650                 655

Leu Gln Asn Ile Pro Val Arg Thr Pro Leu Gly Gln Arg Ile Arg Arg
            660                 665                 670

Ala Phe Ile Ala Glu Glu Gly Trp Leu Leu Val Ala Leu Asp Tyr Ser
            675                 680                 685

Gln Ile Glu Leu Arg Val Leu Ala His Leu Ser Gly Asp Glu Asn Leu
            690                 695                 700

Ile Arg Val Phe Gln Glu Gly Arg Asp Ile His Thr Glu Thr Ala Ser
705                 710                 715                 720

Trp Met Phe Gly Val Pro Arg Glu Ala Val Asp Pro Leu Met Arg Arg
                725                 730                 735

Ala Ala Lys Thr Ile Asn Phe Gly Val Leu Tyr Gly Met Ser Ala His
            740                 745                 750

Arg Leu Ser Gln Glu Leu Ala Ile Pro Tyr Glu Glu Ala Gln Ala Phe
            755                 760                 765

Ile Glu Arg Tyr Phe Gln Ser Phe Pro Lys Val Arg Ala Trp Ile Glu
            770                 775                 780

Lys Thr Leu Glu Glu Gly Arg Arg Gly Tyr Val Glu Thr Leu Phe
785                 790                 795                 800

Gly Arg Arg Arg Tyr Val Pro Asp Leu Glu Ala Arg Val Lys Ser Val
                805                 810                 815

Arg Glu Ala Ala Glu Arg Met Ala Phe Asn Met Pro Val Gln Gly Thr
            820                 825                 830

Ala Ala Asp Leu Met Lys Leu Ala Met Val Lys Leu Phe Pro Arg Leu
            835                 840                 845

Glu Glu Met Gly Ala Arg Met Leu Leu Gln Val His Asp Glu Leu Val
850                 855                 860

Leu Glu Ala Pro Lys Glu Arg Ala Glu Ala Val Ala Arg Leu Ala Lys
865                 870                 875                 880

Glu Val Met Glu Gly Val Tyr Pro Leu Ala Val Pro Leu Glu Val Glu
                885                 890                 895

Val Gly Ile Gly Glu Asp Trp Leu Ser Ala Lys Glu
            900                 905
```

<210> SEQ ID NO 10
<211> LENGTH: 908
<212> TYPE: PRT
<213> ORGANISM: Artificial Sequence -continued

```
<220> FEATURE:
<223> OTHER INFORMATION: Description of Artificial Sequence: poly amino
      acids

<400> SEQUENCE: 10

Met Arg Gly Ser His His His His His His Ala Ala Asp Asp Asp Asp
1               5                   10                  15

Lys Met Arg Gly Met Leu Pro Leu Phe Glu Pro Lys Gly Arg Val Leu
            20                  25                  30

Leu Val Asp Gly His His Leu Ala Tyr Arg Thr Phe His Ala Leu Lys
        35                  40                  45

Gly Leu Thr Thr Ser Arg Gly Glu Pro Val Gln Ala Val Tyr Gly Phe
    50                  55                  60

Ala Lys Ser Leu Leu Lys Ala Leu Lys Glu Asp Gly Asp Ala Val Ile
65                  70                  75                  80

Val Val Phe Asp Ala Lys Ala Pro Ser Phe Arg His Glu Ala Tyr Gly
                85                  90                  95

Gly Tyr Lys Ala Gly Arg Ala Pro Thr Pro Glu Asp Phe Pro Arg Gln
            100                 105                 110

Leu Ala Leu Ile Lys Glu Leu Val Asp Leu Leu Gly Leu Ala Arg Leu
        115                 120                 125

Glu Val Pro Gly Tyr Glu Ala Asp Asp Val Leu Ala Ser Leu Ala Lys
    130                 135                 140

Lys Ala Glu Lys Glu Gly Tyr Glu Val Arg Ile Leu Thr Ala Asp Lys
145                 150                 155                 160

Asp Leu Tyr Gln Leu Leu Ser Asp Arg Ile His Val Leu His Pro Glu
                165                 170                 175

Gly Tyr Leu Ile Thr Pro Ala Trp Leu Trp Glu Lys Tyr Gly Leu Arg
            180                 185                 190

Pro Asp Gln Trp Ala Asp Tyr Arg Ala Leu Thr Gly Asp Glu Ser Asp
        195                 200                 205

Asn Leu Pro Gly Val Lys Gly Ile Gly Glu Lys Thr Ala Arg Lys Leu
    210                 215                 220

Leu Glu Glu Trp Gly Ser Leu Glu Ala Leu Leu Lys Asn Leu Asp Arg
225                 230                 235                 240

Leu Lys Pro Ala Ile Arg Glu Lys Ile Leu Ala His Met Asp Asp Leu
                245                 250                 255

Lys Leu Ser Trp Asp Leu Ala Lys Val Arg Thr Asp Leu Pro Leu Glu
            260                 265                 270

Val Asp Phe Ala Lys Arg Arg Glu Pro Asp Arg Glu Arg Leu Arg Ala
        275                 280                 285

Phe Leu Glu Arg Leu Glu Phe Gly Ser Leu Leu His Glu Phe Gly Leu
    290                 295                 300

Leu Glu Ser Pro Pro Val Gly Tyr Arg Ile Val Lys Asp Leu Val Glu
305                 310                 315                 320

Phe Glu Lys Leu Ile Glu Lys Leu Arg Glu Ser Pro Ser Phe Ala Ile
                325                 330                 335

Asp Leu Glu Thr Ser Ser Leu Asp Pro Phe Asp Cys Asp Ile Val Gly
            340                 345                 350

Ile Ser Val Ser Phe Lys Pro Lys Glu Ala Tyr Tyr Ile Pro Leu His
        355                 360                 365

His Arg Asn Ala Gln Asn Leu Asp Glu Lys Glu Val Leu Lys Lys Leu
    370                 375                 380

Lys Glu Ile Leu Glu Asp Pro Gly Ala Lys Ile Val Gly Gln Asn Leu
```

```
                385                 390                 395                 400
Lys Phe Asp Tyr Lys Val Leu Met Val Lys Gly Val Glu Pro Val Pro
                405                 410                 415

Pro His Phe Asp Thr Met Ile Ala Ala Tyr Leu Leu Glu Pro Asn Glu
            420                 425                 430

Lys Lys Phe Asn Leu Asp Asp Leu Ala Leu Lys Phe Leu Gly Tyr Lys
            435                 440                 445

Met Thr Ser Tyr Gln Glu Leu Met Ser Phe Ser Pro Leu Phe Gly
    450                 455                 460

Phe Ser Phe Ala Asp Val Pro Val Glu Lys Ala Ala Asn Tyr Ser Cys
465                 470                 475                 480

Glu Asp Ala Asp Ile Thr Tyr Arg Leu Tyr Lys Ile Leu Ser Leu Lys
                485                 490                 495

Leu His Glu Ala Asp Leu Glu Asn Val Phe Tyr Lys Ile Glu Met Pro
                500                 505                 510

Leu Val Ser Val Leu Ala Arg Met Glu Leu Asn Gly Val Arg Leu Asp
            515                 520                 525

Val Ala Tyr Leu Arg Ala Leu Ser Leu Glu Val Ala Glu Glu Ile Ala
    530                 535                 540

Arg Leu Glu Ala Glu Val Phe Arg Leu Ala Gly His Pro Phe Asn Leu
545                 550                 555                 560

Asn Ser Arg Asp Gln Leu Glu Arg Val Leu Phe Asp Glu Leu Gly Leu
                565                 570                 575

Pro Ala Ile Gly Lys Thr Glu Lys Thr Gly Lys Arg Ser Thr Ser Ala
            580                 585                 590

Ala Val Leu Glu Ala Leu Arg Glu Ala His Pro Ile Val Glu Lys Ile
            595                 600                 605

Leu Gln Tyr Arg Glu Leu Thr Lys Leu Lys Ser Thr Tyr Ile Asp Pro
    610                 615                 620

Leu Pro Asp Leu Ile His Pro Arg Thr Gly Arg Leu His Thr Arg Phe
625                 630                 635                 640

Asn Gln Thr Ala Thr Ala Thr Gly Arg Leu Ser Ser Ser Asp Pro Asn
                645                 650                 655

Leu Gln Asn Ile Pro Val Arg Thr Pro Leu Gly Gln Arg Ile Arg Arg
            660                 665                 670

Ala Phe Ile Ala Glu Glu Gly Trp Leu Leu Val Ala Leu Asp Tyr Ser
            675                 680                 685

Gln Ile Glu Leu Arg Val Leu Ala His Leu Ser Gly Asp Glu Asn Leu
    690                 695                 700

Ile Arg Val Phe Gln Glu Gly Arg Asp Ile His Thr Glu Thr Ala Ser
705                 710                 715                 720

Trp Met Phe Gly Val Pro Arg Glu Ala Val Asp Pro Leu Met Arg Arg
                725                 730                 735

Ala Ala Lys Thr Ile Asn Phe Gly Val Leu Tyr Gly Met Ser Ala His
            740                 745                 750

Arg Leu Ser Gln Glu Leu Ala Ile Pro Tyr Glu Glu Ala Gln Ala Phe
            755                 760                 765

Ile Glu Arg Tyr Phe Gln Ser Phe Pro Lys Val Arg Ala Trp Ile Glu
    770                 775                 780

Lys Thr Leu Glu Glu Gly Arg Arg Gly Tyr Val Glu Thr Leu Phe
785                 790                 795                 800

Gly Arg Arg Arg Tyr Val Pro Asp Leu Glu Ala Arg Val Lys Ser Val
                805                 810                 815
```

Arg Glu Ala Ala Glu Arg Met Ala Phe Asn Met Pro Val Gln Gly Thr
              820                 825                 830

Ala Ala Asp Leu Met Lys Leu Ala Met Val Lys Leu Phe Pro Arg Leu
              835                 840                 845

Glu Glu Met Gly Ala Arg Met Leu Leu Gln Val His Asp Glu Leu Val
              850                 855                 860

Leu Glu Ala Pro Lys Glu Arg Ala Glu Val Ala Arg Leu Ala Lys
865                 870                 875                 880

Glu Val Met Glu Gly Val Tyr Pro Leu Ala Val Pro Leu Glu Val Glu
                  885                 890                 895

Val Gly Ile Gly Glu Asp Trp Leu Ser Ala Lys Glu
              900                 905

<210> SEQ ID NO 11
<211> LENGTH: 949
<212> TYPE: PRT
<213> ORGANISM: Artificial Sequence
<220> FEATURE:
<223> OTHER INFORMATION: Description of Artificial Sequence: poly amino
      acids

<400> SEQUENCE: 11

Met Arg Gly Ser His His His His His His Ala Ala Asp Asp Asp Asp
1               5                   10                  15

Lys Met Arg Gly Met Leu Pro Leu Phe Glu Pro Lys Gly Arg Val Leu
              20                  25                  30

Leu Val Asp Gly His His Leu Ala Tyr Arg Thr Phe His Ala Leu Lys
          35                  40                  45

Gly Leu Thr Thr Ser Arg Gly Glu Pro Val Gln Ala Val Tyr Gly Phe
      50                  55                  60

Ala Lys Ser Leu Leu Lys Ala Leu Lys Glu Asp Gly Asp Ala Val Ile
65                  70                  75                  80

Val Val Phe Asp Ala Lys Ala Pro Ser Phe Arg His Glu Ala Tyr Gly
                  85                  90                  95

Gly Tyr Lys Ala Gly Arg Ala Pro Thr Pro Glu Asp Phe Pro Arg Gln
              100                 105                 110

Leu Ala Leu Ile Lys Glu Leu Val Asp Leu Leu Gly Leu Ala Arg Leu
          115                 120                 125

Glu Val Pro Gly Tyr Glu Ala Asp Asp Val Leu Ala Ser Leu Ala Lys
      130                 135                 140

Lys Ala Glu Lys Glu Gly Tyr Glu Val Arg Ile Leu Thr Ala Asp Lys
145                 150                 155                 160

Asp Leu Tyr Gln Leu Leu Ser Asp Arg Ile His Val Leu His Pro Glu
                  165                 170                 175

Gly Tyr Leu Ile Thr Pro Ala Trp Leu Trp Glu Lys Tyr Gly Leu Arg
              180                 185                 190

Pro Asp Gln Trp Ala Asp Tyr Arg Ala Leu Thr Gly Asp Glu Ser Asp
          195                 200                 205

Asn Leu Pro Gly Val Lys Gly Ile Gly Glu Lys Thr Ala Arg Lys Leu
      210                 215                 220

Leu Glu Glu Trp Gly Ser Leu Glu Ala Leu Leu Lys Asn Leu Asp Arg
225                 230                 235                 240

Leu Lys Pro Ala Ile Arg Glu Lys Ile Leu Ala His Met Asp Asp Leu
                  245                 250                 255

Lys Leu Ser Trp Asp Leu Ala Lys Val Arg Thr Asp Leu Pro Leu Glu

-continued

```
                    260                 265                 270
Val Asp Phe Ala Lys Arg Arg Glu Pro Asp Arg Glu Arg Leu Arg Ala
                275                 280                 285
Phe Leu Glu Arg Leu Glu Phe Gly Ser Leu Leu His Glu Phe Gly Leu
            290                 295                 300
Leu Glu Ser Pro His Pro Ala Val Val Asp Ile Phe Glu Tyr Asp Ile
305                 310                 315                 320
Pro Phe Ala Lys Arg Tyr Leu Ile Asp Lys Gly Leu Ile Pro Met Glu
                325                 330                 335
Gly Glu Glu Leu Lys Ile Leu Ala Phe Asp Ile Glu Thr Leu Tyr
            340                 345                 350
His Glu Gly Glu Glu Phe Gly Lys Gly Pro Ile Ile Met Ile Ser Tyr
            355                 360                 365
Ala Asp Glu Asn Glu Ala Lys Val Ile Thr Trp Lys Asn Ile Asp Leu
        370                 375                 380
Pro Tyr Val Glu Val Val Ser Ser Glu Arg Glu Met Ile Lys Arg Phe
385                 390                 395                 400
Leu Arg Ile Ile Arg Glu Lys Asp Pro Asp Ile Ile Val Thr Tyr Asn
                405                 410                 415
Gly Asp Ser Phe Asp Phe Pro Tyr Leu Ala Lys Arg Ala Glu Lys Leu
            420                 425                 430
Gly Ile Lys Leu Thr Ile Gly Arg Asp Gly Ser Glu Pro Lys Met Gln
        435                 440                 445
Arg Ile Gly Asp Met Thr Ala Val Glu Val Lys Gly Arg Ile His Phe
        450                 455                 460
Asp Leu Tyr His Val Ile Thr Arg Thr Ile Asn Leu Pro Thr Tyr Thr
465                 470                 475                 480
Leu Glu Ala Val Tyr Glu Ala Ile Phe Gly Lys Pro Lys Glu Lys Val
                485                 490                 495
Tyr Ala Asp Glu Ile Ala Lys Ala Trp Glu Ser Gly Glu Asn Leu Glu
            500                 505                 510
Arg Val Ala Lys Tyr Ser Met Glu Asp Ala Lys Ala Thr Tyr Glu Leu
        515                 520                 525
Gly Lys Glu Phe Leu Pro Met Glu Ile Gln Leu Ser Glu Arg Leu Leu
    530                 535                 540
Trp Leu Tyr Arg Glu Val Glu Arg Pro Leu Ser Ala Val Leu Ala His
545                 550                 555                 560
Met Glu Ala Thr Gly Val Arg Leu Asp Val Ala Tyr Leu Arg Ala Leu
                565                 570                 575
Ser Leu Glu Val Ala Glu Glu Ile Ala Arg Leu Glu Ala Glu Val Phe
            580                 585                 590
Arg Leu Ala Gly His Pro Phe Asn Leu Asn Ser Arg Asp Gln Leu Glu
        595                 600                 605
Arg Val Leu Phe Asp Glu Leu Gly Leu Pro Ala Ile Gly Lys Thr Glu
        610                 615                 620
Lys Thr Gly Lys Arg Ser Thr Ser Ala Ala Val Leu Glu Ala Leu Arg
625                 630                 635                 640
Glu Ala His Pro Ile Val Glu Lys Ile Leu Gln Tyr Arg Glu Leu Thr
                645                 650                 655
Lys Leu Lys Ser Thr Tyr Ile Asp Pro Leu Pro Asp Leu Ile His Pro
            660                 665                 670
Arg Thr Gly Arg Leu His Thr Arg Phe Asn Gln Thr Ala Thr Ala Thr
        675                 680                 685
```

```
Gly Arg Leu Ser Ser Ser Asp Pro Asn Leu Gln Asn Ile Pro Val Arg
    690                 695                 700

Thr Pro Leu Gly Gln Arg Ile Arg Arg Ala Phe Ile Ala Glu Glu Gly
705                 710                 715                 720

Trp Leu Leu Val Ala Leu Asp Tyr Ser Gln Ile Glu Leu Arg Val Leu
                725                 730                 735

Ala His Leu Ser Gly Asp Glu Asn Leu Ile Arg Val Phe Gln Glu Gly
            740                 745                 750

Arg Asp Ile His Thr Glu Thr Ala Ser Trp Met Phe Gly Val Pro Arg
        755                 760                 765

Glu Ala Val Asp Pro Leu Met Arg Arg Ala Lys Thr Ile Asn Phe
770                 775                 780

Gly Val Leu Tyr Gly Met Ser Ala His Arg Leu Ser Gln Glu Leu Ala
785                 790                 795                 800

Ile Pro Tyr Glu Glu Ala Gln Ala Phe Ile Glu Arg Tyr Phe Gln Ser
                805                 810                 815

Phe Pro Lys Val Arg Ala Trp Ile Glu Lys Thr Leu Glu Glu Gly Arg
            820                 825                 830

Arg Arg Gly Tyr Val Glu Thr Leu Phe Gly Arg Arg Arg Tyr Val Pro
        835                 840                 845

Asp Leu Glu Ala Arg Val Lys Ser Val Arg Glu Ala Ala Glu Arg Met
    850                 855                 860

Ala Phe Asn Met Pro Val Gln Gly Thr Ala Ala Asp Leu Met Lys Leu
865                 870                 875                 880

Ala Met Val Lys Leu Phe Pro Arg Leu Glu Glu Met Gly Ala Arg Met
                885                 890                 895

Leu Leu Gln Val His Asp Glu Leu Val Leu Glu Ala Pro Lys Glu Arg
            900                 905                 910

Ala Glu Ala Val Ala Arg Leu Ala Lys Glu Val Met Glu Gly Val Tyr
        915                 920                 925

Pro Leu Ala Val Pro Leu Glu Val Glu Val Gly Ile Gly Glu Asp Trp
    930                 935                 940

Leu Ser Ala Lys Glu
945

<210> SEQ ID NO 12
<211> LENGTH: 982
<212> TYPE: PRT
<213> ORGANISM: Artificial Sequence
<220> FEATURE:
<223> OTHER INFORMATION: Description of Artificial Sequence: poly amino
      acids

<400> SEQUENCE: 12

Met Arg Gly Ser His His His His His His Ala Ala Asp Asp Asp
1               5                   10                  15

Lys Met Arg Gly Met Leu Pro Leu Phe Glu Pro Lys Gly Arg Val Leu
                20                  25                  30

Leu Val Asp Gly His His Leu Ala Tyr Arg Thr Phe His Ala Leu Lys
            35                  40                  45

Gly Leu Thr Thr Ser Arg Gly Glu Pro Val Gln Ala Val Tyr Gly Phe
        50                  55                  60

Ala Lys Ser Leu Leu Lys Ala Leu Lys Glu Asp Gly Asp Ala Val Ile
65                  70                  75                  80

Val Val Phe Asp Ala Lys Ala Pro Ser Phe Arg His Glu Ala Tyr Gly
```

-continued

```
                 85                  90                  95
Gly Tyr Lys Ala Gly Arg Ala Pro Thr Pro Glu Asp Phe Pro Arg Gln
            100                 105                 110
Leu Ala Leu Ile Lys Glu Leu Val Asp Leu Leu Gly Leu Ala Arg Leu
            115                 120                 125
Glu Val Pro Gly Tyr Glu Ala Asp Val Leu Ala Ser Leu Ala Lys
        130                 135                 140
Lys Ala Glu Lys Glu Gly Tyr Glu Val Arg Ile Leu Thr Ala Asp Lys
145                 150                 155                 160
Asp Leu Tyr Gln Leu Leu Ser Asp Arg Ile His Val Leu His Pro Glu
                165                 170                 175
Gly Tyr Leu Ile Thr Pro Ala Trp Leu Trp Glu Lys Tyr Gly Leu Arg
                180                 185                 190
Pro Asp Gln Trp Ala Asp Tyr Arg Ala Leu Thr Gly Asp Glu Ser Asp
                195                 200                 205
Asn Leu Pro Gly Val Lys Gly Ile Gly Glu Lys Thr Ala Arg Lys Leu
        210                 215                 220
Leu Glu Glu Trp Gly Ser Leu Glu Ala Leu Leu Lys Asn Leu Asp Arg
225                 230                 235                 240
Leu Lys Pro Ala Ile Arg Glu Lys Ile Leu Ala His Met Asp Asp Leu
                245                 250                 255
Lys Leu Ser Trp Asp Leu Ala Lys Val Arg Thr Asp Leu Pro Leu Glu
                260                 265                 270
Val Asp Phe Ala Lys Arg Arg Glu Pro Asp Arg Glu Arg Leu Arg Ala
        275                 280                 285
Phe Leu Glu Arg Leu Glu Phe Gly Ser Leu Leu His Glu Phe Gly Leu
        290                 295                 300
Leu Glu Ser Pro Val Arg Glu His Pro Ala Val Asp Ile Phe Glu
305                 310                 315                 320
Tyr Asp Ile Pro Phe Ala Lys Arg Tyr Leu Ile Asp Lys Gly Leu Ile
                325                 330                 335
Pro Met Glu Gly Glu Glu Glu Leu Lys Ile Leu Ala Phe Asp Ile Glu
            340                 345                 350
Thr Leu Tyr His Glu Gly Glu Glu Phe Gly Lys Gly Pro Ile Ile Met
                355                 360                 365
Ile Ser Tyr Ala Asp Glu Asn Glu Ala Lys Val Ile Thr Trp Lys Asn
        370                 375                 380
Ile Asp Leu Pro Tyr Val Glu Val Val Ser Ser Glu Arg Glu Met Ile
385                 390                 395                 400
Lys Arg Phe Leu Arg Ile Ile Arg Glu Lys Asp Pro Asp Ile Ile Val
                405                 410                 415
Thr Tyr Asn Gly Asp Ser Phe Asp Phe Pro Tyr Leu Ala Lys Arg Ala
                420                 425                 430
Glu Lys Leu Gly Ile Lys Leu Thr Ile Gly Arg Asp Gly Ser Glu Pro
            435                 440                 445
Lys Met Gln Arg Ile Gly Asp Met Thr Ala Val Glu Val Lys Gly Arg
        450                 455                 460
Ile His Phe Asp Leu Tyr His Val Ile Thr Arg Thr Ile Asn Leu Pro
465                 470                 475                 480
Thr Tyr Thr Leu Glu Ala Val Tyr Glu Ala Ile Phe Gly Lys Pro Lys
                485                 490                 495
Glu Lys Val Tyr Ala Asp Glu Ile Ala Lys Ala Trp Glu Ser Gly Glu
            500                 505                 510
```

```
Asn Leu Glu Arg Val Ala Lys Tyr Ser Met Glu Asp Ala Lys Ala Thr
        515                 520                 525

Tyr Glu Leu Gly Lys Glu Phe Leu Pro Met Glu Ile Gln Leu Ser Arg
530                 535                 540

Leu Val Gly Gln Pro Leu Trp Asp Val Ser Arg Ser Ser Thr Gly Asn
545                 550                 555                 560

Leu Val Glu Trp Phe Leu Leu Arg Lys Ala Tyr Glu Arg Asn Glu Val
                565                 570                 575

Ala Pro Asn Lys Pro Ser Glu Glu Tyr Gln Arg Arg Leu Arg Glu
            580                 585                 590

Ser Tyr Thr Gly Gly Phe Val Arg Leu Asp Val Ala Tyr Leu Arg Ala
        595                 600                 605

Leu Ser Leu Glu Val Ala Glu Ile Ala Arg Leu Glu Ala Glu Val
        610                 615                 620

Phe Arg Leu Ala Gly His Pro Phe Asn Leu Asn Ser Arg Asp Gln Leu
625                 630                 635                 640

Glu Arg Val Leu Phe Asp Glu Leu Gly Leu Pro Ala Ile Gly Lys Thr
                645                 650                 655

Glu Lys Thr Gly Lys Arg Ser Thr Ser Ala Ala Val Leu Glu Ala Leu
                660                 665                 670

Arg Glu Ala His Pro Ile Val Glu Lys Ile Leu Gln Tyr Arg Glu Leu
            675                 680                 685

Thr Lys Leu Lys Ser Thr Tyr Ile Asp Pro Leu Pro Asp Leu Ile His
690                 695                 700

Pro Arg Thr Gly Arg Leu His Thr Arg Phe Asn Gln Thr Ala Thr Ala
705                 710                 715                 720

Thr Gly Arg Leu Ser Ser Ser Asp Pro Asn Leu Gln Asn Ile Pro Val
                725                 730                 735

Arg Thr Pro Leu Gly Gln Arg Ile Arg Arg Ala Phe Ile Ala Glu Glu
            740                 745                 750

Gly Trp Leu Leu Val Ala Leu Asp Tyr Ser Gln Ile Glu Leu Arg Val
        755                 760                 765

Leu Ala His Leu Ser Gly Asp Glu Asn Leu Ile Arg Val Phe Gln Glu
770                 775                 780

Gly Arg Asp Ile His Thr Glu Thr Ala Ser Trp Met Phe Gly Val Pro
785                 790                 795                 800

Arg Glu Ala Val Asp Pro Leu Met Arg Arg Ala Ala Lys Thr Ile Asn
                805                 810                 815

Phe Gly Val Leu Tyr Gly Met Ser Ala His Arg Leu Ser Gln Glu Leu
                820                 825                 830

Ala Ile Pro Tyr Glu Glu Ala Gln Ala Phe Ile Glu Arg Tyr Phe Gln
            835                 840                 845

Ser Phe Pro Lys Val Arg Ala Trp Ile Glu Lys Thr Leu Glu Glu Gly
850                 855                 860

Arg Arg Arg Gly Tyr Val Glu Thr Leu Phe Gly Arg Arg Arg Tyr Val
865                 870                 875                 880

Pro Asp Leu Glu Ala Arg Val Lys Ser Val Arg Glu Ala Ala Glu Arg
                885                 890                 895

Met Ala Phe Asn Met Pro Val Gln Gly Thr Ala Ala Asp Leu Met Lys
            900                 905                 910

Leu Ala Met Val Lys Leu Phe Pro Arg Leu Glu Glu Met Gly Ala Arg
        915                 920                 925
```

```
Met Leu Leu Gln Val His Asp Glu Leu Val Leu Glu Ala Pro Lys Glu
        930                 935                 940

Arg Ala Glu Ala Val Ala Arg Leu Ala Lys Glu Val Met Glu Gly Val
945                 950                 955                 960

Tyr Pro Leu Ala Val Pro Leu Glu Val Glu Val Gly Ile Gly Glu Asp
            965                 970                 975

Trp Leu Ser Ala Lys Glu
            980

<210> SEQ ID NO 13
<211> LENGTH: 66
<212> TYPE: DNA
<213> ORGANISM: Artificial Sequence
<220> FEATURE:
<223> OTHER INFORMATION: Description of Artificial Sequence: primer

<400> SEQUENCE: 13
gaattcatga gggctcgca tcaccatcac catcacgctg ctgacgatga cgataaaatg      60
aggggc                                                               66

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: primer

<400> SEQUENCE: 14

Met Arg Gly Ser His His His His His His Ala Ala Asp Asp Asp Asp
  1               5                  10                  15

Lys Met Arg Gly
            20

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
gaggcctacg ggcatcacca tcaccatcac gggtacaagg cg                       42

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: polypeptide

<400> SEQUENCE: 16

Glu Ala Tyr Gly His His His His His His Gly Tyr Lys Ala
  1               5                  10

<210> SEQ ID NO 17
<211> LENGTH: 894
<212> TYPE: PRT
<213> ORGANISM: Artificial Sequence
<220> FEATURE:
<223> OTHER INFORMATION: Description of Artificial Sequence: amino acid

<400> SEQUENCE: 17

Met Ala Arg Leu Phe Leu Phe Asp Gly Thr Ala Leu Ala Tyr Arg Ala
```

-continued

```
  1               5                  10                 15
Tyr Tyr Ala Leu Asp Arg Ser Leu Ser Thr Ser Thr Gly Ile Pro Thr
             20                  25                 30

Asn Ala Thr Tyr Gly Val Ala Arg Met Leu Val Arg Phe Ile Lys Asp
             35                  40                 45

His Ile Ile Val Gly Lys Asp Tyr Val Ala Val Ala Phe Asp Lys Lys
             50                  55                 60

Ala Ala Thr Phe Arg His Lys Leu Leu Glu Thr Tyr Lys Ala Gln Arg
 65              70                  75                 80

Pro Lys Thr Pro Asp Leu Leu Ile Gln Gln Leu Pro Tyr Ile Lys Lys
             85                  90                 95

Leu Val Glu Ala Leu Gly Met Lys Val Leu Glu Val Glu Gly Tyr Glu
            100                 105                110

Ala Asp Asp Ile Ile Ala Thr Leu Ala Val Lys Gly Leu Pro Leu Phe
            115                 120                125

Asp Glu Ile Phe Ile Val Thr Gly Asp Lys Asp Met Leu Gln Leu Val
            130                 135                140

Asn Glu Lys Ile Lys Val Trp Arg Ile Val Lys Gly Ile Ser Asp Leu
145                 150                 155                160

Glu Leu Tyr Asp Ala Gln Lys Val Lys Glu Lys Tyr Gly Val Glu Pro
                165                 170                175

Gln Gln Ile Pro Asp Leu Leu Ala Leu Thr Gly Asp Glu Ile Asp Asn
            180                 185                190

Ile Pro Gly Val Thr Gly Ile Gly Glu Lys Thr Ala Val Gln Leu Leu
            195                 200                205

Glu Lys Tyr Lys Asp Leu Glu Asp Ile Leu Asn His Val Arg Glu Leu
    210                 215                 220

Pro Gln Lys Val Arg Lys Ala Leu Leu Arg Asp Arg Glu Asn Ala Ile
225                 230                 235                240

Leu Ser Lys Lys Leu Ala Ile Leu Glu Thr Asn Val Pro Ile Glu Ile
                245                 250                255

Asn Trp Glu Glu Leu Arg Tyr Gln Gly Tyr Asp Arg Glu Lys Leu Leu
            260                 265                270

Pro Leu Leu Lys Glu Leu Glu Phe Ala Ser Ile Met Lys Glu Leu Gln
    275                 280                 285

Leu Tyr Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                320

Ala Ile Asp Leu Glu Thr Ser Ser Leu Asp Pro Phe Asp Cys Asp Ile
                325                 330                335

Val Gly Ile Ser Val Ser Phe Lys Pro Lys Glu Ala Tyr Tyr Ile Pro
                340                 345                350

Leu His His Arg Asn Ala Gln Asn Leu Asp Glu Lys Glu Val Leu Lys
            355                 360                365

Lys Leu Lys Glu Ile Leu Glu Asp Pro Gly Ala Lys Ile Val Gly Gln
    370                 375                 380

Asn Leu Lys Phe Asp Tyr Lys Val Leu Met Val Lys Gly Val Glu Pro
385                 390                 395                400

Val Pro Pro His Phe Asp Thr Met Ile Ala Ala Tyr Leu Leu Glu Pro
                405                 410                415

Asn Glu Lys Lys Phe Asn Leu Asp Asp Leu Ala Leu Lys Phe Leu Gly
            420                 425                430
```

```
Tyr Lys Met Thr Ser Tyr Gln Glu Leu Met Ser Phe Ser Pro Leu
            435                 440                 445

Phe Gly Phe Ser Phe Ala Asp Val Pro Val Glu Lys Ala Ala Asn Tyr
            450                 455                 460

Ser Cys Glu Asp Ala Asp Ile Thr Tyr Arg Leu Tyr Lys Ile Leu Ser
465                 470                 475                 480

Leu Lys Leu His Glu Ala Asp Leu Glu Asn Val Phe Tyr Lys Ile Glu
                485                 490                 495

Met Pro Leu Val Ser Val Leu Ala Arg Met Glu Leu Asn Gly Val Lys
            500                 505                 510

Val Asp Arg Asp Ala Leu Ile Gln Tyr Thr Lys Glu Ile Glu Asn Lys
            515                 520                 525

Ile Leu Lys Leu Glu Thr Gln Ile Tyr Gln Ile Ala Gly Glu Trp Phe
            530                 535                 540

Asn Ile Asn Ser Pro Lys Gln Leu Ser Tyr Ile Leu Phe Glu Lys Leu
545                 550                 555                 560

Lys Leu Pro Val Ile Lys Lys Thr Lys Thr Gly Tyr Ser Thr Asp Ala
                565                 570                 575

Glu Val Leu Glu Glu Leu Phe Asp Lys His Glu Ile Val Pro Leu Ile
            580                 585                 590

Leu Asp Tyr Arg Met Tyr Thr Lys Ile Leu Thr Thr Tyr Cys Gln Gly
            595                 600                 605

Leu Leu Gln Ala Ile Asn Pro Ser Ser Gly Arg Val His Thr Thr Phe
            610                 615                 620

Ile Gln Thr Gly Thr Ala Thr Gly Arg Leu Ala Ser Ser Asp Pro Asn
625                 630                 635                 640

Leu Gln Asn Ile Pro Val Lys Tyr Asp Glu Gly Lys Leu Ile Arg Lys
                645                 650                 655

Val Phe Val Pro Glu Gly Gly His Val Leu Ile Asp Ala Asp Tyr Ser
            660                 665                 670

Gln Ile Glu Leu Arg Ile Leu Ala His Ile Ser Glu Asp Glu Arg Leu
            675                 680                 685

Ile Ser Ala Phe Lys Asn Asn Val Asp Ile His Ser Gln Thr Ala Ala
            690                 695                 700

Glu Val Phe Gly Val Asp Ile Ala Asp Val Thr Pro Glu Met Arg Ser
705                 710                 715                 720

Gln Ala Lys Ala Val Asn Phe Gly Ile Val Tyr Gly Ile Ser Asp Tyr
                725                 730                 735

Gly Leu Ala Arg Asp Ile Lys Ile Ser Arg Lys Glu Ala Ala Glu Phe
            740                 745                 750

Ile Asn Lys Tyr Phe Glu Arg Tyr Pro Lys Val Lys Glu Tyr Leu Asp
            755                 760                 765

Asn Thr Val Lys Phe Ala Arg Asp Asn Gly Phe Val Leu Thr Leu Phe
            770                 775                 780

Asn Arg Lys Arg Tyr Ile Lys Asp Ile Lys Ser Thr Asn Arg Asn Leu
785                 790                 795                 800

Arg Gly Tyr Ala Glu Arg Ile Ala Met Asn Ser Pro Ile Gln Gly Ser
                805                 810                 815

Ala Ala Asp Ile Met Lys Leu Ala Met Ile Lys Val Tyr Gln Lys Leu
            820                 825                 830

Lys Glu Asn Asn Leu Lys Ser Lys Ile Ile Leu Gln Val His Asp Glu
            835                 840                 845
```

```
Leu Leu Ile Glu Ala Pro Tyr Glu Lys Asp Ile Val Lys Glu Ile
    850                 855                 860

Val Lys Arg Glu Met Glu Asn Ala Val Ala Leu Lys Val Pro Leu Val
865                 870                 875                 880

Val Glu Val Lys Glu Gly Leu Asn Trp Tyr Glu Asn Lys Ile
                885                 890

<210> SEQ ID NO 18
<211> LENGTH: 893
<212> TYPE: PRT
<213> ORGANISM: T. neapolitana

<400> SEQUENCE: 18

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
            20                  25                  30

Asn Ala Thr Tyr Gly Val Ala Arg Met Leu Val Arg Phe Ile Lys Asp
        35                  40                  45

His Ile Ile Val Gly Lys Asp Tyr Val Ala Val Ala Phe Asp Lys Lys
    50                  55                  60

Ala Ala Thr Phe Arg His Lys Leu Leu Glu Thr Tyr Lys Ala Gln Arg
65                  70                  75                  80

Pro Lys Thr Pro Asp Leu Leu Ile Gln Gln Leu Pro Tyr Ile Lys Lys
                85                  90                  95

Leu Val Glu Ala Leu Gly Met Lys Val Leu Glu Val Glu Gly Tyr Glu
            100                 105                 110

Ala Asp Asp Ile Ile Ala Thr Leu Ala Val Lys Gly Leu Pro Leu Phe
        115                 120                 125

Asp Glu Ile Phe Ile Val Thr Gly Asp Lys Asp Met Leu Gln Leu Val
130                 135                 140

Asn Glu Lys Ile Lys Val Trp Arg Ile Val Lys Gly Ile Ser Asp Leu
145                 150                 155                 160

Glu Leu Tyr Asp Ala Gln Lys Val Lys Glu Lys Tyr Gly Val Glu Pro
                165                 170                 175

Gln Gln Ile Pro Asp Leu Leu Ala Leu Thr Gly Asp Glu Ile Asp Asn
            180                 185                 190

Ile Pro Gly Val Thr Gly Ile Gly Glu Lys Thr Ala Val Gln Leu Leu
        195                 200                 205

Glu Lys Tyr Lys Asp Leu Glu Asp Ile Leu Asn His Val Arg Glu Leu
    210                 215                 220

Pro Gln Lys Val Arg Lys Ala Leu Leu Arg Asp Arg Glu Asn Ala Ile
225                 230                 235                 240

Leu Ser Lys Lys Leu Ala Ile Leu Glu Thr Asn Val Pro Ile Glu Ile
                245                 250                 255

Asn Trp Glu Glu Leu Arg Tyr Gln Gly Tyr Asp Arg Glu Lys Leu Leu
            260                 265                 270

Pro Leu Leu Lys Glu Leu Glu Phe Ala Ser Ile Met Lys Glu Leu Gln
        275                 280                 285

Leu Tyr Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335
```

```
Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
            370                 375                 380

Asn Leu Lys Phe Asp Tyr Lys Val Leu Met Val Lys Gly Val Glu Pro
385                 390                 395                 400

Val Pro Pro His Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Ser Pro Leu
            435                 440                 445

Phe Gly Phe Ser Phe Ala Asp Val Pro Val Glu Lys Ala Ala Asn Tyr
            450                 455                 460

Ser Cys Glu Asp Ala Asp Ile Thr Tyr Arg Leu Tyr Lys Ile Leu Ser
465                 470                 475                 480

Leu Lys Leu His Glu Ala Asp Leu Glu Asn Val Phe Tyr Lys Ile Glu
                485                 490                 495

Met Pro Leu Val Ser Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
            515                 520                 525

Leu Glu Glu Leu Ala Glu Ile Tyr Arg Ile Ala Gly Glu Pro Phe
            530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
            595                 600                 605

Asp Ala Leu Pro Lys Met Val Asn Pro Lys Thr Gly Arg Ile His Ala
            610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
            675                 680                 685

Glu Asn Leu Leu Arg Ala Phe Glu Gly Ile Asp Val His Thr Leu
            690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
            740                 745                 750
```

```
Glu Lys Met Ile Val Asn Tyr Phe Val Leu Tyr Pro Lys Val Arg Asp
            755                 760                 765

Tyr Ile Gln Arg Val Val Ser Glu Ala Lys Glu Lys Gly Tyr Val Arg
        770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
        835                 840                 845

His Asp Glu Leu Val Phe Glu Val Pro Asn Glu Glu Lys Asp Ala Leu
    850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
            885                 890

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 19
ctgaccatgg cgagactatt tctctttg                                    28

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 20
tctgtcgacc ttcacaccgt tcagttccat cc                               32

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 21
aaggtcgaca gagatgccct catccaatat acc                              33

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 22
tagcaagctt ctattttgtc tcataccagt                                  30

<210> SEQ ID NO 23
<211> LENGTH: 60
<212> TYPE: PRT
```

<213> ORGANISM: Artificial Sequence
<220> FEATURE:
<223> OTHER INFORMATION: Description of Artificial Sequence: polypeptide

<400> SEQUENCE: 23

Ile Glu Met Pro Leu Val Ser Val Leu Ala Arg Met Glu Leu Asn Gly
 1               5                  10                  15

Val Lys Val Asp Arg Asp Ala Leu Ile Gln Tyr Thr Lys Glu Ile Glu
            20                  25                  30

Asn Lys Ile Leu Lys Leu Glu Thr Gln Ile Tyr Gln Ile Ala Gly Glu
        35                  40                  45

Trp Phe Asn Ile Asn Ser Pro Lys Gln Leu Ser Tyr
    50                  55                  60

<210> SEQ ID NO 24
<211> LENGTH: 60
<212> TYPE: PRT
<213> ORGANISM: T. neapolitana

<400> SEQUENCE: 24

Ile Glu Met Pro Leu Val Ser Val Leu Ala Arg Met Glu Leu Asn Gly
 1               5                  10                  15

Val Tyr Val Asp Thr Glu Phe Leu Lys Lys Leu Ser Glu Glu Tyr Gly
            20                  25                  30

Lys Lys Leu Glu Glu Leu Ala Glu Glu Ile Tyr Arg Ile Ala Gly Glu
        35                  40                  45

Pro Phe Asn Ile Asn Ser Pro Lys Gln Val Ser Arg
    50                  55                  60

<210> SEQ ID NO 25
<211> LENGTH: 60
<212> TYPE: PRT
<213> ORGANISM: Anaerocellum thermophilum

<400> SEQUENCE: 25

Ile Glu Arg Pro Leu Ile Pro Val Leu Tyr Glu Met Glu Lys Thr Gly
 1               5                  10                  15

Phe Lys Val Asp Arg Asp Ala Leu Ile Gln Tyr Thr Lys Glu Ile Glu
            20                  25                  30

Asn Lys Ile Leu Lys Leu Glu Thr Gln Ile Tyr Gln Ile Ala Gly Glu
        35                  40                  45

Trp Phe Asn Ile Asn Ser Pro Lys Gln Leu Ser Tyr
    50                  55                  60

<210> SEQ ID NO 26
<211> LENGTH: 27
<212> TYPE: DNA
<213> ORGANISM: T. neapolitana

<400> SEQUENCE: 26
atggcgagac tatttctctt tgatgga                                          27

<210> SEQ ID NO 27
<211> LENGTH: 9
<212> TYPE: PRT
<213> ORGANISM: T. neapolitana

<400> SEQUENCE: 27

Met Ala Arg Leu Phe Leu Phe Asp Gly
 1               5

```
<210> SEQ ID NO 28
<211> LENGTH: 51
<212> TYPE: DNA
<213> ORGANISM: T. neapolitana

<400> SEQUENCE: 28
cggatggaac tgaacggtgt gtacgtggac acagagttcc tgaagaaact c          51

<210> SEQ ID NO 29
<211> LENGTH: 17
<212> TYPE: PRT
<213> ORGANISM: T. neapolitana

<400> SEQUENCE: 29

Arg Met Glu Leu Asn Gly Val Tyr Val Asp Thr Glu Phe Leu Lys Lys
 1               5                  10                  15

Leu

<210> SEQ ID NO 30
<211> LENGTH: 51
<212> TYPE: DNA
<213> ORGANISM: Anaerocellum thermophilum

<400> SEQUENCE: 30
atggaaaaaa caggatttaa ggtggataga gatgccctca tccaatatac c          51

<210> SEQ ID NO 31
<211> LENGTH: 17
<212> TYPE: PRT
<213> ORGANISM: Anaerocellum thermophilum

<400> SEQUENCE: 31

Met Glu Lys Thr Gly Phe Lys Val Asp Arg Asp Ala Leu Ile Gln Tyr
 1               5                  10                  15

Thr

<210> SEQ ID NO 32
<211> LENGTH: 27
<212> TYPE: DNA
<213> ORGANISM: Anaerocellum thermophilum

<400> SEQUENCE: 32
ggactgaact ggtatgagac aaaatag                                     27

<210> SEQ ID NO 33
<211> LENGTH: 8
<212> TYPE: PRT
<213> ORGANISM: Anaerocellum thermophilum

<400> SEQUENCE: 33

Gly Leu Asn Trp Tyr Glu Thr Lys
 1               5

<210> SEQ ID NO 34
<211> LENGTH: 60
<212> TYPE: PRT
<213> ORGANISM: Artificial Sequence
<220> FEATURE:
<223> OTHER INFORMATION: Description of Artificial Sequence: amino acid

<400> SEQUENCE: 34

Ile Met Glu Pro Leu Val Ser Val Leu Ala Arg Met Glu Leu Asn Gly
 1               5                  10                  15
```

-continued

```
Val Tyr Val Asp Thr Glu Phe Leu Lys Lys Leu Ser Glu Glu Tyr Gly
             20                  25                  30

Lys Lys Leu Glu Glu Leu Ala Glu Glu Ile Tyr Arg Ile Ala Gly Glu
         35                  40                  45

Pro Phe Asn Ile Asn Ser Pro Lys Gln Val Ser Arg
     50                  55                  60

<210> SEQ ID NO 35
<211> LENGTH: 60
<212> TYPE: PRT
<213> ORGANISM: T. neapolitana

<400> SEQUENCE: 35

Ile Glu Met Pro Leu Val Ser Val Leu Ala Arg Met Glu Leu Asn Gly
 1               5                  10                  15

Val Tyr Val Asp Thr Glu Phe Leu Lys Lys Leu Ser Glu Glu Tyr Gly
             20                  25                  30

Lys Lys Leu Glu Glu Leu Ala Glu Glu Ile Tyr Arg Ile Ala Gly Glu
         35                  40                  45

Pro Phe Asn Ile Asn Ser Pro Lys Gln Val Ser Arg
     50                  55                  60

<210> SEQ ID NO 36
<211> LENGTH: 60
<212> TYPE: PRT
<213> ORGANISM: Anaerocellum thermophilum

<400> SEQUENCE: 36

Ile Glu Arg Pro Leu Ile Pro Val Leu Tyr Glu Met Glu Lys Thr Gly
 1               5                  10                  15

Phe Lys Val Asp Arg Asp Ala Leu Ile Gln Tyr Thr Lys Glu Ile Glu
             20                  25                  30

Asn Lys Ile Leu Lys Leu Glu Thr Gln Ile Tyr Gln Ile Ala Gly Glu
         35                  40                  45

Trp Phe Asn Ile Asn Ser Pro Lys Gln Leu Ser Arg
     50                  55                  60

<210> SEQ ID NO 37
<211> LENGTH: 48
<212> TYPE: DNA
<213> ORGANISM: T. neapolitana

<400> SEQUENCE: 37
tcaccgaagc aggtttcaag gatccttttt gaaaaactcg gcataaaa            48

<210> SEQ ID NO 38
<211> LENGTH: 16
<212> TYPE: PRT
<213> ORGANISM: T. neapolitana

<400> SEQUENCE: 38

Ser Pro Lys Gln Val Ser Arg Ile Leu Phe Glu Lys Leu Gly Ile Lys
 1               5                  10                  15

<210> SEQ ID NO 39
<211> LENGTH: 48
<212> TYPE: DNA
<213> ORGANISM: Anaerocellum thermophilum

<400> SEQUENCE: 39
```

```
tcaccgaaac agctttctta cattttgttt gaaaagctaa aacttcct         48
```

<210> SEQ ID NO 40
<211> LENGTH: 16
<212> TYPE: PRT
<213> ORGANISM: Anaerocellum thermophilum

<400> SEQUENCE: 40

Ser Pro Lys Gln Leu Ser Tyr Ile Leu Phe Glu Lys Leu Lys Leu Pro
 1               5                  10                  15

<210> SEQ ID NO 41
<211> LENGTH: 47
<212> TYPE: DNA
<213> ORGANISM: Artificial Sequence
<220> FEATURE:
<223> OTHER INFORMATION: Description of Artificial Sequence: amino acid

<400> SEQUENCE: 41

```
caccgaaaca gctttctagg atcctgtttg aaaagctaaa acttcct          47
```

<210> SEQ ID NO 42
<211> LENGTH: 48
<212> TYPE: DNA
<213> ORGANISM: Artificial Sequence
<220> FEATURE:
<223> OTHER INFORMATION: Description of Artificial Sequence: amino acid

<400> SEQUENCE: 42

```
gtggctttgt cgaaagatcc taggacaaac ttttcgattt tgaaggac         48
```

<210> SEQ ID NO 43
<211> LENGTH: 851
<212> TYPE: PRT
<213> ORGANISM: Anaerocellum thermophilum

<400> SEQUENCE: 43

Met Lys Leu Val Ile Phe Asp Gly Asn Ser Ile Leu Tyr Arg Ala Phe
 1               5                  10                  15

Phe Ala Leu Pro Glu Leu Thr Thr Ser Asn Asn Ile Pro Thr Asn Ala
                20                  25                  30

Ile Tyr Gly Phe Val Asn Val Ile Leu Lys Tyr Leu Glu Gln Glu Lys
            35                  40                  45

Pro Asp Tyr Val Ala Val Ala Phe Asp Lys Arg Gly Arg Glu Ala Arg
        50                  55                  60

Lys Ser Glu Tyr Glu Glu Tyr Lys Ala Asn Arg Lys Pro Met Pro Asp
65                  70                  75                  80

Asn Leu Gln Val Gln Ile Pro Tyr Val Arg Glu Ile Leu Tyr Ala Phe
                85                  90                  95

Asn Ile Pro Ile Ile Glu Phe Glu Gly Tyr Glu Ala Asp Asp Val Ile
            100                 105                 110

Gly Ser Leu Val Asn Gln Phe Lys Asn Thr Gly Leu Asp Ile Val Ile
        115                 120                 125

Ile Thr Gly Asp Arg Asp Thr Leu Gln Leu Leu Asp Lys Asn Val Val
    130                 135                 140

Val Lys Ile Val Ser Thr Lys Phe Asp Lys Thr Val Glu Asp Leu Tyr
145                 150                 155                 160

Thr Val Glu Asn Val Lys Glu Lys Tyr Gly Val Trp Ala Asn Gln Val
                165                 170                 175

Pro Asp Tyr Lys Ala Leu Val Gly Asp Gln Ser Asp Asn Ile Pro Gly

-continued

```
                180                 185                 190
Val Lys Gly Ile Gly Glu Lys Ser Ala Gln Lys Leu Leu Glu Glu Tyr
            195                 200                 205

Ser Ser Leu Glu Glu Ile Tyr Gln Asn Leu Asp Lys Ile Lys Ser Ser
        210                 215                 220

Ile Arg Glu Lys Leu Glu Ala Gly Lys Asp Met Ala Phe Leu Ser Lys
225                 230                 235                 240

Arg Leu Ala Thr Ile Val Cys Asp Leu Pro Leu Asn Val Lys Leu Glu
                245                 250                 255

Asp Leu Arg Thr Lys Glu Trp Asn Lys Glu Arg Leu Tyr Glu Ile Leu
            260                 265                 270

Val Gln Leu Glu Phe Lys Ser Ile Ile Lys Arg Leu Gly Leu Ser Glu
        275                 280                 285

Val Val Gln Phe Glu Phe Val Gln Gln Arg Thr Asp Ile Pro Asp Val
    290                 295                 300

Glu Gln Lys Glu Leu Glu Ser Ile Ser Gln Ile Arg Ser Lys Glu Ile
305                 310                 315                 320

Pro Leu Met Phe Val Gln Gly Glu Lys Cys Phe Tyr Leu Tyr Asp Gln
                325                 330                 335

Glu Ser Asn Thr Val Phe Ile Thr Ser Asn Lys Leu Leu Ile Glu Glu
            340                 345                 350

Ile Leu Lys Ser Asp Thr Val Lys Ile Met Tyr Asp Leu Lys Asn Ile
        355                 360                 365

Phe His Gln Leu Asn Leu Glu Asp Thr Asn Asn Ile Lys Asn Cys Glu
    370                 375                 380

Asp Val Met Ile Ala Ser Tyr Val Leu Asp Ser Thr Arg Ser Ser Tyr
385                 390                 395                 400

Glu Leu Glu Thr Leu Phe Val Ser Tyr Leu Asn Thr Asp Ile Glu Ala
                405                 410                 415

Val Lys Lys Asp Lys Lys Ile Val Ser Val Val Leu Leu Lys Arg Leu
            420                 425                 430

Trp Asp Glu Leu Leu Arg Leu Ile Asp Leu Asn Ser Cys Gln Phe Leu
        435                 440                 445

Tyr Glu Asn Ile Glu Arg Pro Leu Ile Pro Val Leu Tyr Glu Met Glu
    450                 455                 460

Lys Thr Gly Phe Lys Val Asp Arg Asp Ala Leu Ile Gln Tyr Thr Lys
465                 470                 475                 480

Glu Ile Glu Asn Lys Ile Leu Lys Leu Glu Thr Gln Ile Tyr Gln Ile
                485                 490                 495

Ala Gly Glu Trp Phe Asn Ile Asn Ser Pro Lys Gln Leu Ser Tyr Ile
            500                 505                 510

Leu Phe Glu Lys Leu Lys Leu Pro Val Ile Lys Lys Thr Lys Thr Gly
        515                 520                 525

Tyr Ser Thr Asp Ala Glu Val Leu Glu Glu Leu Phe Asp Lys His Glu
    530                 535                 540

Ile Val Pro Leu Ile Leu Asp Tyr Arg Met Tyr Thr Lys Ile Leu Thr
545                 550                 555                 560

Thr Tyr Cys Gln Gly Leu Leu Gln Ala Ile Asn Pro Ser Ser Gly Arg
                565                 570                 575

Val His Thr Thr Phe Ile Gln Thr Gly Thr Ala Thr Gly Arg Leu Ala
            580                 585                 590

Ser Ser Asp Pro Asn Leu Gln Asn Ile Pro Val Lys Tyr Asp Glu Gly
        595                 600                 605
```

```
Lys Leu Ile Arg Lys Val Phe Val Pro Glu Gly Gly His Val Leu Ile
    610                 615                 620

Asp Ala Asp Tyr Ser Gln Ile Glu Leu Arg Ile Leu Ala His Ile Ser
625                 630                 635                 640

Glu Asp Glu Arg Leu Ile Ser Ala Phe Lys Asn Asn Val Asp Ile His
                645                 650                 655

Ser Gln Thr Ala Ala Glu Val Phe Gly Val Asp Ile Ala Asp Val Thr
                660                 665                 670

Pro Glu Met Arg Ser Gln Ala Lys Ala Val Asn Phe Gly Ile Val Tyr
            675                 680                 685

Gly Ile Ser Asp Tyr Gly Leu Ala Arg Asp Ile Lys Ile Ser Arg Lys
    690                 695                 700

Glu Ala Ala Glu Phe Ile Asn Lys Tyr Phe Glu Arg Tyr Pro Lys Val
705                 710                 715                 720

Lys Glu Tyr Leu Asp Asn Thr Val Lys Phe Ala Arg Asp Asn Gly Phe
                725                 730                 735

Val Leu Thr Leu Phe Asn Arg Lys Arg Tyr Ile Lys Asp Ile Lys Ser
                740                 745                 750

Thr Asn Arg Asn Leu Arg Gly Tyr Ala Glu Arg Ile Ala Met Asn Ser
            755                 760                 765

Pro Ile Gln Gly Ser Ala Ala Asp Ile Met Lys Leu Ala Met Ile Lys
    770                 775                 780

Val Tyr Gln Lys Leu Lys Glu Asn Asn Leu Lys Ser Lys Ile Ile Leu
785                 790                 795                 800

Gln Val His Asp Glu Leu Leu Ile Glu Ala Pro Tyr Glu Glu Lys Asp
                805                 810                 815

Ile Val Lys Glu Ile Val Lys Arg Glu Met Glu Asn Ala Val Ala Leu
                820                 825                 830

Lys Val Pro Leu Val Val Glu Val Lys Glu Gly Leu Asn Trp Tyr Glu
            835                 840                 845

Asn Lys Ile
    850

<210> SEQ ID NO 44
<211> LENGTH: 928
<212> TYPE: PRT
<213> ORGANISM: E. coli

<400> SEQUENCE: 44

Met Val Gln Ile Pro Gln Asn Pro Leu Ile Leu Val Asp Gly Ser Ser
1               5                   10                  15

Tyr Leu Tyr Arg Ala Tyr His Ala Phe Pro Pro Leu Thr Asn Ser Ala
                20                  25                  30

Gly Glu Pro Thr Gly Ala Met Tyr Gly Val Leu Asn Met Leu Arg Ser
            35                  40                  45

Leu Ile Met Gln Tyr Lys Pro Thr His Ala Ala Val Val Phe Asp Ala
    50                  55                  60

Lys Gly Lys Thr Phe Arg Asp Glu Leu Phe Glu His Tyr Lys Ser His
65                  70                  75                  80

Arg Pro Pro Met Pro Asp Asp Leu Arg Ala Gln Ile Glu Pro Leu His
                85                  90                  95
```

```
Ala Met Val Lys Ala Met Gly Leu Pro Leu Leu Ala Val Ser Gly Val
            100                 105                 110

Glu Ala Asp Asp Val Ile Gly Thr Leu Ala Arg Glu Ala Glu Lys Ala
            115                 120                 125

Gly Arg Pro Val Leu Ile Ser Thr Gly Asp Lys Asp Met Ala Gln Leu
            130                 135                 140

Val Thr Pro Asn Ile Thr Leu Ile Asn Thr Met Thr Asn Thr Ile Leu
145                 150                 155                 160

Gly Pro Glu Glu Val Val Asn Lys Tyr Gly Val Pro Pro Glu Leu Ile
                    165                 170                 175

Ile Asp Phe Leu Ala Leu Met Gly Asp Ser Ser Asp Asn Ile Pro Gly
                180                 185                 190

Val Pro Gly Val Gly Glu Lys Thr Ala Gln Ala Leu Leu Gln Gly Leu
                195                 200                 205

Gly Gly Leu Asp Thr Leu Tyr Ala Glu Pro Glu Lys Ile Ala Gly Leu
            210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
                245                 250                 255

Glu Leu Glu Leu Thr Cys Glu Gln Leu Glu Val Gln Gln Pro Ala Ala
                260                 265                 270

Glu Glu Leu Leu Gly Leu Phe Lys Lys Tyr Glu Phe Lys Arg Trp Thr
            275                 280                 285

Ala Asp Val Glu Ala Gly Lys Trp Leu Gln Ala Lys Gly Ala Lys Pro
            290                 295                 300

Ala Ala Lys Pro Gln Glu Thr Ser Val Ala Asp Glu Ala Pro Glu Val
305                 310                 315                 320

Thr Ala Thr Val Ile Ser Tyr Asp Asn Tyr Val Thr Ile Leu Asp Glu
                325                 330                 335

Glu Thr Leu Lys Ala Trp Ile Ala Lys Leu Glu Lys Ala Pro Val Phe
            340                 345                 350

Ala Phe Asp Thr Glu Thr Asp Ser Leu Asp Asn Ile Ser Ala Asn Leu
            355                 360                 365

Val Gly Leu Ser Phe Ala Ile Glu Pro Gly Val Ala Ala Tyr Ile Pro
            370                 375                 380

Val Ala His Asp Tyr Leu Asp Ala Pro Asp Gln Ile Ser Arg Glu Arg
385                 390                 395                 400

Ala Leu Glu Leu Leu Lys Pro Leu Leu Glu Asp Glu Lys Ala Leu Lys
                405                 410                 415

Val Gly Gln Asn Leu Lys Tyr Asp Arg Gly Ile Leu Ala Asn Tyr Gly
                420                 425                 430

Ile Glu Leu Arg Gly Ile Ala Phe Asp Thr Met Leu Glu Ser Tyr Ile
            435                 440                 445

Leu Asn Ser Val Ala Gly Arg His Asp Met Asp Ser Leu Ala Glu Arg
450                 455                 460

Trp Leu Lys His Lys Thr Ile Thr Phe Glu Glu Ile Ala Gly Lys Gly
465                 470                 475                 480

Lys Asn Gln Leu Thr Phe Asn Gln Ile Ala Leu Glu Glu Ala Gly Arg
                485                 490                 495

Tyr Ala Ala Glu Asp Ala Asp Val Thr Leu Gln Leu His Leu Lys Met
                500                 505                 510
```

-continued

```
Trp Pro Asp Leu Gln Lys His Lys Gly Pro Leu Asn Val Phe Glu Asn
        515                 520                 525

Ile Glu Met Pro Leu Val Pro Val Leu Ser Arg Ile Glu Arg Asn Gly
        530                 535                 540

Val Lys Ile Asp Pro Lys Val Leu His Asn His Ser Glu Glu Leu Thr
545                 550                 555                 560

Leu Arg Leu Ala Glu Leu Glu Lys Lys Ala His Glu Ile Ala Gly Glu
                565                 570                 575

Glu Phe Asn Leu Ser Ser Thr Lys Gln Leu Gln Thr Ile Leu Phe Glu
            580                 585                 590

Lys Gln Gly Ile Lys Pro Leu Lys Lys Thr Pro Gly Gly Ala Pro Ser
            595                 600                 605

Thr Ser Glu Glu Val Leu Glu Glu Leu Ala Leu Asp Tyr Pro Leu Pro
        610                 615                 620

Lys Val Ile Leu Glu Tyr Arg Gly Leu Ala Lys Leu Lys Ser Thr Tyr
625                 630                 635                 640

Thr Asp Lys Leu Pro Leu Met Ile Asn Pro Lys Thr Gly Arg Val His
                645                 650                 655

Thr Ser Tyr His Gln Ala Val Thr Ala Thr Gly Arg Leu Ser Ser Thr
            660                 665                 670

Asp Pro Asn Leu Gln Asn Ile Pro Val Arg Asn Glu Glu Gly Arg Arg
            675                 680                 685

Ile Arg Gln Ala Phe Ile Ala Pro Glu Asp Tyr Val Ile Val Ser Ala
        690                 695                 700

Asp Tyr Ser Gln Ile Glu Leu Arg Ile Met Ala His Leu Ser Arg Asp
705                 710                 715                 720

Lys Gly Leu Leu Thr Ala Phe Ala Glu Gly Lys Asp Ile His Arg Ala
                725                 730                 735

Thr Ala Ala Glu Val Phe Gly Leu Pro Leu Glu Thr Val Thr Ser Glu
            740                 745                 750

Gln Arg Arg Ser Ala Lys Ala Ile Asn Phe Gly Leu Ile Tyr Gly Met
        755                 760                 765

Ser Ala Phe Gly Leu Ala Arg Gln Leu Asn Ile Pro Arg Lys Glu Ala
        770                 775                 780

Gln Lys Tyr Met Asp Leu Tyr Phe Glu Arg Tyr Pro Gly Val Leu Glu
785                 790                 795                 800

Tyr Met Glu Arg Thr Arg Ala Gln Ala Lys Glu Gln Gly Tyr Val Glu
                805                 810                 815

Thr Leu Asp Gly Arg Arg Leu Tyr Leu Pro Asp Ile Lys Ser Ser Asn
            820                 825                 830

Gly Ala Arg Arg Ala Ala Ala Glu Arg Ala Ala Ile Asn Ala Pro Met
        835                 840                 845

Gln Gly Thr Ala Ala Asp Ile Ile Lys Arg Ala Met Ile Ala Val Asp
850                 855                 860

Ala Trp Leu Gln Ala Glu Gln Pro Arg Val Arg Met Ile Met Gln Val
865                 870                 875                 880

His Asp Glu Leu Val Phe Glu Val His Lys Asp Asp Val Asp Ala Val
                885                 890                 895

Ala Lys Gln Ile His Gln Leu Met Glu Asn Cys Thr Arg Leu Asp Val
            900                 905                 910

Pro Leu Leu Val Glu Val Gly Ser Gly Glu Asn Trp Asp Gln Ala His
        915                 920                 925
```